United States Patent [19]

Oldenburg et al.

[11] Patent Number: 5,814,603
[45] Date of Patent: Sep. 29, 1998

[54] COMPOUNDS WITH PTH ACTIVITY

[75] Inventors: Kevin R. Oldenburg, Fremont; Harold E. Selick, Belmont, both of Calif.

[73] Assignee: Affymax Technologies N.V., Greenford, England

[21] Appl. No.: 142,551

[22] Filed: Oct. 25, 1993

Related U.S. Application Data

[63] Continuation-in-part of Ser. No. 965,677, Oct. 22, 1992, abandoned, Ser. No. 77,296, Jun. 14, 1993, abandoned, and Ser. No. 898,219, Jun. 12, 1992, abandoned.

[51] Int. Cl.⁶ .......................... A61K 38/29; C07K 1/113
[52] U.S. Cl. ............................... 514/17; 530/4; 530/399; 530/402
[58] Field of Search ................................ 424/562; 514/2, 514/12; 530/324, 399, 402; 435/69.1, 69.4, 252.3, 320.1; 536/22.1, 23.1, 23.4, 23.5, 23.51

[56] References Cited

U.S. PATENT DOCUMENTS

| | | | |
|---|---|---|---|
| 3,886,132 | 5/1975 | Brewer et al. | 530/324 |
| 4,423,037 | 12/1983 | Rosenblatt et al. | 514/12 |
| 4,632,780 | 12/1986 | Seidah et al. | 530/306 |
| 4,656,250 | 4/1987 | Morita et al. | 530/324 |
| 4,771,124 | 9/1988 | Rosenblatt et al. | 530/324 |
| 4,968,669 | 11/1990 | Rosenblatt et al. | 514/12 |
| 5,001,223 | 3/1991 | Rosenblatt et al. | 530/324 |
| 5,010,010 | 4/1991 | Gautvik et al. | 435/252.3 |
| 5,171,670 | 12/1992 | Kronenberg et al. | 435/68.1 |
| 5,455,329 | 10/1995 | Wingender et al. | 530/324 |
| 5,457,047 | 10/1995 | Wingender et al. | 435/252.3 |
| 5,589,452 | 12/1996 | Krstenansky et al. | 514/12 |
| 5,599,792 | 2/1997 | Kronis et al. | 514/12 |
| 5,693,616 | 12/1997 | Krstenansky et al. | 514/12 |
| 5,695,955 | 12/1997 | Krstenansky et al. | 435/69.4 |

FOREIGN PATENT DOCUMENTS

| | | | |
|---|---|---|---|
| 293158 | 5/1988 | European Pat. Off. | C07K 7/10 |
| 301485 | 7/1988 | European Pat. Off. | C12N 15/00 |
| 341963 | 5/1989 | European Pat. Off. | C07K 7/10 |
| 483509 | 9/1991 | European Pat. Off. | C12N 15/16 |
| 9010067 | 7/1990 | WIPO | C12N 15/16 |
| 9105050 | 4/1991 | WIPO | C12N 15/16 |
| 9200753 | 1/1992 | WIPO . | |
| 9306845 | 4/1993 | WIPO | A61K 37/36 |
| 9320203 | 10/1993 | WIPO | C12N 15/16 |
| 9401460 | 1/1994 | WIPO | C07K 7/10 |
| 9402510 | 2/1994 | WIPO | C07K 7/10 |
| 9403201 | 2/1994 | WIPO | A61K 37/02 |
| 9407514 | 4/1994 | WIPO | A61K 37/00 |

OTHER PUBLICATIONS

Potts et al. Parathyroid hormone: chemistry, biosynthesis, and mode of action. Advances in Protein Chemistry. vol. 35, pp. 323–396, 1982.

Tashijian et al., 1964, Biochemistry 3: 1175–1182 Alkylation and Oxidation of Methionine in Bovine parathyroid Hormone: Effects on Hormonal Activity and Antigenicity.

Potts et al., 1971, Proc. Natl. Acad. Sci. USA 68: 63–67 Synthesis of a Biologically Active N–Terminal Tetratriacontapeptide of Parathyroid Hormone.

Treager et al., 1973, Endocrinology 93 (6): 1349–1353 Bovine Parathyroid Hormone: Minimum Chain Length of Synthetic Peptide Required for Biological Activity.

Goltzmann et al., 1975, J. Biol. Chem. 250:3199–3203 Analysis of the Requirements for Parathyroid Hormone Action in Renal Membranes with the use of Inhibiting Analogues.

Rosenblatt et al., 1976, J. Biol. Chem. 251: 159–164 Chemical and Biological Properties of Synthetic, Sulfur–free Analogues of Parathyroid Hormone.

Goltzmann et al., 1978, Endocrinology 103: 1352–1360 Influence of Guanyl Nucleotides on Parathyroid Hormone–Stimulated Adenylyl Cyclase Activity in Renal Cortical Membranes.

Segre et al., 1979, J. Biol. Chem. 254:6980–6986 Characterization of Parathyroid Hormone Receptors in Canine Renal Cortical Plasma Membranes Using a Radiodinated Sulfur–free Hormone Analogue.

Rosenblatt, 1981, Pathobiology Annual 11:53–86 Parathyroid Hormone: Chemistry and Structure–Activity Relations.

Frelinger and Zull, 1984, J. Biol. Chem. 259: 5507–5513 Oxidized Forms of Parathyroid Hormone with Biological Activity.

Frelinger and Zull, 1986, Arch. Biochem. Biophys. 244:641–649 The Role of Methionine Residues in the Structure and Function of Parathyroid Hormone.

Zull et al., 1987, Mol. Cell. Endo. 51: 267–271 Deletion of lysine 13 alters the structure and function of parathyroid hormone.

Goldman et al., 1988, Endocrinology 123: 1468–1475 Evaluation of Novel Parathyroid Hormone analogs Using a Bovine Renal Membrane Receptor Binding Assay.

Takano et al., 1988, Acta Endo. 118:551–558 Studies of structure–function relationship of human parathyroid hormone using rat and human renal cortical cells in culture.

(List continued on next page.)

*Primary Examiner*—Elizabeth C. Kemmerer
*Assistant Examiner*—Brian Lathrop
*Attorney, Agent, or Firm*—Lauren L. Stevens; Kevin R. Kaster

[57] ABSTRACT

PTH analogs comprising an amino acid sequence that is: $SVSEIQLLHNX_1X_2X_3HX_4X_3X_3X_3X_5RVX_5WLR X_4X_4LX_3X_3VX_1X_3X_3X$ (SEQ ID NO:10) wherein $X_1$ is a neutral or positively charged amino acid, $X_2$ is a neutral amino acid, $X_3$ is a neutral, positively charged, or negatively charged amino acid, $X_4$ is a positively charged amino acid, $X_5$ is a positively charged or negatively charged amino acid, and X is selected from the group consisting of Hol, Ho, a homoserine amide, or the sequence of amino acids comprising residues 35–84 of PTH, have enhanced activity and increased serum half-life as compared with human PTH. The PTH analogs can be produced as fusion proteins in high yields in *E. coli* host cells; the fusion proteins can be subsequently cleaved to produce the PTH analog.

3 Claims, 8 Drawing Sheets

OTHER PUBLICATIONS

Zull et al., 1990, J. Biol. Chem. 265: 5671–5676 Effect of Methionine Oxidation and Deletion of Amino–terminal Residues on the Conformation of the Parathyroid Hormone.

Chorev et al., 1990, Biochemistry 29: 1580–1586 Modifications of Position 12 in Parathyroid Hormone and Parathyroid Hormone Related Protein: Toward the Design of Highly Potent Antagonists.

Gardella et al., 1990, J. Biol. Chem. 265: 15854–15859 Expression of human parathyroid hormone–(1–84) in *Escherichia coli* as a factor X–cleavable fusion protein.

Gardella et al., 1992, Endo. 132 (5): 2024–2030 Analysis of parathyroid hormone's principle receptor–binding region by site–directed mutagenesis and analog design.

Gardella et al., 1991, J. Biol. Chem. 266: 13141–13146 Mutational Analysis of the Receptor–activating Region of Human Parathyroid Hormone.

Sung et al., 1991, J. Biol. Chem. 266:2831–2835 Specific Degenerate Condons Enhanced Selective Expression of Human Parathyroid Hormone in *Escherichia coli*.

Jouishomme et al., 1992, Endocrinology 130:53–60 The Protein Kinase–C Activation Domain of the Parathyroid Hormone.

Fujimori et al., 1992, Endocrinology 130: 29–36 Structure–function relationship of parathyroid hormone: Activation of phosopholipase–C, protein kinase–A and –C in osteosarcoma cells.

Kareem et al., 1992, Analyt. Biochem. 204:26–33 A Method for the Evaluation of the Efficiency of Signal Sequences for Secretion and Correct N–terminal Processing of Human Parathyroid Hormone Produced in *Escherichia coli*.

Olstad et al., 1992, Eur. J. Biochem. 205: 311–319 Isolation and characterization of two biologically active O–glycosylated forms of human parathyroid hormone produced in *Sccharomyces cerevisiae*.

Ljunggren et al., 1992, Bioscience Reports 12 (3): 207–214 Effects of parathyroid hormone on cyclic AMP–fromation and cytoplasmic free Ca2 in the osteosarcoma cell line UMR 106–01.

Glover, 1984, Gene Cloning 110–127 The mechanics of DNA manipulation.

Cohen et al., 1991, J. Biol. Chem. 266 (3): 1997–2004 Analogues of parathyroid hormone modified at positions 3 and 6.

Pun, 1989, J. Biochem 106:1090–1093 The importance of parathyroid hormone in inhibition of collagen synthesis and mitogenesis of osteoblastic cell.

Linkhart et al., 1991, Endo. 128 (3): 1511–1518 Differential regulation of insulin–like growth factor–I (IGF–I) and IGF–II release from cultured neonatal mouse calvaria by parathyroid hormone, transforming growth factor–b, and 1,25–Dihydroxyvitamin D3.

Wronski et al., 1993, Endo. 132 (2): 823–831 Parathyroid hormones is more effective than estrogen or bisphosphonates for restoration of lost bone mass in ovariectomized rats.

Abou–Samra et al., 1993, Endo. 132 (2): 801–805 Parathyroid hormone (PTH) stimulates adrenocorticotropin release in AtT–20 cells stably expressing a common receptor for PTH and PTH–related peptide.

Tada et al., 1990, Bone 11: 163 169 Restoration of axial and appendicular bone volumes by h–PTH (1–34) in parathyroidectomized and osteopenic rats.

Ching Liu et al., 1990, J. Bone & Mineral Res. 5 (9): 973–982 Human parathyroid hormone (1–34) prevents bone loss and augments bone fromation in sexually mature ovariectomized rats.

Scott et al., 1992, Mol. Endo. 8 (12): 2153–2160 Parathyroid hormone induces transcription of collagenase in rat osteoblastic cells by a mechanism using cyclic adenosine 3'5'–monophosphate and requiring protein synthesis.

Linkhart et al., 1991, Endo. 125 (3): 1484–1491 Parathyroid hormone stimulates release of insulin()like growth factor–I (IGIF) and IGF–II from neonatal mouse calvaria in organ culture*.

HYDROPHILICITY PLOT - KYTE-DOOLITTLE

```
                                    TrpLEPTH
 M   K   A   I   F   V   L   K   G   S   L   D   R   D   P   E   F
ATG AAA GCT ATC TTC GTT CTG AAA GGT TCC CTG GAC CGT GAC CCG GAA TTC GTC GAC ATG ATC AAC

S   V   S   E   I   Q   L   L   H   N   L   G   K   H   L   N   S   L   E   R   V
ATG TCC GTT TCC GAA ATC CAG CTG CTG CAC AAC CTG GGT AAA CAC CTG AAC TCC CTC GAG CGT GTT

E   W   L   R   K   K   L   Q   D   V   H   N   Y   M
GAA TGG CTG CGT AAA AAA CTG CAG GAC GTC CAC AAC TAC ATG CAG ATC TCC CAC CAC CAC CAT CAC

CAT TAA TAA
```

FIG. 3.

COMPOUNDS WITH PTH ACTIVITY

CROSS-REFERENCE

This application is a continuation-in-part of U.S. patent application Ser. No. 07/965,677, filed Oct. 22, 1992, now abandoned, which is expressly incorporated herein by reference. This application is also a continuation-in-part of U.S. patent application Ser. No. 08/077,296, filed Jun. 14, 1993, now abandoned, which is also expressly incorporated herein by reference and a continuation-in-part of U.S. patent application Ser. No. 07/898,219, filed Jun. 12,1992, now abandoned.

BACKGROUND OF THE INVENTION

The present invention provides novel PTH analogs, recombinant DNA expression vectors, and methods for producing compounds with parathyroid hormone (PTH) activity. The invention therefore relates to the fields of molecular biology, recombinant DNA technology, and pharmacology.

Parathyroid hormone is a naturally-occurring peptide involved in bone morphogenesis and remodeling. Mammalian PTH is synthesized as a 115 amino acid precursor, processed by the endoplasmic reticulum/Golgi apparatus, and secreted as an 84 amino acid peptide (hereinafter referred to as 84 amino acid PTH SEQ ID NO:1). Further proteolysis in the serum and tissue results in a peptide of 34–36 amino acids in length. The 34 amino acid peptide has nearly full biological activity (see Potts et al., 1971, *Proc. Natl. Acad. Sci. USA* 68: 63–67; and Treager et al., 1973, *Endocrinology* 93: 1349–1353). The sequence of this 34 amino acid truncated human PTH peptide, hereinafter referred to as simply as "human PTH," shown in one-letter standard abbreviation, from amino-to-carboxy terminus, is: SVSEIQLMHNLGKHLNSMERVEWLRKKLQDVHNF (SEQ ID NO:2).

The amino terminal serine is necessary for complete activity of human PTH. Serial deletion of residues from the amino terminus of the PTH peptide apparently leads to dramatic decreases in the resulting PTH analogs' abilities to activate the PTH receptor, as measured by the change in intracellular cAMP concentration (see Takano et al., 1988, *Acta Endo.* 118: 551–558; and Gardella et al., 1991, *J.Biol. Chem.* 266: 13141–13146). The amino terminal residue appears to play a major role in activation of the PTH receptor, and substitutions of amino acids at positions 2 and 4 (V and E) have been reported to decrease receptor binding of the resulting analogs. The truncated peptides, as well as those with substitutions at positions 2 and 4, have been reported to display significant antagonist activity (see Goldman et al., 1988, *Endocrinology* 123: 1468–1475). Position 3 (S) analogs have been reported to display reduced biological activity in direct proportion to the volume of the side chain of the amino acid substituted for serine at this position (see Cohen et al., 1991, *J. Biol. Chem.* 266: 1997–2004). Deamination of the amino terminal alanine in bovine PTH has been reported to reduce the capacity of the resulting PTH analog peptide to stimulate adenylate cyclase activity (see Goltzmann et al., 1978, *Endocrinology* 103: 1352–1360; and Goltzmann et al., 1975, *J. Biol. Chem.* 250: 3199–3203). PCT patent publication No. 92/00753 describes PTH analogs modified at positions 3, 6, and 9, and other PTH analogs are described in European patent publication No. 301,484.

Oxidation of either methionine at positions 8 and 18 has been reported to lead to decreased bio-potency, and oxidation of both residues has been reported to have a cumulative effect (see Tashjian et al., 1964, *Biochemistry* 3: 1175–1182; Frelinger and Zull, 1984, *J. Biol. Chem.* 259: 5507–5513; and Frelinger and Zull, 1986, *Arch. Biochem. Biophys.* 244: 641–649). Oxidation of the methionines apparently leads to structural changes in the peptide that may account for the decrease in binding affinity associated with these changes (see Zull et al., 1990, *J. Biol. Chem.* 265: 5671–5676). To circumvent the problems associated with oxidation of the methionines, a number of groups have synthesized PTH analogs containing norleucine as a replacement for methionine. The PTH analog 8,18-norleucine-34-tyrosinamide was initially synthesized to provide a sulfur free analog that could be iodinated and would retain biological activity (see Rosenblatt et al., 1976, *J. Biol. Chem.* 251: 159–164, and Segre et al., 1979, *J. Biol. Chem.* 254: 6980–6986). This analog appears to stimulate adenylate cyclase and to have similar binding affinity as the 34 and 84 amino acid bovine PTH molecules.

Very little work has been done on analyzing the structure and function relationships of the amino acids in the middle region of the PTH peptide. Modifications at position 12, a residue predicted to participate in a beta-turn, are reportedly well tolerated, suggesting that this residue does not play a crucial role in the stimulation of adenylate cyclase activity (see Chorev et al., 1990, *Biochemistry* 29: 1580–1586). Deletion of lysine 13, however, may significantly alter the structure of the peptide, because the resulting analog has been reported to retain only slight biological activity (see Zull et al., 1987, *Mol. Cell. Endo.* 51: 267–271).

Modifications of the carboxy terminus of PTH have been reported to have only a modest effect on receptor binding and activation of adenylate cyclase. Serial deletion of the amino acids at the carboxy terminus from position 34 apparently results in a gradual decline in biological activity of the resulting PTH analogs. Removal of 6 amino acids at the carboxy terminus has been reported to result in complete inactivation of the peptide (see Rosenblatt, 1981, *Pathobiology Annual* 11:53–86). Extension of the C-terminus from position 34 to position 38 similarly leads to a decrease in biological activity, presumably by a reduction in the receptor affinities of the resulting PTH analogs (see Goldman et al., supra). Although the carboxy terminus does not appear to play a role in activation of adenylate cyclase, recent evidence suggests that this region of PTH functions in the activation of protein kinase-C (PKC) and protein kinase-A (PKA). The PKC activation domain appears to be localized within the region defined by amino acid positions 28–34 of human PTH, and PKC activation is seen even in PTH analogs lacking the amino terminal residues of PTH (Jouishomme et al., 1992, *Endocrinology* 130: 53–60; and Fujimori et al., 1992, *Endocrinology* 130: 29–36).

Small proteins such as PTH can be difficult to express and recover by recombinant DNA methodology, especially when the host cell is a microorganism such as *E. coli*. To overcome this problem, some groups have designed recombinant DNA expression vectors that encode PTH fusion proteins. Gardella et al., 1990, *J. Biol. Chem.* 265: 15854–15859, reports the expression of the 84 amino acid human PTH as a Factor Xa cleavable fusion partner to human growth hormone and the recovery of about 1.5 to 3 mg/L of PTH after Factor Xa cleavage. Kareem et al., 1992, *Analyt. Biochem.* 204: 26–33, describes similar results using Protein A as a fusion partner. Others have expressed recombinant PTH in yeast (see Olstad et al., 1992, *Eur. J. Biochem.* 205: 311–319, and Gautvik et al., U.S. Pat. No. 5,010,010) as a fusion to yeast mating factor. This expression system results in the secretion of the PTH into the media, but the secreted PTH fusion protein is O-glycosylated.

The yield of PTH from these various methods is low. Purification of the PTH produced by these methods is difficult, resulting in significant losses of the small amount of the peptide that is produced. See PCT patent publication No. 90/10067. Some have tried to improve the production of PTH in *E. coli* host cells by using modified gene sequences in the expression vectors. In one attempt, adenine rich codons were used for the first five amino terminal residues and *E. coli*-favored codons for the rest of the synthetic gene encoding the 84 amino acid PTH. Although expression levels up to 20 mg/L of the 84 amino acid PTH were reported (see PCT patent publication No. 91/05050 and Sung et al., 1991, *J. Biol. Chem.* 266:2831–2835), a major contaminant corresponding to the 8–84 fragment produced by proteolysis in the bacterium was also present. After purification by cation exchange chromatography and HPLC, only about 15% (~6 mg) of the original 84 amino acid PTH was recovered. See also EPO publication No. 483,509, which describes a recombinant system for producing the 84 amino acid PTH.

The difficulty of economically producing PTH or its receptor presents a major obstacle to the development of PTH as a therapeutic agent. In addition, the serum instability of the peptide greatly limits the potential therapeutic effectiveness of human PTH. For these reasons it would be desirable to provide PTH analogs with greater specific activity, improved serum stability, and/or enhanced transport.

Both PTH and parathyroid hormone-related peptide (PTH-PTHrP), which shares 8 of 13 $NH_2$-terminal residues with PTH and causes the hypercalcemia of malignancy syndrome, appear to bind to the same approximately 80-kD receptor glycoprotein. The cDNA encoding this receptor has been cloned. See Juppner et al. (1991) *Science* 254:1024–1026, which is incorporated herein by reference. The receptor comprises 585-amino acids and has seven potential membrane-spanning domains and ten hydrophobic regions.

Although others have reported expressing the PTH receptor in cells, in many instances, a smaller and soluble ligand binding segment would be useful. For example, a soluble ligand binding fragment may serve as an antagonist to modulate the effect of PTH ligands. Antagonists which are soluble and smaller than the original receptor will be useful. The physiological bioavailability of small soluble antagonists will be better than the natural intact receptor. The intact receptor is a membrane bound protein and would typically not circulate in the blood. Soluble antagonist fragments, e.g., which are shorter than the native receptor binding site, will typically also be produced in greater quantities at lower cost. Moreover, a smaller soluble peptide is more likely to be capable of reaching remote and circulation compromised regions of the body.

The patent literature is replete with publications describing the recombinant expression of receptor proteins. See, e.g., PCT patent publication No. 91/18982 and U.S. Pat. Nos. 5,081,228 and 4,968,607, which describe recombinant DNA molecules encoding the IL-1 receptor; U.S. Pat. Nos. 4,816,565; 4,578,335; and 4,845,198, which describe recombinant DNA and proteins relating to the IL-2 receptor; PCT patent publication No. 91/08214, which describes EGF receptor gene related nucleic acids; PCT patent publication No. 91/16431 and U.S. Pat. No. 4,897,264, which describe the interferon gamma receptor and related proteins and nucleic acids; European Patent Office (EPO) publication No. 377,489, which describes the C5a receptor protein; PCT patent publication No. 90/08822, which describes the EPO receptor and related nucleic acids; and PCT patent publication No. 92/01715, which describes MHC receptors.

Several of the above publications not only describe how to isolate a particular receptor protein (or the gene encoding the protein) but also describe variants of the receptor that may be useful in ways the natural or native receptor is not. For instance, PCT patent publication No. 91/16431 describes soluble versions of the gamma interferon receptor, while PCT patent publication No. 92/01715 describes how to produce soluble cell-surface dimeric proteins. This latter technology involves expression of the receptor with a signal for lipid attachment; once the lipid is attached to the receptor, the receptor becomes anchored in the cell membrane, where the dimeric form of the receptor is assembled. PCT patent publication No. 89/01041 describes similar technology, exemplifying how a polypeptide comprising a phospholipid anchor domain can be expressed and attached to the surface of a recombinant host cell.

Thus, a need exists for a highly efficient means for producing a purified ligand binding region, and for soluble molecules which have PTH binding activity. Fragments smaller than the intact extracellular region of the receptor are desired. Economical and high efficiency production of PTH ligand binding proteins, e.g., fragments containing critical ligand binding regions, is greatly desired. The present invention provides these and other needs.

SUMMARY OF THE INVENTION

The present invention provides novel PTH analogs with enhanced activity, longer serum half-life, and/or enhanced iontophoretic transdermal transport than human PTH. The invention also provides recombinant DNA expression vectors and methods for producing these novel PTH analogs at higher levels than currently possible for human PTH and for producing a soluble form of the PTH receptor.

BRIEF DESCRIPTION OF THE DRAWINGS

FIG. 3 provides illustrative sequence information regarding a TrpLE construct (SEQ ID NO:8) and the encoded protein (SEQ ID NO:9).

DETAILED DESCRIPTION OF THE INVENTION

Contents

Figure 1:
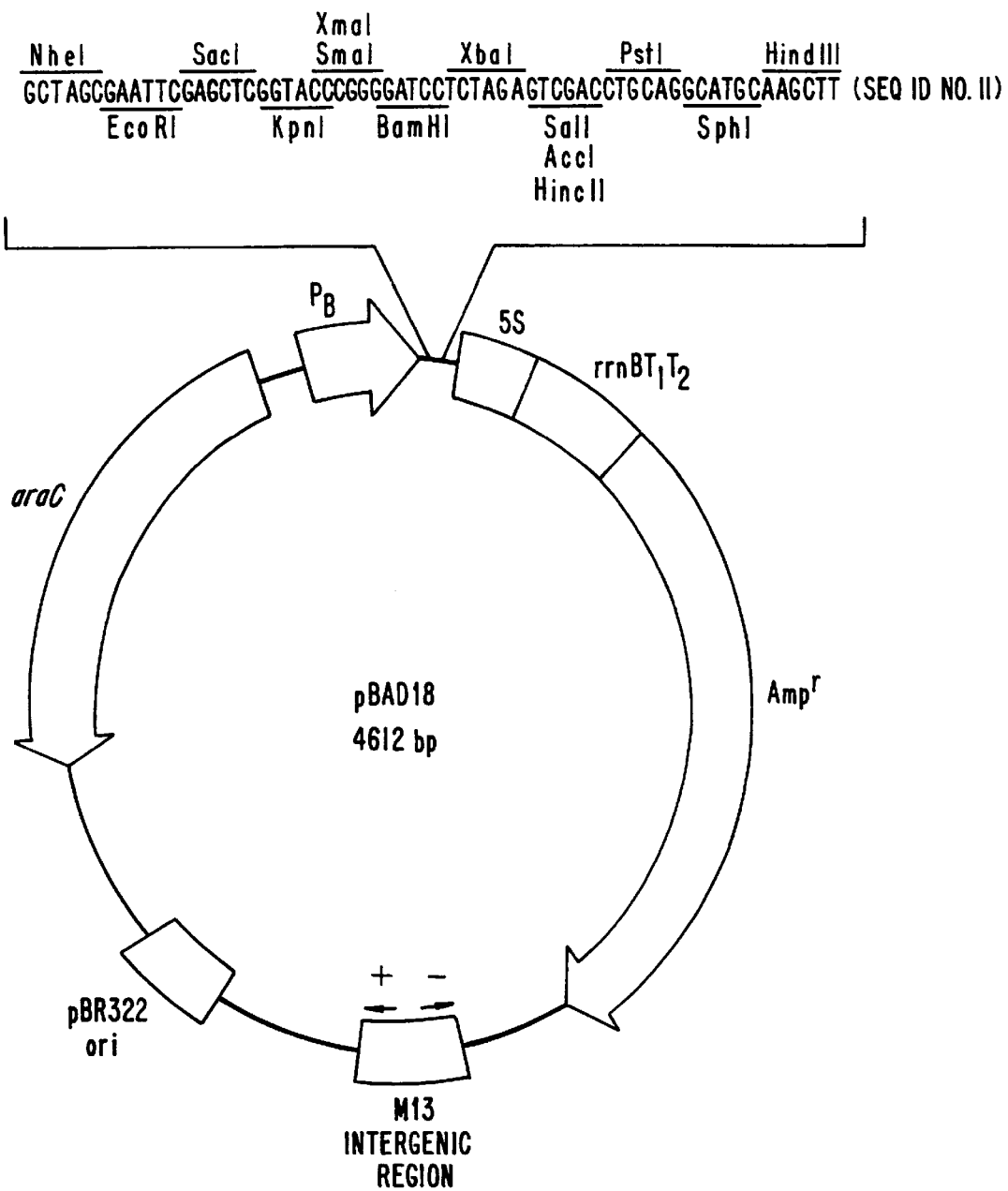
FIG. 1 provides a restriction site and function map of plasmid pBAD18.

I. Terminology
II. Preparation of PTH Analogs
A. Large Scale Production
B. Methods for Rapid Synthesis and Purification
C. Synthetic Techniques 1. General
2. Terminal Modifications
3. Side Chain Modification III. Compositions of PTH Analogs A. Overview
B. Iontophoretic Delivery
C. Topical Treatments
D. Transmucosal Delivery
  1. General
  2. Buccal/Sublingual Administration
  3. Nasal/Pulmonary Administration
  4. Other Membranes
E. Oral Delivery IV. In Vitro Testing of PTH Analogs V. Preparation of Soluble PTH Receptor I. Terminology The following terms are intended to have the following general meanings:

Amino acid residues in peptides are abbreviated as follows: Phenylalanine is Phe or F; Leucine is Leu or L; Isoleucine is Ile or I; Methionine is Met or M; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; and Glycine is Gly or G.

"Amide" or "amido" refers to the group —(CO)NH$_m$R$_n$, where R is hydrogen, alkyl, aryl, arylalkyl, or heteroaryl and where m=0–2, n=0–2, and n+m=2. Preferably, alkyl groups will have from 1–6 carbons, which optionally may be substituted. Preferred aryl groups include phenyl, 1-naphthyl, and 2-naphthyl, which optionally may be substituted. A particularly preferred arylalkyl group is benzyl, which optionally may be substituted.

"Enhanced transdermal delivery" as used herein refers both to the facilitation of transdermal delivery and an absolute increase in the molar volume transported per unit time through a constant surface area utilizing an equimolar pool of transported material as compared to unenhanced transdermal delivery.

"Fusion protein" refers to a fused protein comprising PTH or a fragment thereof or PTH-receptor or a fragment thereof linked at its N-terminus, optionally via a "selective cleavage site", to an additional amino acid sequence. The linkage in the fusion protein is typically via conventional peptide bonds.

"Host Cell" refers to a eukaryotic or procaryotic cell or group of cells that can be or has been transformed by a recombinant DNA vector. For purposes of the present invention, procaryotic host cells are preferred.

"Iontophoresis" or "iontophoretic" refers to the introduction of an ionizable chemical through skin or mucous membranes by the application of an electric field to the interface between the ionizable chemical compound and the skin or mucous membrane.

"Ligand binding region" or (LBR) refers to a segment of the PTH receptor whose presence significantly affects ligand binding, e.g., absolute affinity and specificity. Affinity will usually be affected by a factor of at least about two, typically by a least a factor of about four, more typically by at least a factor of about eight, and preferably by at least about a factor of twelve or more. Measures for specificity are more difficult to quantitate, but will typically be evaluated by comparison to comparative affinity to ligands exhibiting similar structural features. Ligand binding regions are defined, in part, by their effect on the affinity or specificity of binding to PTH ligands. The natural, native full length PTH-R binds PTH (1–34) with a Kd of about 0.5 nM in native opossom kidney cells. See, e.g., Juppner et al. (1991) *Science* 254:1024–1026, which is hereby incorporated herein by reference.

"Peptide" or "polypeptide" refers to a polymer in which the monomers are alpha amino acids joined together through amide bonds. Peptides are two or often more amino acid monomers long.

"Permeability" refers to the ability of an agent or substance to penetrate, pervade, or diffuse through a barrier, membrane, or a skin layer.

"Pharmaceutically acceptable salts" refers to the non-toxic alkali metal, alkaline earth metal, and ammonium salts commonly used in the pharmaceutical industry including the sodium, potassium, lithium, calcium, magnesium, barium, ammonium, and protamine zinc salts, which are prepared by methods well known in the art. The term also includes non-toxic acid addition salts, which are generally prepared by reacting the compounds of this invention with a suitable organic or inorganic acid. Representative salts include the hydrochloride, hydrobromide, sulfate, bisulfate, acetate, oxalate, valerate, oleate, laurate, borate, benzoate, lactate, phosphate, tosylate, citrate, maleate, fumarate, succinate, tartrate, napsylate, and the like.

"Pharmaceutically or therapeutically effective dose or amount" refers to a dosage level sufficient to induce a desired biological result. That result can be transdermal delivery of a pharmaceutical agent, alleviation of the signs, symptoms, or causes of a disease, or any other desired alteration of a biological system.

"Recombinant DNA Cloning or Expression Vector" refers to a DNA or RNA molecule that encodes a useful function and can be used to transform a host cell. For purposes of the present invention, a cloning vector typically serves primarily as an intermediate in the construction of an expression vector; the latter vector is used to transform or transfect a host cell so that the transformed host cell produces a protein or other product encoded by the vector. Such vectors are typically "plasmids," which, for purposes of the present invention, are vectors that can be extrachromosomally maintained in a host cell, but can also be vectors that integrate into the genome of a host cell. Those of skill in the art may refer to "cloning vectors", as defined herein, as "vectors" and to "expression vectors," as defined herein, as "plasmids."

Solubility is usually measured in Svedberg units, which are a measure of the sedimentation velocity of a molecule under particular conditions. The determination of the sedimentation velocity was classically performed in an analytical ultracentrifuge, but is typically now performed in a standard ultracentrifuge. See, Freifelder (1982) *Physical Biochemistry* (2d ed.), W. H. Freeman, and Cantor and Schimmel (1980) *Biophysical Chemistry*, parts 1–3, W. H. Freeman & Co., San Francisco, each of which is hereby incorporated herein by reference. As a crude determination, a sample containing a "soluble" polypeptide is spun in a standard full sized ultracentrifuge at about 50K rpm for about 10 minutes, and soluble molecules will remain in the supernatant. A soluble particle or polypeptide will typically be less than about 30S, more typically less than about 15S, usually less than about 10S, more usually less than about 6S, and, in particular embodiments, preferably less than about 4S, and more preferably less than about 3S.

Solubility of a polypeptide, of course, depends upon the environment and the polypeptide. Many parameters affect polypeptide solubility, including the temperature, the electrolyte environment, the size and molecular characteristics of the polypeptide, and the nature of the solvent. Typically, the temperature at which the polypeptide is used ranges from about 4° C. to about 65° C. Usually the temperature at use is greater than about 18° C. and more usually greater than about 22° C. For diagnostic purposes, the temperature will usually be about room temperature or warmer, but less than the denaturation temperature of components in the assay. For therapeutic purposes, the temperature will usually be body temperature, typically about 37° C. for humans, though under certain situations the temperature may be raised or lowered in situ or in vitro.

"Transdermal delivery" as used herein refers to the transport of substance across the epidermis and dermis, such as the skin, or mucous membranes, where the substance can contact, and be absorbed into, the capillaries. In certain instances, the delivery will be enhanced across other membranes.

II. Preparation of PTH Analogs

A. Large Scale Production

The present invention provides a general method for producing proteins or peptides at high levels in recombinant host cells. For any recombinant protein or peptide expressed at low levels in a recombinant host cell, the present invention provides that one can dramatically increase the level of expression by constructing an expression vector that encodes a fusion protein composed of multiple (2 or more) copies of a methionine-free analog of the protein (the methionine codons in the protein or peptide coding sequence are either deleted or changed into other codons, preferably leucine) and in which each copy is separated from the next copy by at least one methionine residue. The desired protein or peptide monomers, each containing a carboxy-terminal homoserine or homoserine lactone residue, can then be isolated from the fusion protein by cyanogen bromide cleavage. The presence of the homoserine or homoserine lactone at the carboxy-terminus may increase the serum half-life by protecting the peptide or protein from carboxypeptidase.

The invention is exemplified by the high level production of human PTH analogs in *E. coli* host cells. Using the techniques described herein, 500 mg/liter of PTH can be expressed. Other preferred peptides and proteins for purposes of the present invention include ANP (atrial natriuretic peptide), insulinotropin, glucagon, ACTH (adrenocorticotropic hormone), CRF (corticotropin releasing factor), the endorphins, somatostatin, calcitonin, leutenizing hormone releasing hormone, somatotropin, vasopressin, bradykinin, insulin, the interferons ($\alpha$, $\beta$, and $\gamma$), interleukin, erythropoietin, enkephalin (Met and Leu), corticotropin, lipotropin ($\beta$ and $\gamma$), melanocyte-stimulating hormone, epidermal growth hormone, nerve growth factor, chorionic gonadotropin, follicle-stimulating hormone, the interferons, G-CSF, GM-CSF, and GHRF (growth hormone releasing factor).

The present invention also provides novel PTH analogs with increased activities and longer serum half-lives than human PTH. Human PTH is a 34 amino acid peptide, the amino acid sequence of which is shown above. The present PTH analogs differ from human PTH in that the two methionine residues in human PTH (at positions 8 and 18) have been replaced with leucine residues, and the carboxy-terminal phenylalanine residue has been replaced with a tyrosine residue. In addition, two of the analogs contain an additional residue at the carboxy terminus. This additional residue is either homoserine or homoserine lactone. These two analogs are produced as a mixture by one method of the invention. Treatment of the mixture with a methanolic amine forms the corresponding homoserine amide in pure form. See Armstrong (1949) *J. Am. Chem. Soc.* 71:3399–3402.

Thus, the PTH analogs of the invention will be represented herein using one-letter abbreviation for all residues except the homoserine or homoserine lactone, for which the abbreviations "Ho" and "Hol," respectively, are used. The PTH analogs of the invention are shown below (the sequence is shown from amino-to-carboxy terminus):

SVSEIQLLHNLGKHLNSLERVEWLRKKLQDVHNY (SEQ ID NO:3);

SVSEIQLLHNLGKHLNSLERVEWLRKKLQDVHNYHol (SEQ ID NO:4); and

SVSEIQLLHNLGKHLNSLERVEWLRKKLQDVHNYHo (SEQ ID NO:5).

The present invention also provides recombinant DNA expression vectors and methods for producing the PTH analogs of the invention. In one embodiment, the recombinant DNA expression vectors of the invention comprise a nucleic acid that encodes a PTH analog of the invention and a promoter positioned to drive transcription of the PTH analog coding sequence so that the resulting mRNA transcript can be translated by a host cell to produce the PTH analog. This embodiment is preferred for production of the 34 amino acid PTH analog of the invention, which is produced in monomeric form. As described more fully in the Examples below, this monomer can be produced at high levels and then purified easily when produced as a fusion protein with the peptide sequence:

MA(H)$_x$VEM (SEQ ID NO:6)

where x is 4, 5, 6, or more, and the peptide is fused to the amino terminus of the PTH analog. The polyhistidine sequence facilitates purification, and the PTH analog can be isolated from a preparation of the fusion protein by treatment with cyanogen bromide (CNBr), or any other agent that will cleave a peptide or protein selectively at methionine residues, and separation of the cleavage products.

The 35 amino acid, Ho- or Hol-containing PTH analogs of the invention are preferably expressed from similar vectors, except these vectors encode a polymeric form of the PTH analog. The coding sequence in such vectors encodes a fusion protein of sequence:

MA(H)$_x$VE{M(PTH)MVE}$_z$ where (H)$_x$ is as defined above; z is 2, 3, 4, 5, 6, 7, 8, or more; and PTH is the 34 amino acid PTH analog of the invention. Thus, the Ho and Hol residues in the 35 amino acid PTH analogs of the invention are indirectly encoded by a methionine codon. The methionine-containing peptide produced after transcription and translation of the coding sequence can be converted to the Ho- or Hol-containing PTH analog of the invention by treatment with CNBr, resulting in the conversion of the carboxyl-terminal methionine residue to either an Ho or Hol residue. Thus, the present invention also provides a novel nucleic acid that encodes the peptide:

SVSEIQLLHNLGKHLNSLERVEWLRKKLQDVHNYM (SEQ ID NO:7).

As above, the preferred polymeric PTH-encoding recombinant DNA expression vector of the invention also comprises an *E. coli* origin of replication and a selectable marker. The promoter used to drive transcription of the polymeric coding sequence can be any of a wide variety of promoters, including the well known lambda pL, the lac, the trp, and the araB (see U.S. Pat. No. 5,028,530) promoters.

As noted above, in preferred embodiments of the invention, the PTH analog is expressed as a fusion protein with an amino-terminal Met-Ala dipeptide, which, in turn, is linked to a polyhistidine sequence, which, in turn, is linked through a peptide sequence V-E-M to the PTH analog peptide of the invention. Such fusion proteins can be readily purified on, e.g., a nickel chelate column, from which the PTH fusion protein can be released and then cleaved by treatment with CNBr, as described in detail in the Examples below. In similar fashion, when a polymeric PTH analog coding sequence is present in the vector, the Ho/Hol residue is indirectly encoded by a methionine codon, and the coding sequences are joined "head-to-tail," so that the fusion protein produced upon transcription and translation of the coding sequence protein can be cleaved with CNBr to yield the PTH analog of the invention.

B. Methods for Rapid Synthesis and Purification

The present invention also provides a general method for the rapid and efficient production of proteins or peptides in recombinant host cells which is based upon the method described above. More specifically, according to this embodiment, an expression vector (termed TrpLEPTH) encoding a fusion protein composed of 1) a leader peptide sequence that serves to direct the protein into inclusion bodies; 2) the protein or peptide sequence of interest; and 3) optionally, a sequence of about four, five, six, or more histidines that serves as a tag for the purification of the protein on a nickel column is constructed. (SEQ ID NO:8 and SEQ ID NO:9) Similarly to the method described above, this method produces a monomeric subunit of the peptide of interest wherein the peptide is methionine-free and after treatment with cyanogen bromide, has a carboxy-terminal homoserine or homoserine lactone residue at position 35. An example of an TrpLE construct and the encoded protein is shown in FIG. 3.

The invention is exemplified by the production of human PTH analogs in *E. coli* host cells at about 80 mg/liter. Other preferred peptides and proteins whose substitution tolerances can be similarly investigated using the techniques described herein include ANP (atrial natriuretic peptide), insulinotropin, glucagon, ACTH (adrenocorticotropic hormone), CRF (corticotropin releasing factor), the endorphins, somatostatin, calcitonin, leutenizing hormone releasing hormone, somatotropin, vasopressin, bradykinin, insulin, the interferons (α, β, and γ), interleukin, erythropoietin, enkephalin (Met and Leu), corticotropin, lipotropin (β and γ), melanocyte-stimulating hormone, epidermal growth hormone, nerve growth factor, chorionic gonadotropin, follicle-stimulating hormone, the interferons, G-CSF, GM-CSF, and GHRF (growth hormone releasing factor).

Figure 4:
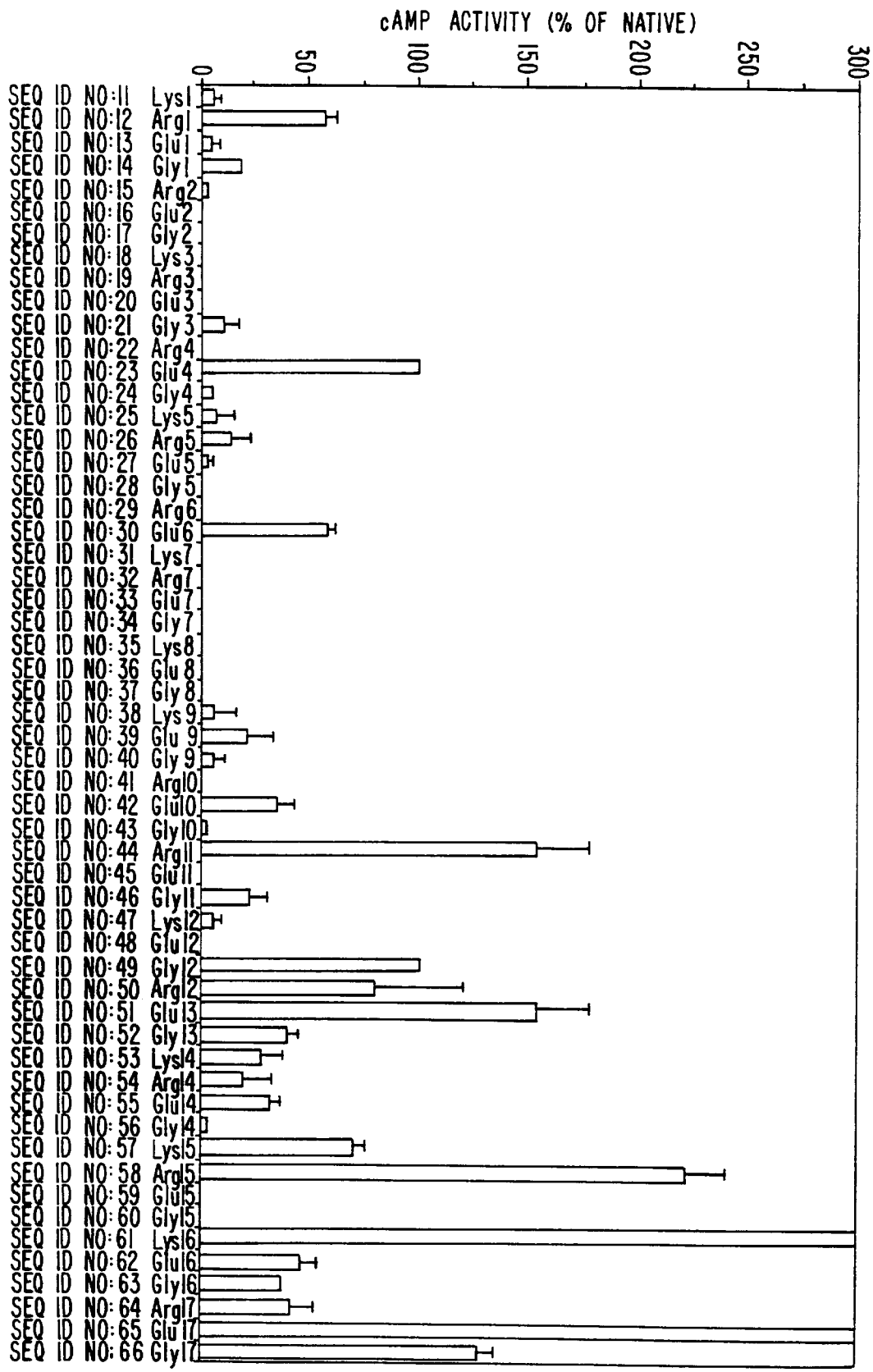
FIGS. 4 and 5 are graphical depictions of cAMP activity (as a percent of native PTH activity) for a variety of PTH analogs. The site and nature of the substitution within each PTH analog is specified along the X-axis.
Figure 5:
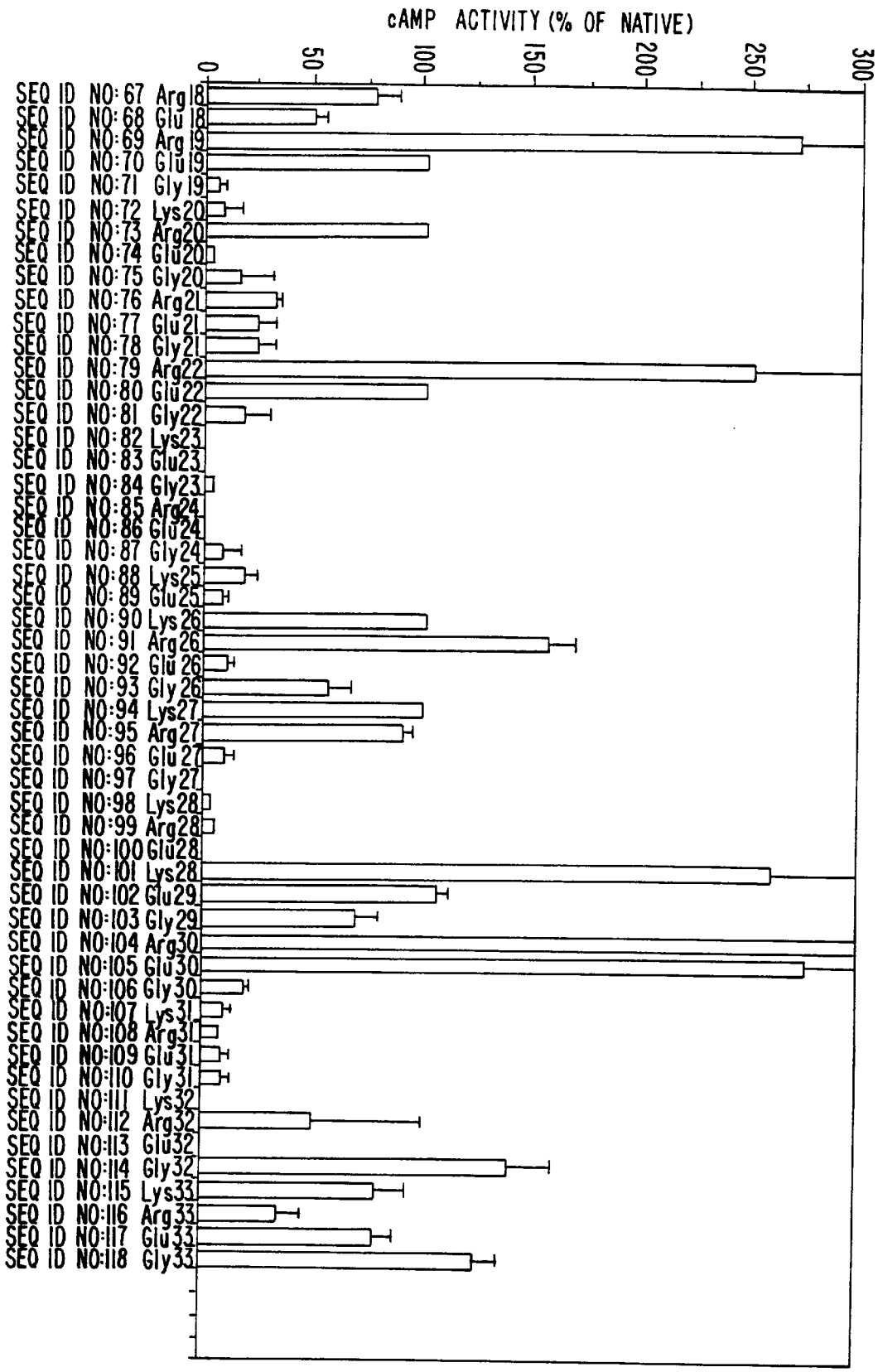

Using the methods described herein, a systematic study of PTH analogs having Lys, Arg, Glu, or Gly substituted at each of positions 1–34 of PTH was conducted. The cAMP activity (as a percent of native PTH activity) for each of these analogs is shown in FIGS. 4 and 5. This study showed that while portions of the PTH molecule are intolerant to substitutions, other sections can be substituted with a neutral, positively charged, and/or negatively charged amino acid such that the PTH analog at least retains and, preferably, exhibits enhanced bioactivity.

Thus, according to one embodiment of this invention, the novel PTH analogs will exhibit enhanced bioactivity compared with PTH itself. Preferably, these PTH analogs will comprise a peptide in substantially pure form in which at least one of the amino acids of PTH is substituted with either a neutral (designated as "0"), positively charged (designated as "+"), or negatively charged (designated as "−") amino acid, following the guidelines shown in Table I below.

TABLE I

Substitution Tolerances for PTH

| Position | Substitution |
|---|---|
| 1–10 | Intolerant |
| 11 | 0, + |
| 12 | 0 |
| 13 | 0, +, − |
| 14 | Intolerant |
| 15 | + |
| 16 | 0, +, − |
| 17 | 0, +, − |
| 18 | 0, +, − |
| 19 | +, − |
| 20–21 | Intolerant |
| 22 | +, − |
| 23–25 | Intolerant |
| 26 | + |
| 27 | + |
| 28 | Intolerant |
| 29 | 0, +, − |
| 30 | 0, +, − |
| 31 | Intolerant |
| 32 | 0, + |
| 33 | 0, +, − |
| 34 | 0, +, − |

Thus, a particularly preferred embodiment of this invention provides for PTH analogs having the amino acid sequence SVSEIQLLHNX$_1$X$_2$X$_3$HX$_4$X$_3$X$_3$X$_3$X$_5$RVX$_5$WLRX$_4$X$_4$LX$_3$X$_3$VX$_1$X$_3$X$_3$X (SEQ ID NO:10) wherein X$_1$ is a neutral or positively charged amino acid, X$_2$ is a neutral amino acid, X$_3$ is a neutral, positively charged, or negatively charged amino acid, X$_4$ is a positively charged amino acid, X$_5$ is a positively charged or negatively charged amino acid, and X is selected from the group consisting of Hol, Ho, a homoserine amide, or the sequence of amino acids comprising residues 35–84 of PTH.

According to the present invention, neutral amino acid refers to an amino acid having a side chain that does not carry a charge, for example, glycine, alanine, valine, leucine, isoleucine, and phenylalanine. Likewise, a positively charged amino acid is an amino acid having a basic side chain, such as an amino group, hydroxyl group, or mercapto group, that is positively charged or capable of carrying a positive charge, including but not limited to, arginine, lysine, hydroxyllysine, histidine, cysteine, tyrosine, and other amino acids, either synthetic or natural having an amino group or other basic functionality on the side chain. A negatively charged amino acid is an amino acid with an acidic side chain, such as a carboxyl group, that is negatively charged or capable of carrying a negative charge, including but not limited to, aspartic acid, glutamic acid, and histidine.

In a particularly preferred embodiment, these PTH analogs, or derivatives thereof, have a higher net ionic charge than native PTH(1–34) and thus, will exhibit enhanced rates of iontophoretic transport. More preferably, the novel PTH analog will be selected from the peptides shown below (the site of substitution, in addition to the substitution at positions 8 and 18, is specified at the beginning of each sequence):

Glu 17—SVSEIQLLHNLGKHLNELERVEWLR-KKLQDVHNYX (SEQ ID NO:65);

Lys 16—SVSEIQLLHNLGKHLKSLERVEWLRKKL-QDVHNYX (SEQ ID NO:61);

Arg 30—SVSEIQLLHNLGKHLNSLERVEWLR-KKLQRVHNYX (SEQ ID NO:104);

Glu 30—SVSEIQLLHNLGKHLNSLERVEWLRKK-LQEVHNYX (SEQ ID NO:105);

Arg 19—SVSEIQLLHNLGKHLNSLRRVEWLRKKL-QDVHNYX (SEQ ID NO:69);

Lys 29—SVSEIQLLHNLGKHLNSLERVEWLRKK-LKDVHNYX (SEQ ID NO:101);

Arg 22—SVSEIQLLHNLGKHLNSLERVRWLRKK-LQDVHNYX (SEQ ID NO:79);

Arg 15—SVSEIQLLHNLGKHRNSLERVEWLRKKL-QDVHNYX (SEQ ID NO:58);

Arg 26—SVSEIQLLHNLGKHLNSLERVEWLRRKL-QDVHNYX (SEQ ID NO:91);

Arg 11—SVSEIQLLHNRGKHLNSLERVEWLRKKL-QDVHNYX (SEQ ID NO:44);

Glu 13—SVSEIQLLHNLGEHLNSLERVEWLRKKL-QDVHNYX (SEQ ID NO:51);

Gly 32—SVSEIQLLHNLGKHLNSLERVEWLRKKL-QDVGNYX (SEQ ID NO:114):

Gly 17—SVSEIQLLHNLGKHLNGLERVEWLRKKL-QDVHNYX (SEQ ID NO:66);

Gly 33—SVSEIQLLHNLGKHLNSLERVEWLRKKL-QDVHGYX (SEQ ID NO:118):

Glu 29—SVSEIQLLHNLGKHLNSLERVEWLRKKL-EDVHNYX (SEQ ID NO:102),

Glu 4—SVSEIQLLHNLGKHLNSLERVEWLRKKL-QDVHNYX (SEQ ID NO:23);

Gly 12—SVSEIQLLHNLGKHLNSLERVEWLRKKL-QDVHNYX (SEQ ID NO:49);

Glu 19—SVSEIQLLHNLGKHLNSLERVEWLRKKL-QDVHNYX (SEQ ID NO:70);

Arg 20—SVSEIQLLHNLGKHLNSLERVEWLRKKL-QDVHNYX (SEQ ID NO:73);

Glu 22—SVSEIQLLHNLGKHLNSLERVEWLRKKL-QDVHNYX (SEQ ID NO:80);

Lys 26—SVSEIQLLHNLGKHLNSLERVEWLRKKL-QDVHNYX (SEQ ID NO:90); and

Lys 27—SVSEIQLLHNLGKHLNSLERVEWLRKKL-QDVHNYX (SEQ ID NO:94), wherein X is selected from the group consisting of Hol, Ho, a homoserine amide, or the sequence of amino acids comprising residues 35–84 of PTH (SEQ ID NO:119).

In some embodiments, the PTH analog will comprise a sequence of amino acids wherein more than one of the amino acids residues have been substituted according to the guidelines set forth in Table I. More specifically, these analogs will possess a combination of two or more of the following single point substitutions, optionally with positions 8 and 18 being independently either Met or Leu:

| Position | Substitution | Position | Substitution |
|---|---|---|---|
| 11 | Arg | 22 | Arg |
| 13 | Glu | 26 | Arg |
| 15 | Arg | 29 | Lys, Glu |
| 16 | Lys | 30 | Arg, Glu |
| 17 | Glu, Gly | 32 | Gly |
| 19 | Arg | 33 | Gly |

For example, particularly preferred PTH analogs will be selected from the peptides shown below:

SVSEIQLLHNLGKHLNELERVEWL-RKKLEDVHNYX (SEQ ID NO:120):

SVSEIQLLHNLGKHRNSLERVRWL-RKKLQDVHNYX (SEQ ID NO:121):

SVSEIQLLHNLGKHRNSLERVEWL-RKKLQRVHNYX (SEQ ID NO:122):

SVSEIQLLHNLGKHLNSLRRVRWL-RKKLQDVHNYX (SEQ ID NO:123): and

SVSEIQLLHNLGKHRNSLRRVRWL-RKKLKDVHNYX (SEQ ID NO:124):

wherein X is selected from the group consisting of Hol, Ho, a homoserine amide, or the sequence of amino acids comprising residues 35–84 of PTH. In other embodiments, the leucine residues at positions 8 and 18 in the peptides described above will be independently replaced with methionine residues.

C. Synthetic Techniques

1. General

The peptides of the invention can also be prepared by classical methods known in the art, for example, by using standard solid phase techniques. The standard methods include exclusive solid phase synthesis, partial solid phase synthesis methods, fragment condensation, and classical solution synthesis (see, e.g., Merrifield, 1963, *J. Am. Chem. Soc.* 85:2149, incorporated herein by reference). On solid phase, the synthesis is typically commenced from the C-terminal end of the peptide using an alpha-amino protected resin. A suitable starting material can be prepared, for instance, by attaching the required alpha-amino acid to a chloromethylated resin, a hydroxymethyl resin, or a benzhydrylamine resin. One such chloromethylated resin is sold under the tradename BIO-BEADS SX-1 by Bio Rad Laboratories, Richmond, Calif, and the preparation of the hydroxymethyl resin is described by Bodonszky et al., 1966, *Chem. Ind.* (London) 38:1597. The benzhydrylamine (BHA) resin has been described by Pietta and Marshall, 1970, *Chem. Commn.* 650, and is commercially available from Beckman Instruments, Inc., Palo Alto, Calif, in the hydrochloride form.

2. Terminal Modifications

A further embodiment of this invention provides for fusion proteins composed of a PTH analog bound to various charged peptides. These fusion proteins can be produced by fusing the cloned gene encoding the PTH analog to a segment that encodes a charged peptide residue containing several charged (positively or negatively) amino acids. These charged peptide "tails" can be rich in lysine, arginine and/or histidine. According to a preferred embodiment, a lysine tail typically composed of about 5–20, and preferably about 5–10, lysine groups, is attached to the C-terminus of the analog.

A further method for C-terminus modification exploits the action of enzymes, and more particularly esterases, i.e., hydrolases that convert an ester into an acid residue and an alcohol residue. Specifically, the PTH analog (i.e., the acid residue) is contacted with an esterase, such as cholinesterase, and a large excess of an alcohol, and preferably an alcohol capable of carrying a charge, such as choline. A large excess of the alcohol is utilized to drive the equilibrium towards ester formation, thus incorporating the charged alcohol residue. This net increase in charge serves to enhance the iontophoretic transport rate of the PTH analog.

More generally, this method will be applicable with any enzyme capable of post-translational modification of a protein and can result in either the introduction of positive charge or the deletion of negative charge. Examples of these enzymes include, but are not limited to, those enzymes responsible for the following amino acid modifications: hydroxylation of proline and lysine residues to form hydroxylproline and hydroxylysine; phosphorylation of serine to phosphoserine, carboxylation of glutamate to gamma-carboxyglutamte; the introduction of amide groups to C-terminal residues, e.g., glycinamide; the methylation, acetylation or phosphorylation of the ε-amino group of lysine; glycoslyation; and the attachment of prosthetic groups, e.g., the attachment of carbohydrates to glycoproteins.

In addition, the amino terminus of the PTH analog can be modified, for example by methylating (i.e., —NHCH$_3$ or —N(CH$_3$)$_2$), acetylating, adding a carbobenzoyl group, or blocking the amino terminus with any blocking group having a carboxylate functionality defined by RCOO—, wherein R is selected from the group consisting of naphthyl, acridinyl, steroidyl, and similar groups. Carboxy terminus modifications include replacing the free acid with a carboxamide group or forming a cyclic lactam at the carboxy terminus to introduce structural constraints. In addition, when the methods described above are utilized to produce a mixture of PTH analogs having a homoserine and homoserine lactone at the C-terminus, the corresponding homoserine amide can be produced via treatment of the mixture with an alcoholic amine. One can also cyclize the peptides of the invention, or incorporate a desamino or descarboxy residue at the terminii of the peptide, so that there is no terminal amino or carboxyl group, to decrease susceptibility to proteases or to restrict the conformation of the peptide. C-terminal functional groups include amide, amide lower alkyl, amide di(lower alkyl), lower alkoxy, hydroxy, and carboxy, and the lower ester derivatives thereof, and the pharmaceutically acceptable salts thereof.

According to some embodiments, either or both of the peptide's terminii will be covalently coupled to a charged chemical modifier. For purposes of the present invention, "chemical modifier" refers to either a permanently charged compound or a compound that carries an ionic charge by virtue of the conditions of pH which exist during delivery of the PTH analog. Although chemical modifiers function primarily to alter the charge characteristics of a pharmaceutical agent, they also can serve to modify the solubility parameters of the PTH analog. For example, several chemical modifiers can be coupled simultaneously to the PTH analog to produce a complex having the same net charge as the analog, but exhibiting different water or lipid solubility due to the introduction of the additional hydrophilic or lipophilic groups of the chemical modifiers. Examples of chemical modifiers include, but are not limited to, carnitine and homologs thereof, lysine and N-methylated derivatives thereof, ornithine, betaine, betonicine, stachydrine, trigonelline, histones, lysine rich proteins, cytochrome c, aminosteroids, amino acids, sulfates, and phosphates. In a particularly preferred embodiment, cytochrome c will serve as the chemical modifier.

3. Side Chain Modification

The side chain functionality of many of the amino acids of the PTH analogs also can be modified. According to a preferred embodiment, these modifications will entail altering the net charge or the charge distribution of the analog. For example, amino acids having a side chain bearing a hydroxyl group, such as Ser, Thr, or Tyr, can be phosphorylated. This modification results in a charge differential of -2 per hydroxyl group. In addition, as discussed above, the side chain functionality can also be coupled to a charged chemical modifier.

III. Compositions of PTH Analogs

A. Overview

The novel PTH analogs described herein can replace PTH in the treatment of human disease. In particular, the PTH analogs of the invention, either alone or in combination with other drugs, will be used to treat hypocalcemia, osteoporosis, and other metabolic bone diseases. Because the PTH analogs of the invention have enhanced activities, increased serum half-lives, and/or enhanced rates of iontophoretic transdermal transport as compared to human PTH, the present PTH analogs will be preferred over human or other forms of PTH for treatment of disease.

Accordingly, the present invention includes pharmaceutical compositions comprising, as an active ingredient, one or more of the PTH analogs of the invention in association with a pharmaceutical carrier or diluent. The compounds of this invention can be administered by oral, parenteral (intramuscular, intraperitoneal, intravenous (IV), or subcutaneous injection), nasal, vaginal, rectal, transdermal, and preferably iontophoretic transdermal, or sublingual routes of administration and can be formulated in dosage forms appropriate for each route of administration.

According to this invention, a therapeutically or pharmaceutically effective amount of a PTH analog is delivered to a patient in need of such an agent. The compositions and methods described herein can be employed for the prophylactic and/or therapeutic treatments. In therapeutic applications, the compositions are administered to a patient already suffering from a disease, as described above, in an amount sufficient to cure or at least partially arrest the symptoms of the disease and its complications. An amount adequate to accomplish this is defined as "therapeutically effective amount or dose." Amounts effective for this use will depend on the severity and course of the disease, previous therapy, the patient's health status and response to the drugs, and the judgment of the treating physician. For instance, several groups are investigating the effectiveness of subcutaneous administration of 84 amino acid PTH (at 100 μg/kg/day) for treatment of hypocalcemia.

In prophylactic applications, the PTH analog is administered to a patient susceptible to or otherwise at risk of a particular disease. Such an amount is defined to be a "prophylactically effective amount or dose." In this use, the precise amounts again depend on the patient's state of health, weight, and the like.

Once improvement of the patient's conditions has occurred, a maintenance dose can be administered if necessary. Subsequently, the dosage or the frequency of administration, or both, can be reduced, as a function of the symptoms, to a level at which the improved condition is retained. When the symptoms have been alleviated to the desired level, treatment can cease. Patients can, however, require intermittent treatment on a long-term basis upon any recurrence of the disease symptoms.

The dosage of active ingredient in the compositions of this invention may be varied; however, the amount of the active ingredient shall be such that a suitable dosage form is obtained. The selected dosage depends upon the desired therapeutic effect, on the route of administration, and on the duration of the treatment desired. Generally, dosage levels in the range of 0.001 to 100 mg/kg of body weight daily are administered to mammals to obtain effective PTH activity. See, e.g., (1986) *J. Bone Min. Res.* 1:377–381; Reeve in *Osteoporosis* Smith (Ed.) Royal College of Physicians, London (1990), pp. 143–155; and (1993) *J. Clin. Invest.* 91:1138–1149, each of which is incorporated herein by reference.

The PTH analog can be admixed with an acceptable physiological carrier solution, such as water, aqueous alcohols, propylene glycol, and dimethylsulfoxide, to make a composition suitable for dermal contact and iontophoretic delivery. "Acceptable physiological carrier" includes those solutions which do not interfere with the effectiveness or the biological activity of the active ingredients and which are not toxic to the hosts to which it is administered. Well known techniques for choosing appropriate carriers and formulating the proper mixtures are exemplified in Banga et al. supra; Lattin et al. (1991) Ann. N.Y. Acad. Sci., 618:450; and Remington's Pharmaceutical Science, 15th Ed., Mack Publishing Company, Easton, Pa. (1980), which are incorporated herein by reference.

It should, of course, be understood that the PTH analogs of this invention can be used in combination with other agents used in the management of disorders susceptible to treatment with PTH. For example, the PTH analogs described herein can be administered with known treatments for osteoporosis, such as fluoride, estrogen, testosterone, and bisphosphonates, such as etidronate, or calcitonin.

In addition, PTH is an ideal candidate for the prevention and/or reversal of osteoporosis because of its ability to indirectly stimulate osteoblasts via the direct stimulation of osteoblasts. Thus preferably the PTH analog is administered in conjunction with an agent capable of inhibiting prostaglandin synthase and osteoclast stimulation, such as cyclooxygenase inhibitors. Examples of cyclooxygenase inhibitors that are suitable as components in this dual therapy include, but are not limited to, ketorolac tromethamine, amikacin sulfate, gentamicin sulfate, kanamycin sulfate, neomycin sulfate, netilmicin sulfate, paromomycin sulfate, streptomycin sulfate, tobramycin sulfate, interferon alfa-2a, interferon alfa-2b, interferon alfa-2c, interferon alfa-n1, interferon alfa-n3, methotrexate, methotrexate sodium, phenylpropanolamine hydrochloride, pentoxifylline, acebutolol hydrochloride, captopril, enalapril maleate, enalaprilat, niacin, dipyridamole, aspirin, choline salicylate, magnesium salicylate, salicylic acid, salsalate, sodium salicylate, acetaminophen, diclofenac sodium, diflunisal, fenoprofen calcium, ibuprofen, indomethacin sodium trihydrate, ketoprofen, meclofenamate sodium, mefenamic acid, naproxen sodium, phenylbutazone, piroxicam, sulindac, tolmetin sodium, bendroflumethiazide, benzthiazide, chlorothiazide sodium, chlorthalidone, cyclothiazide, hydrochlorothiazide, hydroflumethiazide, methylclothiazicde, metolazone, polythiazide, quinethazone, trichlormethiazide, bumetanide, furosemide, flurbiprofen sodium, mesalamine, misoprostol, aurothioglucose, gold sodium thiomalate, chlorpropamide, disulfiram, and the like.

B. Iontophoretic Delivery

The PTH analogs described herein can be administered transdermally using iontophoresis. This form of administration typically involves the delivery of a pharmaceutical agent for percutaneous passage of the drug into the systemic circulation of the patient. However, the therapeutic compositions of a PTH analog described herein also can be delivered directly to pathological or diseased tissue using iontophoresis for the local administration of the analog. The skin sites include anatomic regions for transdermally administering the drug as represented by the forearm, abdomen, chest, back, buttock, mastoidal area and the like.

The therapeutic composition can be delivered by a standard iontophoretic device. In general, iontophoresis is an introduction, by means of electric current, of ions of soluble salts into the tissues of the body. More specifically, iontophoresis is a process and technique which involves the transfer of ionic (charged) species into a tissue (for example through the skin of a patient) by the passage of a electric current through an electrolyte solution containing ionic molecules to be delivered (or precursors for those ions), upon application of an appropriate electrode polarity. That is, ions are transferred into the tissue, from an electrolyte reservoir, by application of electromotive force to the electrolyte reservoir. In iontophoretic systems, the rate of release is primarily controlled by the voltage or current.

A wide variety of iontophoresis devices are presently known. See, e.g., Phipps et al. U.S. Pat. No. 4,744,788; Phipps et al. U.S. Pat. No. 4,747,819; Tapper et al. European Patent Application Publication No. 0318776; Jacobsen et al. European Patent Application Publication No. 0299631; Petelenz et al. U.S. Pat. No. 4,752,285; Sanderson et al. U.S. Pat. No. 4,722,726; Phipps et al. U.S. Pat. No. 5,125,894; and Parsi U.S. Pat. No. 4,731,049, Badzinski et al. (1993) U.S. Pat. No. 5,207,752; Gyory et al. (1993) U.S. Pat. No. 5,203,768; Gyory et al. (1992) U.S. Pat. No. 5,162,042; Phipps (1992) PCT Publication No. WO 92/17239; Landrau et al. (1992) PCT Publication No. WO 92/15365; Gyory et al. (1992) Canadian Patent Publication 2,042,994; Gyory et al. (1992) U.S. Pat. No. 5,158,537; Gyory et al. (1992) PCT Publication No. WO 92/07618; Myers et al. (1992) U.S. Pat. No. 5,147,297; Gyory et al. (1992) U.S. Pat. No. 5,147,297; Gyory et al. (1991) Canadian Patent Publication No. 2,015, 597; Gyory et al. (1992) U.S. Pat. No. 5,084,006; Gyory et al. U.S. Pat. No. 5,162,043; Haak et al. (1992) U.S. Pat. No. 5,167,616; Gyory et al. (1990) PCT Publication No. 90/09413; Theeuwes et al. (1992) U.S. Pat. No. 5,080,646; Theeuwes et al. (1992) U.S. Pat. No. 5,147,296; Theeuwes et al. (1992) U.S. Pat. No. 5,169,382; Theeuwes et al. (1992) U.S. Pat. No. 5,169,383; Theeuwes (1990) U.S. Pat. No. 4,978,337; Moodie et al. (1992) U.S. Pat. No. 5,125,894; Haak et al. (1990) U.S. Pat. No. 4,927,408; and Chien et al. (1991) U.S. Pat. No. 5,042,975; the full disclosures of each which are incorporated herein by reference.

In typical, conventional, electrotransport or iontophoresis devices, two electrodes are generally used. Both electrodes are disposed so as to be in intimate electrical contact with some portion (typically skin) of the subject (human or animal) typically by means of two remote electrolyte-containing reservoirs, between which current passes as it moves between the skin and the electrodes. Generally the active electrode includes the therapeutic species as a charged ion, or a precursor for the charged ion, and the transport occurs through application of the electromotive force to the charged therapeutic species.

An appropriate potential is initiated between two electrode systems (anode and cathode) in electrical contact with the skin. If a positively charged drug is to be delivered through the skin, an appropriate electromotive force can be generated by orienting the positively charged drug species at a reservoir associated with the anode. Similarly, if the ion to be transferred across the skin is negatively charged, appropriate electromotive force can be generated by positioning the drug in a reservoir at the cathode. Of course, a single system can be utilized to transfer both positively charged and negatively charged drugs into a patient at a given time; and, more than one cathodic drug and/or more than one anodic drug may be delivered from a single system during a selected operation.

In conjunction with the patient's skin in electrical communication with the electrodes, the circuit is completed by connection of the two electrodes to a source of electrical energy as a direct current; for example, a battery or a source of appropriately modified alternating current. For general discussions of iontophoresis, see, e.g., Tyle (1989) *J. Pharm. Sci.* 75:318; Burnette, Iontophoresis (Chapter 11) in *Transdermal Drug Delivery* Hadgraft and Guy (eds.) Marcel Dekker, Inc.: New York, N.Y.; Phipps et al. (1988) *Solid State Ionics* 28–30:1778–1783; Phipps et al. (1989) *J.*

*Pharm. Sciences* 78:365–369; and Chien et al. (1988) *J. Controlled Release* 7:1–24, the full disclosures of which are incorporated herein by reference.

In typical, conventional, electrotransport devices, for example iontophoresis devices, two electrodes are generally used. Both electrodes are disposed so as to be in intimate electrical contact with some portion (typically skin) of the subject (human or animal) typically by means of two remote electrolyte-containing reservoirs, between which current passes as it moves between the skin and the electrodes. One electrode, generally referred to herein as the "active" electrode, is the electrode from which the PTH analog is delivered or driven into the body by application of the electromotive force. The other electrode, typically referred to as an "indifferent" or "ground" electrode, serves to close the electrical circuit through the body. In some instances both electrodes may be "active", i.e. drugs may be delivered from both. Herein the term electrode, or variants thereof, when used in this context refers to an electrically conductive member, through which a current passes during operation.

A variety of electrode materials, ranging from platinum to silver-silver chloride, are available for these devices. The primary difference in these materials is not in their ability to generate an electric potential across the skin, but rather in certain nuances associated with their performance of this function. For example, platinum electrodes hydrolyze water, thus liberating hydrogen ions and subsequently, changes in pH. Obviously, changes in pH can influence the ionization state of therapeutic agents and their resulting rate of iontophoretic transport. Silver-silver chloride electrodes, on the other hand, do not hydrolyze water. However, these electrodes require the presence of chloride ion which may compete for current-induced transport.

Electrotransport devices generally require a reservoir as a source of the species (or a precursor of such species) which is to be moved or introduced into the body. The reservoir typically will comprise a pool of electrolyte solution, for example an aqueous electrolyte solution or a hydrophilic, electrolyte-containing, gel or gel matrix, semi-solid, foam, or absorbent material. Such pharmaceutical agent reservoirs, when electrically connected to the anode or the cathode of an iontophoresis device, provide a source of one or more ionic species for electrotransport.

Many iontophoresis devices employ a selectively permeable membrane. The composition of this membrane will vary with the particular needs of the system and will depend upon the composition of the electrolyte reservoir, i.e., the nature of the pharmaceutical agent, the transference of current out of the reservoir, and the desired selectivity to transport of particular types of charged and uncharged species. A microporous polymer or hydrogel such as is known in the art can be utilized. See, e.g., U.S. Pat. No. 4,927,408.

Suitable permeable membrane materials can be selected based on the desired degree of permeability, the nature of the PTH analog, and the mechanical considerations related to constructing the device. Exemplary permeable membrane materials include a wide variety of natural and synthetic polymers, such as polydimethylsiloxanes (silicone rubbers), ethylenevinylacetate copolymer (EVA), polyurethanes, polyurethane-polyether copolymers, polyethylenes, polyamides, polyvinylchlorides (PVC), polypropylenes, polycarbonates, polytetrafluoroethylenes (PTFE), cellulosic materials, e.g., cellulose triacetate and cellulose nitrate/acetate, and hydrogels, e.g., 2-hydroxyethylmethacrylate (HEMA).

Generally, buffers will also be incorporated into the reservoir to maintain the reservoir environment at the same charge as the electrode. Typically, to minimize competition for the electric current, a buffer having the opposite charge to the drug will be employed. In some situations, for example, when the appropriate salt is used, the drug may act as its own buffer. Other variables which may effect the rate of transport include drug concentration, buffer concentration, ionic strength, nonaqueous cosolvents, and any other constituents in the formulation. However, as discussed above, to achieve the highest transport efficiency, the concentration of all ionic species, save the pharmaceutical agent itself, is minimized.

The backing or enclosure of the drug delivery system is intended primarily as a mechanical support for the reservoir or matrix. In the simplest case, the matrix is exposed directly to the skin or membrane of the host, and the backing is a strip or patch capable of being secured to the skin, typically with the matrix acting as an adhesive. In such constructions, the backing will usually be impermeable to the PTH analog. This impermeability inhibits the loss of the analog. Suitable backing materials will generally be thin, flexible films or fabrics such as woven and non-woven fabrics and polymeric films, such as polyethylene, polypropylene, and silicone rubber; metal films and foils; and the like.

The delivery device can be held in place with the adhesive of the matrix, with an adhesive along the perimeter of the matrix, with tape or elastic, or any other means, so long as the device allows the pharmaceutical agent to be transported through the skin. The device can be placed on any portion of the skin or dermal surface, such as the arm, abdomen, thigh, and the like. Furthermore, the device can be in various shapes and can consist of one or more complexes and/or transport areas. Other items can be contained in the device, such as other conventional components of therapeutic products, depending upon the desired device characteristics.

In conjunction with the patient's skin in electrical communication with the electrodes, the circuit is completed by connection of the two electrodes to a source of electrical energy as a direct current; for example, a battery or a source of appropriately modified alternating current. As an example, if the ionic substance to be driven to the body is positively charged, then the positive electrode (the anode) will be the active electrode and the negative electrode (the cathode) will serve to complete the circuit. If the ionic substance to be delivered is negatively charged, then the negative electrode (cathode) will be the active electrode and the positive electrode (anode) will be the indifferent electrode.

Chemical enhancers and electroporation can also be utilized to alter the iontophoretic transport rate. For example, the coapplication of oleic acid to the skin causes a large decrease in the skin impedance or resistance which is inversely related to permeability or transport. See Potts et al. (1992) *Solid State Ionics* 53–56:165–169. Thus, instead of the current passing primarily through the shunt pathways (e.g., the follicles and sweat ducts), the ions constituting the current can more uniformly permeate the lipid milieu of the stratum corneum at a lower current density. Thus, the epidermis, as well as the peripheral neurons surrounding the hair follicles and sweat ducts, will be able to experience the electrical stimulation.

In the conventional topical treatment by iontophoresis, the direct current is applied through moist pad-type electrodes with size corresponding to that of the skin region to be treated. The interposition of a moist pad between the electrode plate and the skin is necessary for making a perfect contact, preventing any skin burns, overcoming skin resistance, and protecting the skin from absorbing any caustic metal compounds formed on the metal plate surface.

The drug is administered through an electrode having the same charge as the drug, and a return electrode opposite in charge to the drug is placed at a neutral site on the body surface. The operator then selects a current intensity below the pain threshold level of the patient and allows the current to flow for an appropriate length of time. Ions transferred through the skin are taken up by the micro-circulation at the dermal-epidermal junction, while the current proceeds through the skin tissues to the return electrode. The current intensity should be increased slowly, maintained for the length of time of the treatment, and then decreased slowly at the end of the treatment. The current must be within comfortable toleration of the patient, with a current density which is generally less than 0.5 mAmp/cm$^2$ of the electrode surface.

The therapeutic composition can be delivered by a standard iontophoretic device. Owing to differences in available iontophoretic devices the procedure for use can vary. The manufacturer's instructions should be followed for appropriate pharmaceutical agent delivery. Body fluid or blood levels of the PTH analog can be determined to measure the effectiveness of the transport.

For iontophoretic delivery, the invention provides PTH analogs with a charge-to-mass ratio that allows the PTH analog to be delivered in therapeutically effective amounts. Typically, the charge-to-mass ratio of such a compositions will exceed one charge per 5000 daltons, and more typically, one charge per 2500 daltons. Preferably, the charge-to-mass ratio will be equal to or exceed one charge per 1000 daltons, more preferably, one charge per 500 daltons.

Typically, the iontophoretic carrier solution will also contain other ionic species, in addition to the PTH analog. For example, these ionic species can arise from buffer solutions that may be present to maintain the pH of the solution. As expected from a coulombic mechanism of electrotransport, to achieve the highest transport efficiency, the concentration of all ionic species, save the PTH analog, should be minimized.

In addition to the PTH analog, the composition for iontophoretic delivery can contain other materials such as dyes, pigments, inert fillers, or other permeation enhancers, excipients, and conventional components of pharmaceutical products and transdermal therapeutic systems known in the art. Thus, according to some embodiments of this invention, chemical enhancers (i.e., penetration or permeation enhancers) will be incorporated into the donor reservoir of the iontophoretic device and utilized to alter the iontophoretic transport rate. For example, the coapplication of oleic acid to the skin causes a large decrease in the skin impedance or resistance which is inversely related to permeability or transport. See Potts et al. (1992) *Solid State Ionics* 53–56:165–169. Thus, instead of the current passing primarily through the shunt pathways (e.g., the follicles and sweat ducts), the ions (e.g., the nucleotide-based pharmaceutical agent) constituting the current can more uniformly permeate the lipid milieu of the stratum corneum at a lower current density. Alternatively, the use of chemical enhancers will allow for an increased rate of iontophoretic transport of the nucleotide-based pharmaceutical agent as compared to the transport rate found at the same current density in the absence of the chemical enhancer.

In general, a suitable effective dose of the PTH analog which can be delivered iontophoretically according to the methods described herein will be in an amount ranging from between about 0.1 to about 10 milligram (mg) per recipient per day using an iontophoresis device having a 20 cm$^2$ donor reservoir and a current of less than about 0.5 mAmps/cm$^2$, preferably in the range of between about 0.5 to about 5 mg per day, and most preferably in an amount of about 0.5 to about 1 mg.

C. Topical Treatments

One aspect of this invention provides for the delivery of therapeutic compositions of the PTH analog directly to pathological or diseased tissue. Typically, the topical formulations will comprise a preparation for delivering the PTH analog directly to the affected skin comprising the analog typically in concentrations in the range of from about 0.001% to 10%; preferably, from about 0.01 to about 10%; more preferably, from about 0.1 to about 5%; and most preferably, from about 1 to about 5%, together with a non-toxic, pharmaceutically acceptable topical carrier. See Dermatological Formulations: Percutaneous Absorption, Barry (ed.), Marcel Dekker Inc., (1983).

Topical preparations can be prepared by combining the PTH analog with conventional pharmaceutical diluents and carriers commonly used in topical dry, liquid, cream and aerosol formulations. Ointment and creams may, for example, be formulated with an aqueous or oily base with the addition of suitable thickening and/or gelling agents. Such bases may include water and/or an oil such as liquid paraffin or a vegetable oil such as peanut oil or castor oil. Thickening agents which may be used according to the nature of the base include soft paraffin, aluminum stearate, cetostearyl alcohol, propylene glycol, polyethylene glycols, woolfat, hydrogenated lanolin, beeswax, and the like.

Lotions may be formulated with an aqueous or oily base and will, in general, also include one or more of the following: stabilizing agents, emulsifying agents, dispersing agents, suspending agents, thickening agents, coloring agents, perfumes, and the like.

Powders may be formed with the aid of any suitable powder base, e.g., talc, lactose, starch, and the like. Drops may be formulated with an aqueous base or non-aqueous base also comprising one or more dispersing agents, suspending agents, solubilizing agents, and the like.

Dosage forms for the topical administration of a compound of this invention include powders, sprays, ointments, pastes, creams, lotions, gels, solutions, patches and inhalants. The active compound may be mixed under sterile conditions with a pharmaceutically- acceptable carrier, and with any preservatives, buffers, or propellants which may be required.

The ointments, pastes, creams and gels also may contain excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays also can contain excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

D. Transmucosal Delivery

1. General

Although much of the discussion herein has centered on techniques for transdermal delivery, the methods of the present invention are also applicable to the enhanced transport and delivery of PTH analogs through mucosal membranes, such as buccal, nasal, pulmonary, vaginal, corneal, and ocular membranes. See, e.g., Mackay et al. (1991) *Adv. Drug Del. Rev.* 7:313–338. Specifically, there are many similarities between skin and mucosal membranes. For example, the membrane of the buccal cavity is nonkeratinized. However, the buccal membrane is similar to the skin since the both are stratified with the former consisting of polygonal cells at the basal membrane leading to squamous cells at the surface.

Transmucosal (i.e., sublingual, buccal and vaginal) drug delivery provides for an efficient entry of active substances to systemic circulation and reduce immediate metabolism by the liver and intestinal wall flora. Transmucosal drug dosage forms (e.g., tablet, suppository, ointment, gel, pessary, membrane, and powder) are typically held in contact with the mucosal membrane and disintegrate and/or dissolve rapidly to allow immediate systemic absorption. For instance, a nasal formulation of human PTH is under investigation by several companies for treatment of osteoporosis.

2. Buccal/Sublingual Administration

For delivery to the buccal or sublingual membranes, typically an oral formulation, such as a lozenge, tablet, or capsule will be used. The method of manufacture of these formulations are known in the art, including but not limited to, the addition of the PTH analog to a pre-manufactured tablet; cold compression of an inert filler, a binder, and either the PTH analog or a substance containing the analog (as described in U.S. Pat. No. 4,806,356); and encapsulation. Another oral formulation is one that can be applied with an adhesive, such as the cellulose derivative, hydroxypropyl cellulose, to the oral mucosa, for example as described in U.S. Pat. No. 4,940,587. This buccal adhesive formulation, when applied to the buccal mucosa, allows for controlled release of the PTH analog into the mouth and through the buccal mucosa.

3. Nasal/Pulmonary Administration

For delivery to the nasal or pulmonary membranes, typically an aerosol formulation will be employed. The term "aerosol" includes any gas-borne suspended phase of the PTH analog which is capable of being inhaled into the bronchioles or nasal passages. Specifically, aerosol includes a gas-borne suspension of droplets of the compounds of the instant invention, as may be produced in a metered dose inhaler or nebulizer, or in a mist sprayer. Aerosol also includes a dry powder composition of the PTH analog suspended in air or other carrier gas, which may be delivered by insufflation from an inhaler device, for example.

For solutions used in making aerosols, the preferred range of concentration of the PTH analog is 0.1–100 milligrams (mg)/milliliter (ml), more preferably 0.1–30 mg/ml, and most preferably, 1–10 mg/ml. Usually the solutions are buffered with a physiologically compatible buffer such as phosphate or bicarbonate. The usual pH range is 5 to 9, preferably 6.5 to 7.8, and more preferably 7.0 to 7.6. Typically, sodium chloride is added to adjust the osmolarity to the physiological range, preferably within 10% of isotonic. Formulation of such solutions for creating aerosol inhalants is discussed in Remington's Pharmaceutical Sciences, see also, Ganderton and Jones, *Drug Delivery to the Respiratory Tract*, Ellis Horwood (1987); Gonda (1990) *Critical Reviews in Therapeutic Drug Carrier Systems* 6:273–313; and Raeburn et al. (1992) *J. Pharmacol. Toxicol. Methods* 27:143–159.

Solutions of the PTH analogs may be converted into aerosols by any of the known means routinely used for making aerosol inhalant pharmaceuticals. In general, such methods comprise pressurizing or providing a means of pressurizing a container of the solution, usually with an inert carrier gas, and passing the pressurized gas through a small orifice, thereby pulling droplets of the solution into the mouth and trachea of the animal to which the drug is to be administered. Typically, a mouthpiece is fitted to the outlet of the orifice to facilitate delivery into the mouth and trachea.

4. Other Membranes

Compositions for rectal or vaginal administration are preferably suppositories which may contain, in addition to the active substance, excipients such as cocoa butter or a suppository wax. The compounds described herein also can be delivered via ocular membranes. See, e.g., Mackay et al. (1991) *Adv. Drug Del. Rev.* 7:313–338, which is incorporated herein by reference.

E. Oral Delivery

Solid dosage forms for oral administration include capsules, tablets, pills, powders, and granules. In such solid dosage forms, the active compound is admixed with at least one inert pharmaceutically acceptable carrier such as sucrose, lactose, or starch. Such dosage forms can also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration include pharmaceutically acceptable emulsions, solutions, suspensions, syrups, with the elixirs containing inert diluents commonly used in the art, such as water. Besides such inert diluents, compositions can also include adjuvants, such as wetting agents, emulsifying and suspending agents, and sweetening, flavoring, and perfuming agents. Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

IV. In Vitro Testing of PTH Analogs

Figure 6:
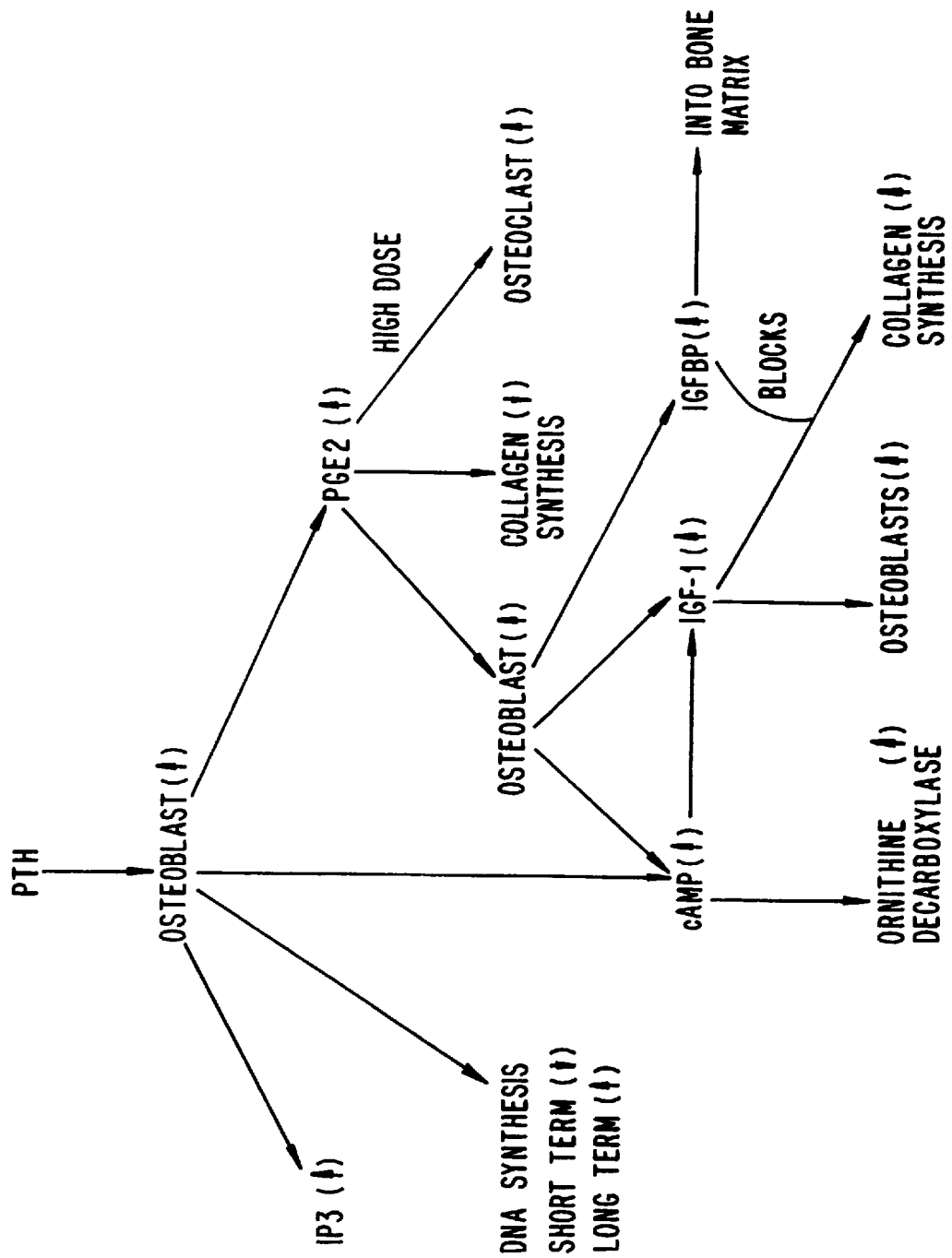
FIG. 6 illustrates the cascade of physiological responses initiated by the action of PTH.

The efficacy of the compounds of the instant invention can be evaluated by either in vitro or in vivo procedures. For example, PTH initiates a cascade of physiological responses as shown in FIG. 6. The levels of any of the subsequent intermediaries can be monitored to assess the efficacy of the PTH analogs described herein. See, e.g., Gardella et al. (1993) *Endocrinology* 132:2024–2030 (for cAMP assay), Fujiomori et al. (1992) *Endocrinology* 130:29–36 (activation of phospholipase-C, protein kinase-A, and protein kinase-C), Jouishomme et al. (1992) *Endocrinology* 130:53–60 (protein kinase-C), Ljunggren et al. (1992) *Bioscience Reports* 12:267 (cAMP and cytoplasmic free calcium ion), Scott et al. (1992) *Molecular Endocrinology* 6:2153–2159 (transcription of collagenase by a mechanism using cyclic adenosine 3',5'-monophosphate and requiring protein synthesis), Pun (1989) *J. Biochem.* 106:1090–1093 (collagen synthesis and cell mitogenesis), Linkhart and Mohan (1989) *Endocrinology* 125:1484–1491 (release of insulin-like growth factor-I and -II), Linkhart and Keffer (1991) *Endocrinology* 128:1511–1518 (release of insulin-like growth factor-I and -II), Abou-Samra et al. (1993) *Endocrinology* 132:801–805 (adrenocorticotropin release), Tada et al. (1990) *Bone* 11:163–169 (axial and appendicular bone volume), Wronski et al. (1993) *Endocrinology* 132:823–831 (bone mass), and Liu and Kalu (1990) *J. Bone Mineral Res.* 5:973 (bone mass), each of which is incorporated herein by reference. In addition, the efficiency of the PTH analogs for the treatment of osteoporosis can be demonstrated by assays well known in the art, for example, the use of cultured osteoblasts of the UMR-106 rat osteosarcoma cells, ATCC CRL 1661. Uptake of calcium in these cells can be monitored using the FURA-2 method, wherein a fluorescent dye which is specific for calcium is used as a marker for calcium change into the cells. This technique is described in Grynkiewicz et al. (1985) *J. Biol. Chem.* 260:3440 and Pang and Shan (1993) PCT Publication No. WO 93/06845, each of which is incorporated herein by reference.

The in vitro skin permeation rate of the PTH analogs can be measured using diffusion cells. Human, mouse or porcine skin is placed on the lower half of the diffusion cell with the stratum corneum facing the donor compartment. The donor compartment contains a solution of the pharmaceutical agent and the cathode. The receiver compartment contains a buffer solution and the anode. An electric current is applied and the amount of transported drug can be calculated ($\mu g/cm^2 \cdot hr$). Alternatively, an iontophoresis device containing the pharmaceutical agent to be tested can be placed on the stratum corneum. The receiver compartment again would contain a buffer solution. The device is activated and the amount of transported drug can be calculated ($\mu g/cm^2 \cdot hr$).

Conventional flow-through diffusion cells can also be used to measure the in vitro skin permeation rate of pharmaceutical agents. Typically these cells will have an active area of 1 $cm^2$ and a receiving volume of 3 ml. The receptor fluid, generally isotonic saline or buffer solution, is pumped into and through the cells, by a peristaltic pump. Samples can be collected in glass vials arranged in an automatic fraction collector. The amount of drug permeating across the skin ($\mu g/cm^2 \cdot hr$) is calculated from the cumulative release.

The electrotransport behavior of a PTH analog can also be assessed using conventional analytical techniques and gel or capillary electrophoresis. Preparation measurements may also be performed one excised skin in conventional diffusion cell test. See, e.g., Laittin et al. supra.

When conducting any in vitro assay related to the transdermal (either passive or iontophoretic) or topical delivery of the PTH analogs described herein, care should be taken to reduce any nonspecific binding of the PTH analog. More specifically, with some analogs it may prove necessary to block nonspecific binding with casein or casein enzymatic hydrolysate, optionally in the presence of detergents. Alternatively, the proteoglycan layer in the skin can be modified or removed through enzymatic treatment of the skin.

V. Preparation of Soluble PTH Receptor

A. General

Figure 8:
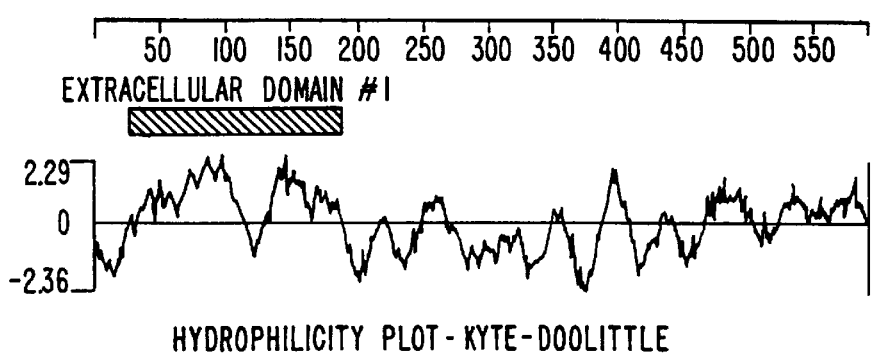
FIG. 8 is a graphical depiction of the hydrophilicity profile of the PTH receptor using a 20-residue window.
Figure 7A:
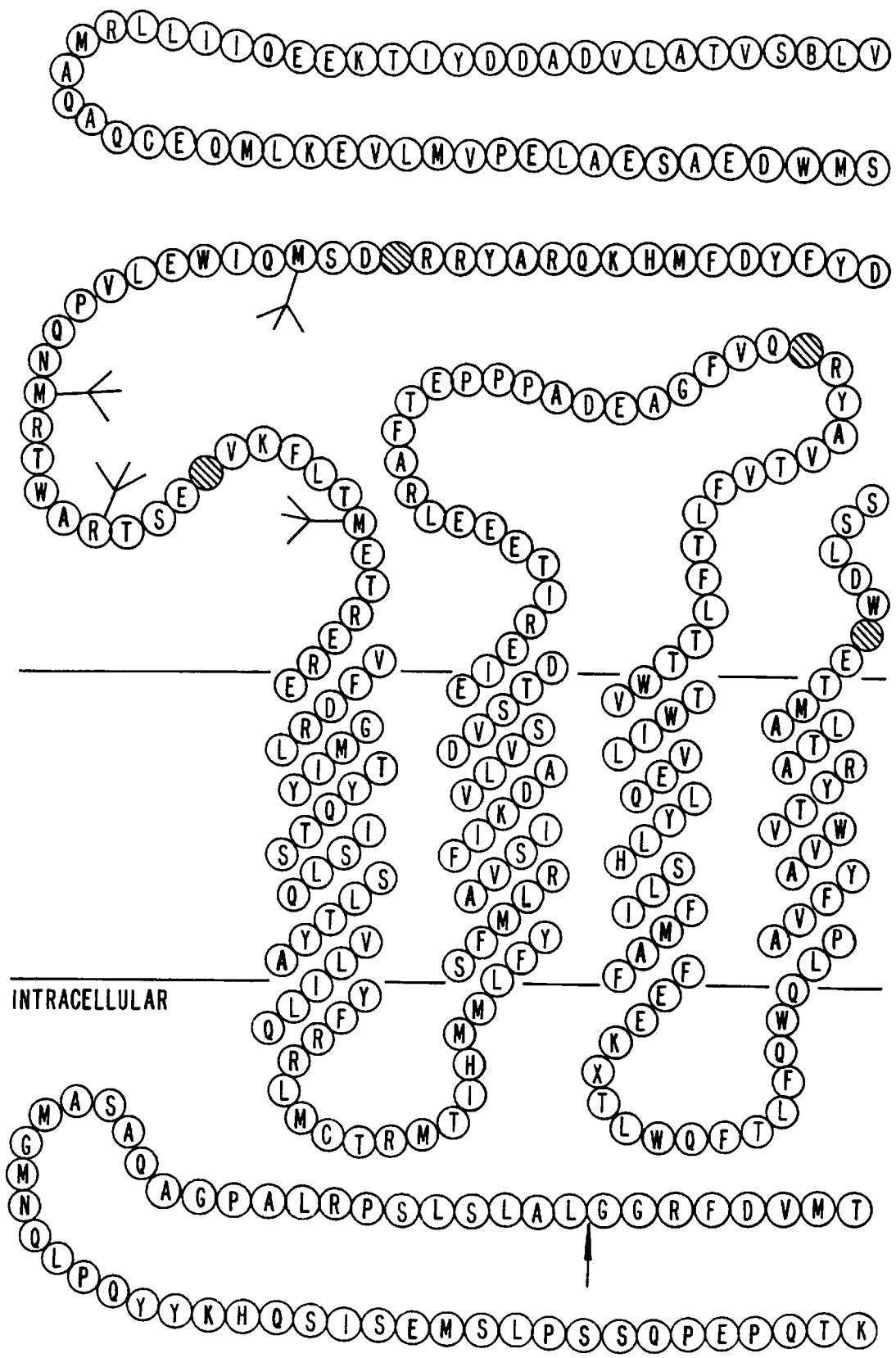
FIG. 7 is a schematic representation of the PTH receptor (SEQ ID NO:125).
Figures 7, 7B:
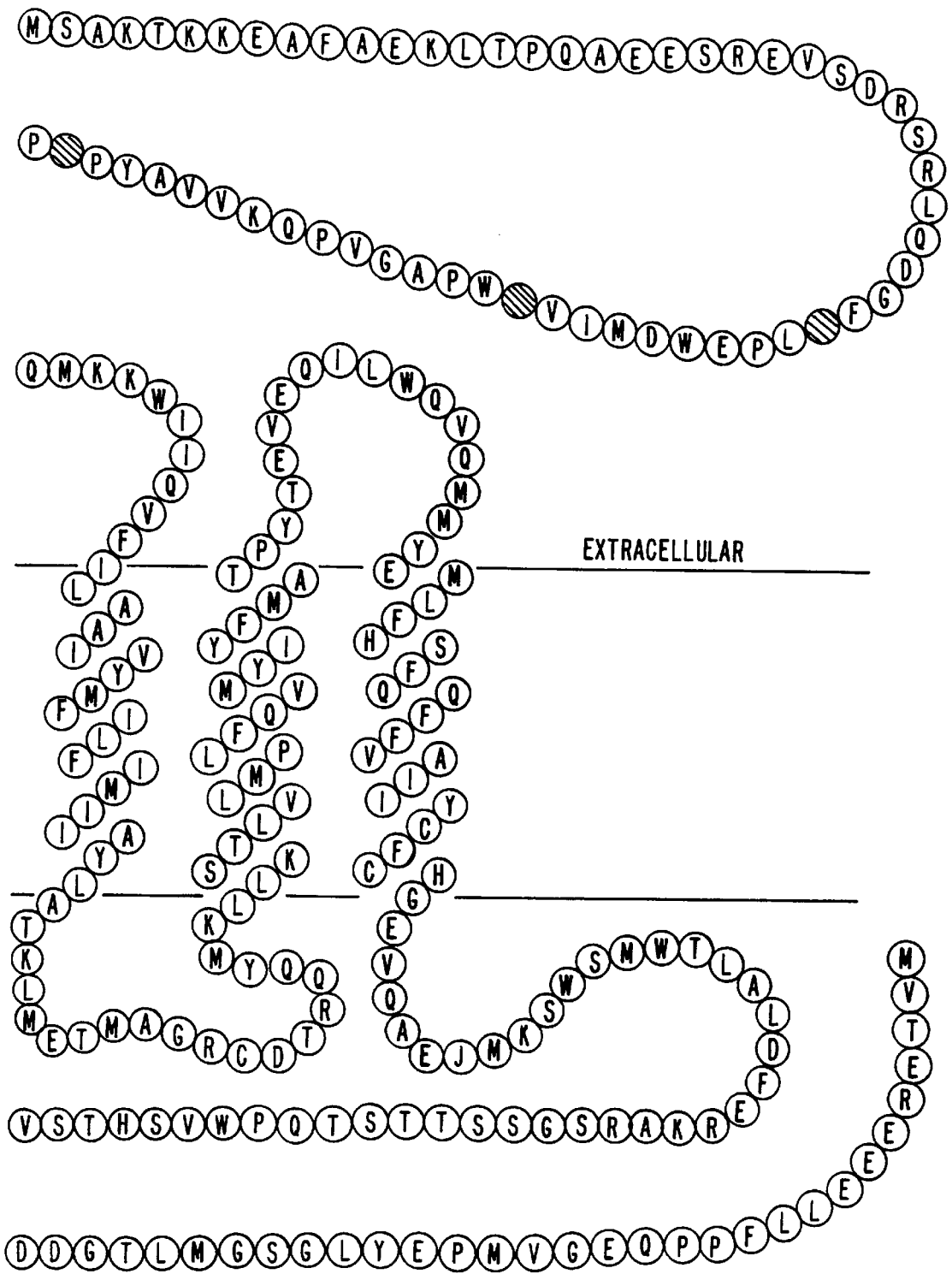

A schematic representation of the PTH receptor is shown in FIG. 7. (SEQ ID NO:125) In addition, FIG. 8 depicts the hydrophilicity profile of the PTH receptor using a 20-residue window. As shown in these figures, the carboxy-terminal transition from the relatively hydrophilic extracellular domain to the adjacent hydrophobic domain is centered on approximately amino acid 188. The present invention also provides methods for producing a soluble form of the PTH receptor, wherein the soluble form comprises the extracellular domain of the receptor and spans approximately amino acid residues 1 to about residue 170–200 of the intact PTH receptor.

B. Fusion Proteins

According to a particularly preferred embodiment, these methods will be used to create a nucleic acid, typically in the form of a recombinant DNA expression vector, that encodes a fusion protein composed of the desired PTH receptor fragment and an anchoring sequence. More specifically, the soluble form of the PTH receptor can be produced using a glycosylphosphatidylinositol (GPI) fusion in which the extracellular domain of the PTH receptor is fused to the carboxy-terminal-most 30–40 amino acid residues of any of a number of GPI-linked proteins. In a particularly preferred embodiment, the GPI-linked protein will be either decay accelerating factor (DAF) or human placental alkaline phosphatase (HPAP). See, e.g., copending U.S. patent application Ser. No. 07/947,339, filed Sep. 18, 1992, Low et al. (1986) *Trends Biochem. Sci.* 11:212–215; Cross (1987) *Cell* 48:179–181, Caras et al. (1987) *Science* 238:1280–1283, each of which is incorporated herein by reference. (In general, the coding sequence need only be modified to include the coding sequence for the HPAP sequence CLEPYTACDLAPPAGTTD (SEQ ID NO:126) (one does not incorporate the entire HPAP anchoring sequence, described below) to produce the desired form of the receptor coding sequence.)

The resulting nucleic acid will be transformed into a recombinant host cell in which the nucleic acid can be transcribed and the mRNA transcript translated to produce the receptor-anchor sequence fusion protein. The fusion protein is then isolated from the host cell and employed in the methods of the present invention, which can facilitate the isolation and purification process.

In a particularly preferred embodiment, the soluble form of the PTH receptor will be expressed on the surface of the host cell. More specifically, the receptor is secreted from the cytoplasm of the cell and anchored into the cell membrane. When such a protein is first translated (to produce the "nascent" protein), the protein typically contains a sequence of amino acids at the amino-terminus that directs secretion of the protein from the cytoplasm to the membrane. The receptor fusion protein will also comprise other sequences of amino acids that direct the protein to become integrated into the membrane. In some cases, the cell surface proteins are anchored to the membrane by a phosphoinositol-glycan "tail" attached to the carboxy-terminal amino acids of the protein. In these cases, the attachment is typically directed by a sequence of amino acids located at the carboxy-terminus of the nascent protein, part of which sequence is cleaved from the protein during the attachment process. In the case of human placental alkaline phosphatase, this sequence is: CLEPYTACDLAPPAGTTDAAHPGRSV-VPALLPLLAGTLLLLETATAP (SEQ ID NO:127) (the "HPAP anchoring sequence"). The HPAP anchoring sequence may optionally contain the dipeptide AA at the amino-terminal end of the sequence, although these residues are not necessary for anchoring. These types of cellular processing are well known to those of skill in the art and are summarized here only for convenience. When the phospholipid anchor is via a phosphoinositol-glycan linkage, the receptor can be harvested from the recombinant cell by treatment with phospholipase C. See Caras et al., 1989, *Science* 243:1196–1198, and Lin et al., 10 Aug. 1990, *Science* 249:677–679. Other carboxy-terminal, membrane anchoring signal sequences are known and can be used in the present methods, but the HPAP anchoring sequence is preferred.

Suitable host cells for these purposes include eukaryotic host cells; CHO cells are especially preferred. Prokaryotic host cells typically will not recognize the HPAP anchoring sequence, but one can still produce receptors comprising the HPAP sequence that can be used for purposes of the present invention.

Once one has produced the receptor-HPAP sequence fusion protein, one can then apply the present methods and reagents to achieve a variety of goals. For instance, after one treats a population of cells with the recombinant DNA expression vector encoding the receptor-HPAP fusion protein under conditions designed to promote uptake of the vector by the cells (a process called "transfection" or "transformation"), one then will want to identify which cells contain the vector and express the receptor. More importantly, one will usually want to identify those cells that produce the highest levels of the receptor. The present invention provides such a method, which involves treating the cells with a labeled antibody that binds to the HPAP sequence, separating cells that bind to the antibody from cells that do not bind the antibody, and isolating those cells that bind the greatest amount of antibody. Those of skill in the art recognize that the antibody can either be directly labeled, i.e., a fluorophore is covalently attached to the antibody, or indirectly labeled, i.e., a labeled second antibody that binds to the anti-HPAP sequence antibody. In a preferred embodiment, this process is carried out on a fluorescence activated cell sorter (FACS) instrument, the antibody is directly labeled with fluorescein isothiocyanate (FITC), and the antibody is Ab179.

Once the desired transformed cell lines have been identified and isolated, one will typically want to isolate the recombinant receptor from cultured cells. The present invention also provides methods and reagents for this purpose. In a preferred mode, an anti-HPAP antibody is used to prepare an affinity column, over which is passed cell culture media from transformed cells treated with PLC, which cleaves the receptor from the cell surface. Preferably, the cultured cells are washed with serum-free media prior to treatment with PLC. A single pass of the media resulting from PLC treatment over an anti-HPAP antibody affinity column will isolate the receptor, which, when eluted from the column, will be produced at purities of 90% and higher. Of course, one need not use a column, as similar levels of purity can be achieved by other means. For instance, one could attach the antibody to beads, mix the beads with the cell culture media, isolate the beads, and then remove the receptor from the beads to produce a pure preparation of the receptor.

According to another embodiment, the soluble form of the PTH receptor is produced by expression of the extracellular domain as a fusion with an immunoglobulin molecule in which the heavy and light chain V-regions are replaced by the extracellular domain. A further embodiment of this invention provides for the expression of the extracellular domain of the PTH receptor as a soluble protein. In a particularly preferred embodiment, the PTH receptor fragment will possess an appropriate antibody recognition motif or other "handle" with which the receptor fragment can be immobilized, for example, for receptor-binding assays.

C. Expression as a Soluble Protein

According to another embodiment, the extracellular soluble domain of the PTH receptor will be expressed as a soluble protein, optionally possessed of an appropriate antibody recognition motif or other handle with which it can be immobilized in a general way such that it is suitable for receptor-binding assays. Preparation of the cell lines useful for expressing a soluble form of the PTH receptor can be accomplished by standard methods of transforming many different kinds of cells with appropriate expression vectors. See, e.g., Ausubel et all. (1987 and supplements) *Current Protocols in Molecular Biology*, Greene Publishing/Wiley-Interscience, New York, which is incorporated herein by reference. Proper selection of a combination of cellular properties and expression vector properties can lead to improved methods of producing the desired PTH receptor fragment. The expression vehicles may be introduced into the cells using methods well known in the art such as calcium phosphate precipitation (discussed below), lipofectin electroporation, or DEAE dextran transformation.

Various methods are available for expressing defined proteins at high levels. Amplification methods similar to those using dehydrofolate reductase (DHFR) can be applied. See, e.g.,Kaufman et al. (1985) *Mol. Cell. Biol.* 5:1750–1759, which is incorporated herein by reference. Other well known expression techniques will also be applicable.

In particular, cell cultures are available to express the nucleic acids described. Usually, the fragments are secreted thereby considerably simplifying purification of the receptor fragments. The cells need not be disrupted and cellular contamination is minimized. Thus, the cells will be separable from the secreted products by physical techniques while allowing recovery of the intact cells. See, e.g., Ausubel et al. (1987 and supplements) *Current Protocols in Molecular Biology*, Greene/Wiley-Interscience, New York, especially section 10:Vii.

Usually, the soluble proteins will be secreted, and will be susceptible to recovery from the medium. Various techniques will be available for separating the soluble proteins in the media from the cells, e.g., filtration or centrifugation. Cell cultures attached to solid substrates will be easily separable from the medium by filtration or centrifugation, while suspension cultures of fragile cells will usually be subjected to centrifugation.

Standard methods for protein purification will be used, e.g., chromatography, centrifugation, precipitations, electrophoresis, immunoaffinity methods, and other techniques well known to protein chemists and enzymologists. See, e.g., Deutscher et al. (1990) *Protein Purification, in Methods in Enzymology*; and Ausubel et al. (1987 and supplements) *Current Protocols in Molecular Biology*.

Particularly useful purification reagents include affinity reagents, e.g., either PTH-ligand affinity columns or immunoaffinity columns. A PTH-ligand affinity column will be readily prepared using a cloned PTH-ligand sequence or analog for isolation of the protein product, and attachment to a solid substrate. An immunoaffinity column will be readily prepared by attaching immunoglobulins prepared against PTH-R peptides, either produced by the cells of the invention, or by other methods.

Fusion proteins will typically be made by either recombinant nucleic acid methods with expression, or by synthetic polypeptide methods. Techniques for nucleic acid manipulation are described generally, for example, in Sambrook et al. (1989) *Molecular Cloning: A Laboratory Manual* (2nd ed.) volumes 1–3, Cold Spring Harbor Laboratory, which is hereby incorporated herein by reference. Techniques for synthesis of polypeptides are described, for example in Merrifield (1963) *J. Amer. Chem. Soc.* 85:2149–2456; Atherton et al. (1989) *Solid Phase Peptide Synthesis: A Practical Approach*, IRL Press, Oxford; and Merrifield (1986) *Science* 232:341–347; each of which is hereby incorporated herein by reference.

The recombinant nucleic acid sequences used to produce fusion proteins of the present invention may be derived from natural or synthetic sequences. Many natural gene sequences are available from various cDNA or from genomic libraries using appropriate probes, see, e.g., GenBank™, National Institutes of Health.

Although the most common procaryote cells used as hosts are strains of *E. coli* other prokaryotes such as Bacillus subtilis or Pseudomonas may also be used. Usually the control sequence will be a eukaryotic promoter for expression in a mammalian cell. In some vehicles the receptor's own control sequences may also be used. A common prokaryotic plasmid vector for transforming *E. coli* is pBR322 or its derivatives, e.g. the plasmid pkt279 (Clontech), see Bolavar et al. (1977) *Gene*, 2:95. The prokaryotic vectors may also contain prokaryotic promoters for transcription initiation, optionally with an operator. Examples of most commonly used prokaryotic promoters include the beta-lactamase (penicillinase); lactose (lac) promoter, see Cheng et al. (1977) *Nature* 198:1056; tryptophan promoter (trp), see Goeddell et al. (1980) *Nucleic Acid Res.*, 8: 457); $P_L$ promoter; and the N-gene ribosome binding site, see Shimatake et al. (1981) *Nature*, 292:128–; each of which is hereby incorporated herein by reference. Promoters used in conjunction with yeast can be promoters derived from the enolase gene, see Holland et al. (1981) *J. Biol. Chem.*, 256:1385; or the promoter for the synthesis of glycolytic enzymes such as 3-phosphoglycerate kinase, see Hitzeman et al. (1980) *J. Biol. Chem.*, 255:.

Appropriate non-native mammalian promoters will include the early and late promoters from SV40, see Fiers et al. (1978) *Nature* 273:113; or promoters derived from murine muloney leukemia virus, mouse mammary tumor virus, avian sarcoma viruses, adenovirus II, bovine papilloma virus, or polyoma. In addition, the construct may be joined to an amplifiable gene, e.g. dihydrofolate reductase (DHFR) so that multiple copies of the PDGF receptor gene may be made. See, e.g., Kaufman et al. (1985) *Mol. and Cell. Biol.* 5:1750–1759; and Levinson et al. EPO publication nos. 0117059 and 0117060, each of which is incorporated hereby by reference.

Prokaryotes may be transformed by various methods, including using $CaCl_2$, see Cohen (1972) *Proc. Nat'l Acad. Sci. USA*, 69:2110; or the RbC1 method, see Maniatis et al. (1982) *Molecular Cloning: A Laboratory Manual*, Cold Spring Harbor Press. Yeast may be transformed, e.g., using a method described by Van Solingen et al. (1977) *J. Bacteriol.* 130:946; or Hsiao et al. (1979) *Proc. Nat'l Acad. Sci. USA* 76:3829. With respect to eukaryotes, mammalian cells may be transfected using a calcium phosphate precipitation method, see, e.g., Graham and van der Eb (1978) *Virology*, 52:546; or by lipofectin (BRL) or retroviral infection, see, e.g., Gilboa (1983) *Experimental Manipulation of Gene Expression*, Chap. 9, Academic Press P. 175. The actual expression vectors containing appropriate sequences may be prepared according to standard techniques involving ligation and restriction enzymes. See e.g., Maniatis supra. Commercially available restriction enzymes for cleaving specific sites of DNA may be obtained from New England BioLabs, Beverly, Mass.

Particular co-transformations with other genes may be particularly useful. For example, it may be desired to co-express the nucleic acid with another processing enzyme. Such enzymes include signal peptidase, tertiary conformation conferring enzymes, or glycosylating enzymes. This expression method may provide processing functions which otherwise might be lacking in the expression host, e.g., mammalian-like glycosylation in a prokaryote expression system. Alternatively, the host cell selected for expression may be chosen on the basis of the natural expression of those processing enzymes.

Cell clones are selected by using markers depending on the mode of the vector construction. The marker may be on the same or a different DNA molecule preferably the same DNA molecule. With mammalian cells the receptor gene itself may be the best marker. In prokaryotic hosts the transformant may be selected by resistance to ampicillin, tetracycline, or other antibiotics. Production of a particular product based on temperature sensitivity or compensation may serve as appropriate markers. Various methods may be used to harvest and purify the PTH-R receptor protein or peptide fragment. The peptide may be isolated from a lysate of the host. The peptide may be isolated from the cell supernatant if the peptide is secreted. The PTH-R peptide is then further purified as discussed above using HPLC, electrophoresis, or affinity chromatography, e.g., immunoaffinity or ligand affinity.

Another method which can be used to isolate cDNA clones of PTH-R related species involves the use of the polymerase chain reaction (PCR). See, e.g., Saiki et al. (1985) *Science* 230:1350. In this approach two oligonucleotides corresponding to distinct regions of the PTH-R sequence are synthesized and then used in the PCR reaction, typically to amplify receptor-related mRNA transcripts from an mRNA source. Annealing of the oligonucleotides and PCR reactions are performed under conditions of reduced stringency. The resulting amplified fragments are subcloned, and the resulting recombinant colonies are probed with $^{32}$P-labeled full-length PTH-R cDNA. Clones which hybridize under low but not high stringency conditions represent PTH-R related mRNA transcripts. This approach can also be used to isolate variant PTH-R cDNA species which arise as a result of alternative splicing, see Frohman et al. (1988) *Proc. Nat'l Acad. Sci. USA*, 85:8998.

D. Assays

The present invention also provide methods for assaying ligands for the modified PTH receptor described herein. For example, soluble ligand binding fragments will be useful as competing sites for ligand binding, a useful property in a ligand binding assay. In particular, the present invention provides an assay to screen for PTH binding inhibition, allowing screening of large numbers of compounds. These compounds may be assayed in vitro, which allows testing of cytotoxic or membrane disruptive compounds. The present solid phase system allows reproducible, sensitive, specific, and readily automated assay procedures. Polystyrene 96-well plates may be coated with the appropriate construct with ligand binding region's to assay for ligand binding activity. Moreover, modifications to the ligand binding domains will lead to binding region combinations with different ligand binding affinities. Thus, modulation of ligand effected response may be easily achieved by inclusion of the appropriate affinity modified analogue.

Solid phase assays using these modified receptors may also be developed, providing greater sensitivity or improved capacity over unmodified binding regions. In particular, the extracellular domain will usually be attached to a plastic or other solid phase substrate. The binding regions will usually be selected for a combination of the affinity and ligand binding spectrum of the modified binding segments. Appropriate ligands will often be introduced to determine the ligand binding activity and affinity. Different ligand binding region combinations will be used, and can be used to test for differently modified, e.g., labeled, ligands.

The invention will be more fully described and understood with reference to the following examples. These examples are provided by way of illustration only and not by way of limitation. Those skilled in the art will readily appreciate a variety of noncritical parameters which could be changed or modified to yield essentially similar results.

EXPERIMENTAL

In general, standard techniques of recombinant DNA technology are described in various publications, e.g., Sambrook et al. (1989) *Molecular Cloning: A Laboratory Manual*, Cold Spring Harbor Laboratory; Ausubel et al. (1987) *Current Protocols in Molecular Biology*, vols. 1 and 2 and supplements; and Wu and Grossman (eds.) (1987) *Methods in Enzymology*, Vol. 53 (Recombinant DNA Part D); each of which is incorporated herein by reference.

EXAMPLE 1

Construction of Plasmid pBAD/PepEV

Figure 2:
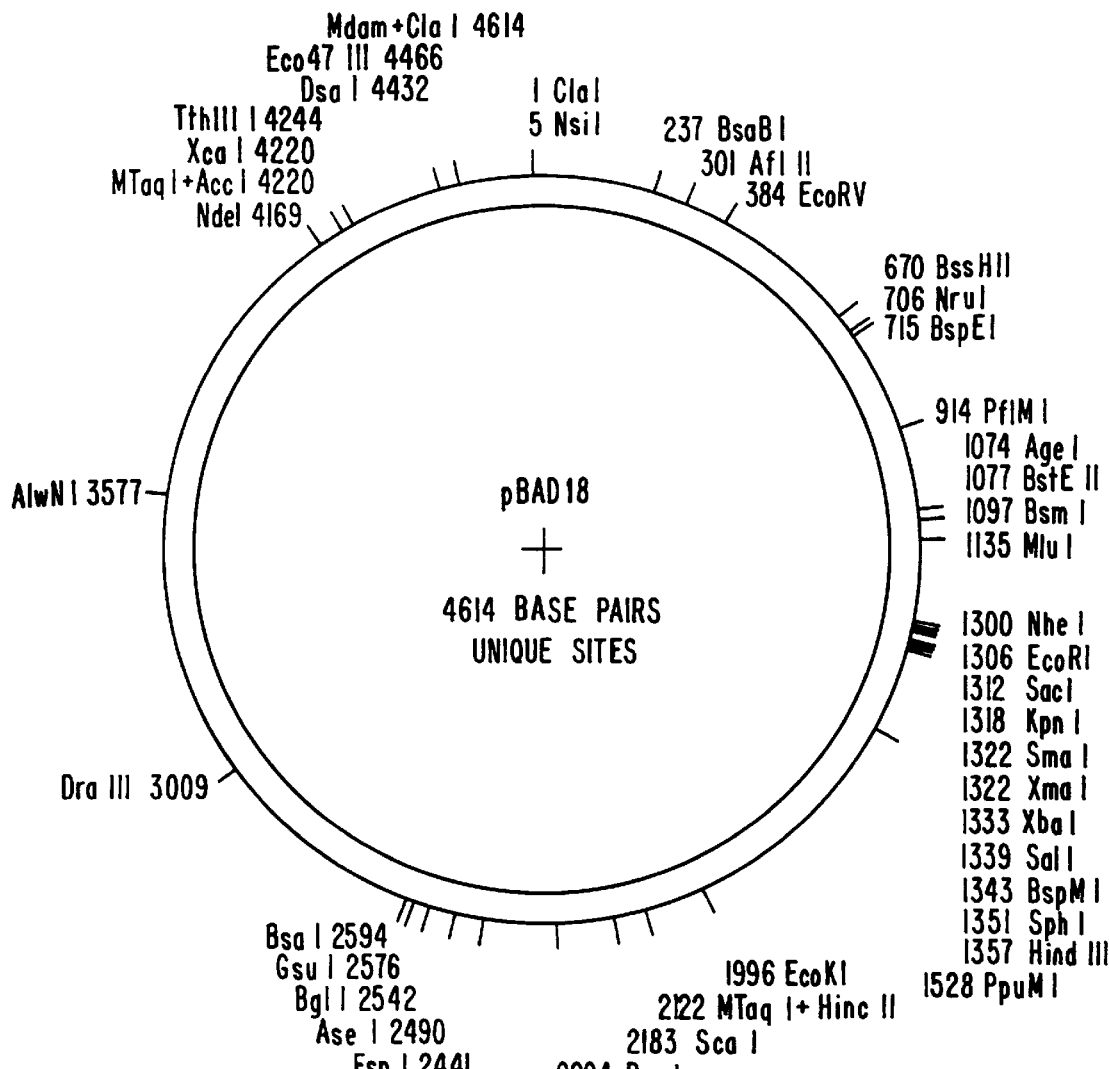
FIG. 2 provides a detailed restriction site map of plasmid pBAD18.

The PTH analog expression vector was constructed in several steps using plasmid pBAD18 as the starting plasmid. Plasmid pBAD18 contains the araB promoter followed by a polylinker and a terminator under the control of the positive/negative regulator araC, also specified by the plasmid. Plasmid pBAD18 also contains a modified plasmid pBR322 origin and the bla gene to permit replication and selection in *E. coli*, as well as the phage M13 intragenic region to permit rescue of single-stranded DNA. A restriction site and function map of plasmid pBAD18 is shown in FIG. 1; a more detailed restriction site map of plasmid pBAD18 is shown in FIG. 2. For purposes of the present invention, however, the actual cloning vector used to construct the expression vectors of the invention is not critical.

For instance, plasmid pMC3, could serve as the cloning vector in place of plasmid pBAD18 in the protocols below. Plasmid pMC3 is described in U.S. patent application Ser. No. 778,233, filed Oct. 16, 1991, incorporated herein by reference. Plasmid pMC3 differs from plasmid pBAD18 in that plasmid pMC3 encodes a dynorphin B-tailed lac repressor in the region corresponding to the NheI-XbaI region of the multiple cloning site of pBAD18 and encodes a lac operator sequence in the region corresponding to the NdeI-ClaI fragment of plasmid pBAD18. As this latter fragment is not essential for purposes of the present invention, one could readily construct suitable vectors for purposes of the present invention from plasmid pMC3. Plasmid pMC3 is available in strain ARI161 from the American Type Culture Collection under the accession number ATCC 68818. For completeness, however, the sequence of the NdeI-ClaI fragment of plasmid pBAD18 is shown below.

Plasmid pBAD18 was digested with restriction enzymes NheI and HinDIII, and the large DNA fragment resulting from the digestion was gel purified. A piece of synthetic "linker" DNA, described below, was then added to the plasmid pBAD18 DNA at a molar ratio of 3:1 (about 0.75 µg of vector), and the resulting mixture was ligated overnight at 14° C. with T4 DNA ligase. The DNA was then precipitated, resuspended in TE buffer, and "wild" type vector destroyed by digestion with restriction enzyme KpnI. The ligated DNA was then precipitated, resuspended in TE, and electroporated into *E. coli* cell line DH10B (commercially available from Gibco BRL). The transformed cells were then plated onto LB (Luria-Bertani media) agar plates containing 50 µg/mL of ampicillin, and after overnight culture at 37° C., about 20 colonies were selected, grown individually for 8 hours in 3 mL of media containing ampicillin, and the plasmid DNA purified. Restriction analysis of these plasmids indicated that all 20 contained the linker. Four of these plasmids were then sequenced, and all four contained the correct linker sequence. The plasmid that was constructed was designated plasmid pBAD/PepEV.

The linker used in the construction of plasmid pBAD/PepEV contains the Shine-Dalgarno ribosome binding site followed by six nucleotides and an ATG start codon. The start codon is followed by an alanine codon, because this structure may enhance synthesis of the product of a subsequent coding sequence. The alanine is followed by a $His_6$ coding sequence, which allows rapid purification of any protein containing this sequence on a $Ni^{++}$ chelation column (see U.S. Pat. No. 4,551,271, incorporated herein by reference). A SalI site follows the polyhistidine coding sequence and is separated from an XhoI site by six nucleotides. The XhoI site is followed by a double stop codon (TAATAA) and a HinDIII site. The linker was constructed from a pair of oligonucleotides (ON-718 and ON-719), the sequences of which are shown below.

---

NdeI-
CATATGGTGCACTCTCAGTACAATCTGCTCTGATGCCGCATAGTTAAGCCAGTA
TACACTCCGCTATCGCTACGTGACTGGGTCATGGCTGCGCCCCGACACCCGCCAACACC
CGCTGACGCGCCCTGACGGGCTTGTCTGCTCCCGGCATCCGCTTACAGACAAGCTGTGA
CCGTCTCCGGGAGCTGCATGTGTCAGAGGTTTTACCGTCATCACCGAAACGCGCGAGGC
AGCAAGGAGATGGCGCCCAACAGTCCCCCGGCCACGGGGCCTGCCACCATACCCACGCC
GAAACAAGCGCTCATGAGCCCGAAGTGGCGAGCCCGATCTTCCCCATCGGTGATGTCGG
CGATATAGGCGCCAGCAACCGCACCTGTGGCGCCGGTGATGCCGGCCACGATGCGTCCG
GCGTAGAGGATCTAATTCTCATGTTTGACAGCTTATCATCGAT-ClaI (SEQ ID NO:128)

---

ON-718:
5'-GGCAGGCTAGCTAACTAATGGAGGATACATAAATGGCTCACCA
CCACCATCACCATGTCGACTGACGACTCGAGTAATAAAAGCTTGGTCG-3' (SEQ ID NO:129)

-continued

ON-719:
5'-CGACCAAGCTTTTATTACTCGAGTCGTCAGTCGACATGGTGAT
GGTGGTGGTGAGCCATTTATGTATCCTCCATTAGTTAGCTAGCCTGCC-3' (SEQ ID NO:130)

To prepare the linker that was used in the construction of plasmid pBAD/PepEV, equal amounts (about 0.25 µg) of each oligonucleotide in TE buffer (10 mM Tris, 1 mM EDTA, pH=8.0), were mixed, heated to 95° C. for 2 minutes, and then allowed to cool slowly to room temperature. Restriction enzyme digestion buffer was then added, and the DNA was then treated with restriction enzymes NheI and HinDIII.

Plasmid pBAD/PepEV serves as a useful cloning vector for constructing expression vectors of the invention.

EXAMPLE 2

Construction of PTH Expression Vectors

The PTH analog protein coding sequence contains efficiently expressed E. coli codons and was constructed using a pair of oligonucleotides (ON-716 and ON-717), shown below.

ON-716: 5'-GGACGGCTCGAGATGTCCGTTTCCGAAATCCAGCT
GCTGCACAACCTGGGTAAACACCTGAACTCCCTGGAACG-3' (SEQ ID NO:131)
ON-717: 5'-CCTGCCGTCGACCATGTAGTTGTGAACGTCCTGCAG
TTTTTACGCAGCCATTCAACACGTTCCAGGGAGTTCA-3' (SEQ ID NO: 132)

The two oligonucleotides (about 0.25 µg of each) were mixed together and heated to 95° C.; then, TAq polymerase was added, and the oligonucleotides were annealed at 60° C. Extension of the oligonucleotides to form double-stranded DNA was performed at 72° C. The double-stranded DNA was then precipitated with isopropanol and sodium acetate and resuspended in sterile deionized water. 10X restriction enzyme buffer was added to the mixture, and the DNA was treated with restriction enzymes XhoI and SalI for 2 hours at 37° C. The DNA was then precipitated as above and resuspended in sterile deionized water.

Plasmid pBAD/PepEV was digested with restriction enzymes SalI and XhoI, and the large fragment resulting from the digestion was gel purified. The PTH analog protein coding sequence ("the insert") was added to the large SalI-XhoI plasmid pBAD/PepEV fragment at a molar ratio of 3:1 (about 0.75 µg of the plasmid fragment was used) and ligated overnight as above. This ligation resulted in the construction of the following plasmids: (1) circularized and polymerized plasmid pBAD/PepEV SalI-XhoI fragment, because the SalI and XhoI single-stranded extensions are complementary; (2) plasmid pBAD/PTH/MNC, where "MNC" stands for "monomer non-coding," because the insert was inserted such that the SalI single-stranded extension of the insert ligated to the SalI extension of the plasmid, and the XhoI extension of the insert ligated to the XhoI extension of the plasmid, thus resulting in the PTH analog protein coding sequence positioned in the wrong orientation for expression from the araB promoter; and (3) pBAD/PTH/MC, where "MC" stands for "monomer coding," because the insert was inserted such that the SalI extension of the insert ligated to the XhoI extension of the vector and the XhoI extension of the insert ligated to the SalI extension of the vector, thus resulting in the PTH analog protein coding sequence positioned in the correct orientation for expression from the araB promoter.

Plasmid pBAD/PTH/MC can be used to drive expression of a dimeric or higher order oligomer fusion protein comprising the 34 amino acid PTH analog protein of the invention and a Met-Ala-polyhistidine-Val-Glu peptide. The fusion protein can be purified on a nickel chelate column, from which the fusion protein can be released in pure form and then cleaved with CNBr to produce the 34 amino acid PTH analog protein of the invention.

Plasmid pBAD/PTH/MNC was used to make additional expression vectors of the invention, from which the PTH analog protein is synthesized in recombinant host cells as a fusion protein with multiple copies of the PTH analog protein. Plasmid pBAD/PTH/MNC was double digested with either BglI and SalI or BglI and XhoI. The double digest of BglI and SalI resulted in two fragments, one containing 1187 bp and the other containing 3545 bp, and the double digest of BglI and XhoI resulted in two fragments, one containing 1073 bp and the other containing 3659 bp. The 1187 bp fragment from the BglI and SalI digestion and the 3659 bp fragment from the BglI and XhoI digestion were gel purified and ligated at a 1:1 molar ratio. The resulting plasmid was electroporated into E. coli DH10B. Purified plasmid DNA was assayed by restriction mapping to ensure dimerization of the coding sequence and then was subjected to DNA sequencing to ensure that the plasmid contained the correct sequence. This plasmid was designated pBAD/PTH/DNC, where "DNC" stands for "dimer noncoding."

This procedure was repeated to produce the PTH tetramer, octomer, 16-mer and 32-mer; (designated pBAD/PTH/TNC, pBAD/PTH/ONC, pBAD/PTH/16NC, and pBAD/PTH/32NC, respectively). In all cases, the linkage of one coding sequence unit to the next involved, at the DNA level, the ligation of a SalI site to an XhoI site, with the resulting removal of both of those individual restriction sites between the individual PTH coding sequences while preserving those sites that flank the polymerized coding sequences. As is apparent to those of skill in the art, any size of polymer can be obtained by combining the appropriate insert fragment with the appropriate vector. For instance, the trimer counterpart can be prepared by ligating the small BglI-SalI restriction fragment of plasmid pBAD/PTH/MNC with the large BglI-XhoI fragment of plasmid pBAD/PTH/DNC. Those of skill in the art will also recognize that the VEM sequence can be of any length so long as it encodes the appropriate restriction sites and possesses a Met residue between the polymeric subunits. Thus, the VEM sequence that occurs in the polymeric PTH fusion proteins of the invention is directly related to the number of SalI/XhoI ligations used in constructing the polymer.

To place the coding sequence polymers in the proper orientation for expression, each plasmid was digested with SalI and XhoI and then religated. After precipitation and resuspension in deionized water, the ligated DNA was digested with XhoI to remove plasmids with coding sequence polymers in the noncoding direction. The plasmids were again electroporated into DH10B cells. Individual clones were selected, and the plasmids were purified and then analysed by restriction mapping and DNA sequencing. The desired plasmids, with the coding sequence polymers positioned correctly for expression under the control of the araB promoter were designated similarly to their non-coding counterparts, except that "NC" was changed to "C" in each name.

EXAMPLE 3

PTH Analog Protein Expression and Purification

E. coli DH10B containing the plasmid pBAD/PTH/OC (i.e., the 8-mer coding plasmid) was grown overnight in LB-media containing ampicillin (50 to 100 μg/mL). Ten mL of this culture were used to inoculate a 500 mL culture of Superbroth (35 g/L Bacto-tryptone, 20 g/L yeast extract, 5 g/L NaCl, and NaOH to pH=7.5) containing ampicillin. The cells were allowed to grow to an $OD_{600}$ of about 0.5 to 1.0 and L-(+)-arabinose was added to a final concentration of 0.2%. The cells were allowed to grow for an additional 3 hours. At the end of this time, the $OD_{600}$ was between 1.5 to 3. The cells were harvested by centrifugation and washed sequentially with 250 mL of WTEK buffer (50 mM Tris, pH=7.5, 10 mM EDTA, 100 mM KCl); 250 mL of PBS; and 250 mL of 10 mM Tris, pH=7.5. The cells were then resuspended in 100 mL of a solution composed of 10 mM Tris, pH=7.5; 0.1 mg/mL of protease inhibitor N-tosyl-L-phenylalanine chloromethyl ketone (TPCK); 0.1 mg/mL of protease inhibitor N-tosyl-L-lysine chloromethyl ketone (TLCK); 0.1 mg/mL of protease inhibitor phenylmethylsulfonyl fluoride (PMSF); and 0.05 mg/mL lysozyme). The resulting solution was incubated on ice for 1 hour. The cells were then freeze-thawed; 1 mg of DNAse was added to the freeze-thawed cells; and the resulting mixture was incubated on ice for an additional hour.

Inclusion bodies from the cells were purified by centrifugation at 10,000×g for 15 minutes. The inclusion bodies were solubilized in 10% SDS, but in some cases, sonication of the sample was also necessary to solubilize all of the protein. Binding buffer (5 mM imidazole, 500 mM NaCl, and 20 mM Tris, pH=7.9) was added to dilute the SDS concentration to 1%, and the sample was loaded onto a column containing His-bind resin (Novagen). The column was then washed with 15 column volumes of binding buffer, and bound protein was then eluted with 1 column volume of elution buffer (500 mM NaCl, 100 mM EDTA, and 50 mM Tris, pH=7.9). Two volumes of absolute ethanol were then added to precipitate the protein.

The precipitated PTH polymer was then dissolved in 70% formic acid, and a 500-fold (100 to 1000-fold excess can be used) molar excess of CNBr was added. A time course of cleavage (conducted at different CNBr concentrations to determine the optimal time), as assayed by amino acid analysis, indicated that complete cleavage was achieved in 2 hours at room temperature. After CNBr cleavage, the peptides were lyophilized and resuspended in distilled water. The peptide was purified resuspended in Buffer A (0.1% TFA) and further purified by HPLC using a VYDAC C-18 Hamilton semi-preparative column. Approximately 30 mg of peptide was injected onto the column. The peptide was then eluted with a gradient of 20–40% acetonitrile/0.1% TFA over 40 minutes. The major peak, eluting at approximately 15 minutes, was collected and lyophilized to dryness. Analysis of this peptide by SDS-PAGE and IEF indicated a single species of approximately 4000 daltons with an isoelectric point of approximately 8.7. Further analysis by analytical HPLC on a Vydac C18 column, by capillary zonal electrophoresis, and by amino acid analysis indicated that the peptide was greater than 95% pure.

EXAMPLE 4

PTH Analog Activity Assay

PTH concentrations were determined by $OD_{280}$ using an extinction coefficient of 6600 for the recombinant peptide and 5500 for the synthetic peptide. The rat osteosarcoma cell line UMR106 (ATCC CRL 1661) was used for in vitro testing of the peptide's ability to activate the PTH receptor. Activation of the PTH receptor leads to an intracellular rise in cAMP concentration.

The UMR106 cells were plated at $1.2 \times 10^5$ per well in a 48 well dish. The media (DMEM with fetal calf serum) was removed, and 1 mL of fresh media was applied. PTH (recombinant or synthetic) at various concentrations and 3-isobutyl-1-methyl xanthine (IBMX) at 1 mM final concentration were then added to each well of the plate, which was then incubated for 5 minutes at room temperature. The media was then removed and the cells quickly washed with PBS. The cells were then extracted three times with 1 mL of absolute ethanol. The three extractions were combined and the ethanol removed by evaporation in a "speed vac" centrifuge. The extract was then redissolved in 0.5 mL of buffer (0.05M NaAcetate, pH=5.8, and 0.01% azide). The cAMP concentration was determined by scintillation proximity assay using a kit available from Amersham. This data indicated that the recombinant PTH analog is approximately 2-to-10-fold more active than the synthetic human PTH.

EXAMPLE 5

General Procedure for Production of PTH Mutants

The following is a generalized procedure for the production of PTH mutants containing the amino acid lysine, arginine, glutamic acid, or glycine at every position throughout the peptide.

Two overlapping oligonucleotides containing the sequence for a small section of the peptide that is to be mutated were synthesized. These overlapping oligonucleotides were flanked on either end by restriction sites contained within the PTH gene. An internal restriction site was removed by a conservative codon change. The two oligonucleotides were added together at equimolar concentrations and allowed to anneal.

Taq polymerase was used to fill out the single stranded regions. The appropriate restriction enzymes were then added to the double stranded oligonucleotide to generate the appropriate "sticky" ends. The oligonucleotide was then inserted into an appropriately restricted plasmid.

The pBAD/TrpLEPTH plasmid was cut with the same restriction enzymes and the appropriate fragments were isolated by agarose gel electrophoresis and purified by conventional methods. The plasmid and the insert were added together at a molar ration of 1:3 and ligated for 1 hour at 14° C.

Plasmids that have the double stranded oligonucleotide ligated will be missing a restriction site. Plasmids that do not have an insert can be destroyed by restriction with the appropriate enzyme.

The plasmid was then electroporated into the E. coli cell line XL1Blue (available from Stratagene, La Jolla, Calif.) Phagemid DNA was prepared by standard methods and the mutants were determined by DNA sequencing.

Once a mutant was discovered, the plasmid was transferred into the *E. coli* cell line DH10B (available from Gilbco-BRL, Grand Island, N.Y.) for expression. The PTH mutants were expressed and purified as described above.

CONCLUSION

Many other embodiments of the invention will be apparent to those of skill in the art upon reviewing the above description, and to aid in the understanding of the invention, all publications and other references or patent documents in the above description are incorporated herein by reference. The above description is intended to be illustrative and not restrictive, and the scope of the invention should, therefore, be determined with reference to the appended claims, along with the full scope of equivalents to which such claims are entitled.

SEQUENCE LISTING ( 1 ) GENERAL INFORMATION:

( i i i ) NUMBER OF SEQUENCES: 132

( 2 ) INFORMATION FOR SEQ ID NO:1:

( i ) SEQUENCE CHARACTERISTICS:
        ( A ) LENGTH: 84 amino acids
        ( B ) TYPE: amino acid
        ( D ) TOPOLOGY: unknown ( i i ) MOLECULE TYPE: protein ( i x ) FEATURE:
        ( A ) NAME/KEY: Protein
        ( B ) LOCATION: 1..84
        ( D ) OTHER INFORMATION: /note= "84 amino acid PTH"

( x i ) SEQUENCE DESCRIPTION: SEQ ID NO:1:

```
Ser  Val  Ser  Glu  Ile  Gln  Leu  Met  His  Asn  Leu  Gly  Lys  His  Leu  Asn
1                   5                        10                       15

Ser  Met  Glu  Arg  Val  Glu  Trp  Leu  Arg  Lys  Lys  Leu  Gln  Asp  Val  His
               20                       25                       30

Asn  Phe  Val  Ala  Leu  Gly  Ala  Pro  Leu  Ala  Pro  Arg  Asp  Ala  Gly  Ser
          35                       40                       45

Gln  Arg  Pro  Arg  Lys  Lys  Glu  Asp  Asn  Val  Leu  Val  Glu  Ser  His  Glu
     50                       55                       60

Lys  Ser  Leu  Gly  Glu  Ala  Asp  Lys  Ala  Asp  Val  Asp  Val  Leu  Thr  Lys
65                       70                       75                       80

Ala  Lys  Ser  Gln
```

( 2 ) INFORMATION FOR SEQ ID NO:2:

( i ) SEQUENCE CHARACTERISTICS:
        ( A ) LENGTH: 34 amino acids
        ( B ) TYPE: amino acid
        ( D ) TOPOLOGY: unknown ( i i ) MOLECULE TYPE: protein ( i x ) FEATURE:
        ( A ) NAME/KEY: Peptide
        ( B ) LOCATION: 1..34
        ( D ) OTHER INFORMATION: /note= "The sequence of the 34
            amino acid truncated human PTH peptide,
            designated: Human PTH."

( x i ) SEQUENCE DESCRIPTION: SEQ ID NO:2:

```
Ser  Val  Ser  Glu  Ile  Gln  Leu  Met  His  Asn  Leu  Gly  Lys  His  Leu  Asn
1                   5                        10                       15

Ser  Met  Glu  Arg  Val  Glu  Trp  Leu  Arg  Lys  Lys  Leu  Gln  Asp  Val  His
               20                       25                       30
```

Asn Phe ( 2 ) INFORMATION FOR SEQ ID NO:3:

( i ) SEQUENCE CHARACTERISTICS:
        ( A ) LENGTH: 34 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:3:

```
Ser  Val  Ser  Glu  Ile  Gln  Leu  Leu  His  Asn  Leu  Gly  Lys  His  Leu  Asn
1              5                        10                        15
Ser  Leu  Glu  Arg  Val  Glu  Trp  Leu  Arg  Lys  Lys  Leu  Gln  Asp  Val  His
               20                       25                   30
Asn  Tyr
```

( 2 ) INFORMATION FOR SEQ ID NO:4:

( i ) SEQUENCE CHARACTERISTICS:
        ( A ) LENGTH: 35 amino acids
        ( B ) TYPE: amino acid
        ( D ) TOPOLOGY: unknown ( i i ) MOLECULE TYPE: protein ( i x ) FEATURE:
        ( A ) NAME/KEY: Modified-site
        ( B ) LOCATION: 35
        ( D ) OTHER INFORMATION: /note= "Where "Xaa"is Homoserine
            Lactone"

( x i ) SEQUENCE DESCRIPTION: SEQ ID NO:4:

```
Ser  Val  Ser  Glu  Ile  Gln  Leu  Leu  His  Asn  Leu  Gly  Lys  His  Leu  Asn
1              5                        10                        15
Ser  Leu  Glu  Arg  Val  Glu  Trp  Leu  Arg  Lys  Lys  Leu  Gln  Asp  Val  His
               20                       25                   30
Asn  Tyr  Xaa
          35
```

( 2 ) INFORMATION FOR SEQ ID NO:5:

( i ) SEQUENCE CHARACTERISTICS:
        ( A ) LENGTH: 35 amino acids
        ( B ) TYPE: amino acid
        ( D ) TOPOLOGY: unknown ( i i ) MOLECULE TYPE: protein ( i x ) FEATURE:
        ( A ) NAME/KEY: Modified-site
        ( B ) LOCATION: 35
        ( D ) OTHER INFORMATION: /note= "Where "Xaa"is Homoserine"

( x i ) SEQUENCE DESCRIPTION: SEQ ID NO:5:

```
Ser  Val  Ser  Glu  Ile  Gln  Leu  Leu  His  Asn  Leu  Gly  Lys  His  Leu  Asn
1              5                        10                        15
Ser  Leu  Glu  Arg  Val  Glu  Trp  Leu  Arg  Lys  Lys  Leu  Gln  Asp  Val  His
               20                       25                   30
Asn  Tyr  Xaa
          35
```

( 2 ) INFORMATION FOR SEQ ID NO:6:

( i ) SEQUENCE CHARACTERISTICS:
        ( A ) LENGTH: 6 amino acids ( B ) TYPE: amino acid
          ( D ) TOPOLOGY: unknown ( i i ) MOLECULE TYPE: protein ( i x ) FEATURE:
          ( A ) NAME/KEY: Modified-site
          ( B ) LOCATION: 3
          ( D ) OTHER INFORMATION: /note= "Residue 3, His, may be
                present x times where x is 4,5,6 or more."

( x i ) SEQUENCE DESCRIPTION: SEQ ID NO:6:

Met  Ala  His  Val  Glu  Met
    1                   5

( 2 ) INFORMATION FOR SEQ ID NO:7:

( i ) SEQUENCE CHARACTERISTICS:
          ( A ) LENGTH: 35 amino acids
          ( B ) TYPE: amino acid
          ( D ) TOPOLOGY: unknown ( i i ) MOLECULE TYPE: protein ( x i ) SEQUENCE DESCRIPTION: SEQ ID NO:7:

Ser  Val  Ser  Glu  Ile  Gln  Leu  Leu  His  Asn  Leu  Gly  Lys  His  Leu  Asn
    1                   5                        10                            15

Ser  Leu  Glu  Arg  Val  Glu  Trp  Leu  Arg  Lys  Lys  Leu  Gln  Asp  Val  His
                        20                        25                   30

Asn  Tyr  Met
                35

( 2 ) INFORMATION FOR SEQ ID NO:8:

( i ) SEQUENCE CHARACTERISTICS:
          ( A ) LENGTH: 207 base pairs
          ( B ) TYPE: nucleic acid
          ( C ) STRANDEDNESS: single
          ( D ) TOPOLOGY: linear ( i i ) MOLECULE TYPE: DNA (genomic)

( i x ) FEATURE:
          ( A ) NAME/KEY: CDS
          ( B ) LOCATION: 1..201

( i x ) FEATURE:
          ( A ) NAME/KEY: misc_feature
          ( B ) LOCATION: 1..51
          ( D ) OTHER INFORMATION: /note= "Encodes the leader peptide
                sequence that serves to direct the protein into
                inclusion bodies."

( i x ) FEATURE:
          ( A ) NAME/KEY: misc_feature
          ( B ) LOCATION: 70..174
          ( D ) OTHER INFORMATION: /note= "Encodes the protein or
                peptide of interest"

( i x ) FEATURE:
          ( A ) NAME/KEY: misc_feature
          ( B ) LOCATION: 175..207
          ( D ) OTHER INFORMATION: /note= "Encodes amino acid sequence
                having six histamines that serves as a tag for the
                purification of the protein on a nickel column."

( x i ) SEQUENCE DESCRIPTION: SEQ ID NO:8:

ATG  AAA  GCT  ATC  TTC  GTT  CTG  AAA  GGT  TCC  CTG  GAC  CGT  GAC  CCG  GAA          48
Met  Lys  Ala  Ile  Phe  Val  Leu  Lys  Gly  Ser  Leu  Asp  Arg  Asp  Pro  Glu
1                   5                        10                       15

TTC  GTC  GAC  ATG  ATC  AAC  ATG  TCC  GTT  TCC  GAA  ATC  CAG  CTG  CTG  CAC          96
Phe  Val  Asp  Met  Ile  Asn  Met  Ser  Val  Ser  Glu  Ile  Gln  Leu  Leu  His

```
                    20                         25                          30
AAC  CTG  GGT  AAA  CAC  CTG  AAC  TCC  CTC  GAG  CGT  GTT  GAA  TGG  CTG  CGT    144
Asn  Leu  Gly  Lys  His  Leu  Asn  Ser  Leu  Glu  Arg  Val  Glu  Trp  Leu  Arg
               35                        40                       45

AAA  AAA  CTG  CAG  GAC  GTC  CAC  AAC  TAC  ATG  CAG  ATC  TCC  CAC  CAC  CAC    192
Lys  Lys  Leu  Gln  Asp  Val  His  Asn  Tyr  Met  Gln  Ile  Ser  His  His  His
     50                        55                       60

CAT  CAC  CAT  TAATAA                                                              207
His  His  His
65
```

(2) INFORMATION FOR SEQ ID NO:9:

(i) SEQUENCE CHARACTERISTICS:
        (A) LENGTH: 67 amino acids
        (B) TYPE: amino acid
        (D) TOPOLOGY: linear (ii) MOLECULE TYPE: protein (xi) SEQUENCE DESCRIPTION: SEQ ID NO:9:

```
Met  Lys  Ala  Ile  Phe  Val  Leu  Lys  Gly  Ser  Leu  Asp  Arg  Asp  Pro  Glu
1                   5                        10                       15

Phe  Val  Asp  Met  Ile  Asn  Met  Ser  Val  Ser  Glu  Ile  Gln  Leu  Leu  His
               20                        25                       30

Asn  Leu  Gly  Lys  His  Leu  Asn  Ser  Leu  Glu  Arg  Val  Glu  Trp  Leu  Arg
               35                        40                       45

Lys  Lys  Leu  Gln  Asp  Val  His  Asn  Tyr  Met  Gln  Ile  Ser  His  His  His
     50                        55                       60

His  His  His
65
```

(2) INFORMATION FOR SEQ ID NO:10:

(i) SEQUENCE CHARACTERISTICS:
        (A) LENGTH: 35 amino acids
        (B) TYPE: amino acid
        (D) TOPOLOGY: unknown (ii) MOLECULE TYPE: protein (ix) FEATURE:
        (A) NAME/KEY: Modified-site
        (B) LOCATION: 11
        (D) OTHER INFORMATION: /note= "Where "Xaa"is a neutral or
            positively charged amino acid."

(ix) FEATURE:
        (A) NAME/KEY: Modified-site
        (B) LOCATION: 12
        (D) OTHER INFORMATION: /note= "Where "Xaa"is a neutral
            amino acid."

(ix) FEATURE:
        (A) NAME/KEY: Modified-site
        (B) LOCATION: 13
        (D) OTHER INFORMATION: /note= "Where "Xaa"is a neutral,
            positively charged, or negatively charged amino
            acid."

(ix) FEATURE:
        (A) NAME/KEY: Modified-site
        (B) LOCATION: 15
        (D) OTHER INFORMATION: /note= "Where "Xaa"is a positively
            charged amino acid."

(ix) FEATURE:
        (A) NAME/KEY: Modified-site
        (B) LOCATION: 16..18
        (D) OTHER INFORMATION: /note= "Where "Xaa"is a neutral, -continued positively charged, or negatively charged amino
acid."

( i x ) FEATURE:
    ( A ) NAME/KEY: Modified-site
    ( B ) LOCATION: 19
    ( D ) OTHER INFORMATION: /note= "Where "Xaa"is a positively
        charged or negatively charged amino acid."

( i x ) FEATURE:
    ( A ) NAME/KEY: Modified-site
    ( B ) LOCATION: 22
    ( D ) OTHER INFORMATION: /note= "Where "Xaa"is a positively
        charged or negatively charged amino acid."

( i x ) FEATURE:
    ( A ) NAME/KEY: Modified-site
    ( B ) LOCATION: 26..27
    ( D ) OTHER INFORMATION: /note= "Where "Xaa"is a positively
        charged amino acid."

( i x ) FEATURE:
    ( A ) NAME/KEY: Modified-site
    ( B ) LOCATION: 29..30
    ( D ) OTHER INFORMATION: /note= "Where "Xaa"is a neutral,
        positively charged, or negatively charged amino
        acid."

( i x ) FEATURE:
    ( A ) NAME/KEY: Modified-site
    ( B ) LOCATION: 32
    ( D ) OTHER INFORMATION: /note= "Where "Xaa"is a neutral or
        positively charged amino acid."

( i x ) FEATURE:
    ( A ) NAME/KEY: Modified-site
    ( B ) LOCATION: 33..34
    ( D ) OTHER INFORMATION: /note= "Where "Xaa"is a neutral,
        positively charged, or negatively charged amino
        acid."

( i x ) FEATURE:
    ( A ) NAME/KEY: Modified-site
    ( B ) LOCATION: 35
    ( D ) OTHER INFORMATION: /note= "Where "Xaa"is selected
        from the group consisting of Hol, Ho, a homoserine
        amide, or the sequence of amino acids comprising
        residues 35- 84 of PTH."

( x i ) SEQUENCE DESCRIPTION: SEQ ID NO:10:

| Ser | Val | Ser | Glu | Ile | Gln | Leu | Leu | His | Asn | Xaa | Xaa | Xaa | His | Xaa | Xaa |
|---|---|---|---|---|---|---|---|---|---|---|---|---|---|---|---|
| 1 | | | | 5 | | | | | 10 | | | | | 15 | |
| Xaa | Xaa | Xaa | Arg | Val | Xaa | Trp | Leu | Arg | Xaa | Xaa | Leu | Xaa | Xaa | Val | Xaa |
| | | | 20 | | | | | 25 | | | | | 30 | | |
| Xaa | Xaa | Xaa | | | | | | | | | | | | | |
| | | 35 | | | | | | | | | | | | | |

( 2 ) INFORMATION FOR SEQ ID NO:11:

( i ) SEQUENCE CHARACTERISTICS:
        ( A ) LENGTH: 35 amino acids
        ( B ) TYPE: amino acid
        ( D ) TOPOLOGY: unknown ( i i ) MOLECULE TYPE: protein ( i x ) FEATURE:
        ( A ) NAME/KEY: Modified-site
        ( B ) LOCATION: 35
        ( D ) OTHER INFORMATION: /note= "Where "Xaa"is selected
            from the group consisting of Hol, Ho, a homoserine
            amide, or the sequence of amino acids comprising
            residues 35- 84 of PTH."

( x i ) SEQUENCE DESCRIPTION: SEQ ID NO:11:

```
Lys  Val  Ser  Glu  Ile  Gln  Leu  Leu  His  Asn  Leu  Gly  Lys  His  Leu  Asn
1              5                        10                       15

Ser  Leu  Glu  Arg  Val  Glu  Trp  Leu  Arg  Lys  Lys  Leu  Gln  Asp  Val  His
               20                       25                       30

Asn  Tyr  Xaa
          35
```

( 2 ) INFORMATION FOR SEQ ID NO:12:

( i ) SEQUENCE CHARACTERISTICS:
        ( A ) LENGTH: 35 amino acids
        ( B ) TYPE: amino acid
        ( D ) TOPOLOGY: unknown ( i i ) MOLECULE TYPE: protein ( i x ) FEATURE:
        ( A ) NAME/KEY: Modified-site
        ( B ) LOCATION: 35
        ( D ) OTHER INFORMATION: /note= "Where "Xaa"is selected
            from the group consisting of Hol, Ho, a homoserine
            amide, or the sequence of amino acids comprising
            residues 35- 84 of PTH."

( x i ) SEQUENCE DESCRIPTION: SEQ ID NO:12:

```
Arg  Val  Ser  Glu  Ile  Gln  Leu  Leu  His  Asn  Leu  Gly  Lys  His  Leu  Asn
1              5                        10                       15

Ser  Leu  Glu  Arg  Val  Glu  Trp  Leu  Arg  Lys  Lys  Leu  Gln  Asp  Val  His
               20                       25                       30

Asn  Tyr  Xaa
          35
```

( 2 ) INFORMATION FOR SEQ ID NO:13:

( i ) SEQUENCE CHARACTERISTICS:
        ( A ) LENGTH: 35 amino acids
        ( B ) TYPE: amino acid
        ( D ) TOPOLOGY: unknown ( i i ) MOLECULE TYPE: protein ( i x ) FEATURE:
        ( A ) NAME/KEY: Modified-site
        ( B ) LOCATION: 35
        ( D ) OTHER INFORMATION: /note= "Where "Xaa"is selected
            from the group consisting of Hol, Ho, a homoserine
            amide, or the sequence of amino acids comprising
            residues 35- 84 of PTH."

( x i ) SEQUENCE DESCRIPTION: SEQ ID NO:13:

```
Glu  Val  Ser  Glu  Ile  Gln  Leu  Leu  His  Asn  Leu  Gly  Lys  His  Leu  Asn
1              5                        10                       15

Ser  Leu  Glu  Arg  Val  Glu  Trp  Leu  Arg  Lys  Lys  Leu  Gln  Asp  Val  His
               20                       25                       30

Asn  Tyr  Xaa
          35
```

( 2 ) INFORMATION FOR SEQ ID NO:14:

( i ) SEQUENCE CHARACTERISTICS:
        ( A ) LENGTH: 35 amino acids
        ( B ) TYPE: amino acid
        ( D ) TOPOLOGY: unknown ( i i ) MOLECULE TYPE: protein ( i x ) FEATURE:
        ( A ) NAME/KEY: Modified-site
        ( B ) LOCATION: 35

(D) OTHER INFORMATION: /note= "Where "Xaa"is selected from the group consisting of Hol, Ho, a homoserine amide, or the sequence of amino acids comprising residues 35- 84 of PTH."

(x i) SEQUENCE DESCRIPTION: SEQ ID NO:14:

| Gly | Val | Ser | Glu | Ile | Gln | Leu | Leu | His | Asn | Leu | Gly | Lys | His | Leu | Asn |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ser | Leu | Glu | Arg | Val | Glu | Trp | Leu | Arg | Lys | Lys | Leu | Gln | Asp | Val | His |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

Asn Tyr Xaa
         35

(2) INFORMATION FOR SEQ ID NO:15:

(i) SEQUENCE CHARACTERISTICS:
    (A) LENGTH: 35 amino acids
    (B) TYPE: amino acid
    (D) TOPOLOGY: unknown (i i) MOLECULE TYPE: protein (i x) FEATURE:
    (A) NAME/KEY: Modified-site
    (B) LOCATION: 35
    (D) OTHER INFORMATION: /note= "Where "Xaa"is selected from the group consisting of Hol, Ho, a homoserine amide, or the sequence of amino acids comprising residues 35- 84 of PTH."

(x i) SEQUENCE DESCRIPTION: SEQ ID NO:15:

| Ser | Arg | Ser | Glu | Ile | Gln | Leu | Leu | His | Asn | Leu | Gly | Lys | His | Leu | Asn |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ser | Leu | Glu | Arg | Val | Glu | Trp | Leu | Arg | Lys | Lys | Leu | Gln | Asp | Val | His |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

Asn Tyr Xaa
         35

(2) INFORMATION FOR SEQ ID NO:16:

(i) SEQUENCE CHARACTERISTICS:
    (A) LENGTH: 35 amino acids
    (B) TYPE: amino acid
    (D) TOPOLOGY: unknown (i i) MOLECULE TYPE: protein (i x) FEATURE:
    (A) NAME/KEY: Modified-site
    (B) LOCATION: 35
    (D) OTHER INFORMATION: /note= "Where "Xaa"is selected from the group consisting of Hol, Ho, a homoserine amide, or the sequence of amino acids comprising residues 35- 84 of PTH."

(x i) SEQUENCE DESCRIPTION: SEQ ID NO:16:

| Ser | Glu | Ser | Glu | Ile | Gln | Leu | Leu | His | Asn | Leu | Gly | Lys | His | Leu | Asn |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ser | Leu | Glu | Arg | Val | Glu | Trp | Leu | Arg | Lys | Lys | Leu | Gln | Asp | Val | His |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

Asn Tyr Xaa
         35

(2) INFORMATION FOR SEQ ID NO:17:

(i) SEQUENCE CHARACTERISTICS:
    (A) LENGTH: 35 amino acids
    (B) TYPE: amino acid (D) TOPOLOGY: unknown (i i) MOLECULE TYPE: protein (i x) FEATURE:
(A) NAME/KEY: Modified-site
(B) LOCATION: 35
(D) OTHER INFORMATION: /note= "Where "Xaa"is selected from the group consisting of Hol, Ho, a homoserine amide, or the sequence of amino acids comprising residues 35- 84 of PTH."

(x i) SEQUENCE DESCRIPTION: SEQ ID NO:17:

| Ser | Gly | Ser | Glu | Ile | Gln | Leu | Leu | His | Asn | Leu | Gly | Lys | His | Leu | Asn |
|---|---|---|---|---|---|---|---|---|---|---|---|---|---|---|---|
| 1 | | | | 5 | | | | | 10 | | | | | 15 | |

| Ser | Leu | Glu | Arg | Val | Glu | Trp | Leu | Arg | Lys | Lys | Leu | Gln | Asp | Val | His |
|---|---|---|---|---|---|---|---|---|---|---|---|---|---|---|---|
| | | | 20 | | | | | 25 | | | | | 30 | | |

| Asn | Tyr | Xaa |
|---|---|---|
| | | 35 |

(2) INFORMATION FOR SEQ ID NO:18:

(i) SEQUENCE CHARACTERISTICS:
(A) LENGTH: 35 amino acids
(B) TYPE: amino acid
(D) TOPOLOGY: unknown (i i) MOLECULE TYPE: protein (i x) FEATURE:
(A) NAME/KEY: Modified-site
(B) LOCATION: 35
(D) OTHER INFORMATION: /note= "Where "Xaa"is selected from the group consisting of Hol, Ho, a homoserine amide, or the sequence of amino acids comprising residues 35- 84 of PTH."

(x i) SEQUENCE DESCRIPTION: SEQ ID NO:18:

| Ser | Val | Lys | Glu | Ile | Gln | Leu | Leu | His | Asn | Leu | Gly | Lys | His | Leu | Asn |
|---|---|---|---|---|---|---|---|---|---|---|---|---|---|---|---|
| 1 | | | | 5 | | | | | 10 | | | | | 15 | |

| Ser | Leu | Glu | Arg | Val | Glu | Trp | Leu | Arg | Lys | Lys | Leu | Gln | Asp | Val | His |
|---|---|---|---|---|---|---|---|---|---|---|---|---|---|---|---|
| | | | 20 | | | | | 25 | | | | | 30 | | |

| Asn | Tyr | Xaa |
|---|---|---|
| | | 35 |

(2) INFORMATION FOR SEQ ID NO:19:

(i) SEQUENCE CHARACTERISTICS:
(A) LENGTH: 35 amino acids
(B) TYPE: amino acid
(D) TOPOLOGY: unknown (i i) MOLECULE TYPE: protein (i x) FEATURE:
(A) NAME/KEY: Modified-site
(B) LOCATION: 35
(D) OTHER INFORMATION: /note= "Where "Xaa"is selected from the group consisting of Hol, Ho, a homoserine amide, or the sequence of amino acids comprising residues 35- 84 of PTH."

(x i) SEQUENCE DESCRIPTION: SEQ ID NO:19:

| Ser | Val | Arg | Glu | Ile | Gln | Leu | Leu | His | Asn | Leu | Gly | Lys | His | Leu | Asn |
|---|---|---|---|---|---|---|---|---|---|---|---|---|---|---|---|
| 1 | | | | 5 | | | | | 10 | | | | | 15 | |

| Ser | Leu | Glu | Arg | Val | Glu | Trp | Leu | Arg | Lys | Lys | Leu | Gln | Asp | Val | His |
|---|---|---|---|---|---|---|---|---|---|---|---|---|---|---|---|
| | | | 20 | | | | | 25 | | | | | 30 | | |

| Asn | Tyr | Xaa |
|---|---|---|
| | | 35 |

( 2 ) INFORMATION FOR SEQ ID NO:20:

( i ) SEQUENCE CHARACTERISTICS:
      ( A ) LENGTH: 35 amino acids
      ( B ) TYPE: amino acid
      ( D ) TOPOLOGY: unknown ( i i ) MOLECULE TYPE: protein ( i x ) FEATURE:
      ( A ) NAME/KEY: Modified-site
      ( B ) LOCATION: 35
      ( D ) OTHER INFORMATION: /note= "Where "Xaa"is selected
         from the group consisting of Hol, Ho, a homoserine
         amide, or the sequence of amino acids comprising
         residues 35- 84 of PTH."

( x i ) SEQUENCE DESCRIPTION: SEQ ID NO:20:

```
Ser  Val  Glu  Glu  Ile  Gln  Leu  Leu  His  Asn  Leu  Gly  Lys  His  Leu  Asn
1                   5                        10                       15
Ser  Leu  Glu  Arg  Val  Glu  Trp  Leu  Arg  Lys  Lys  Leu  Gln  Asp  Val  His
               20                  25                       30
Asn  Tyr  Xaa
          35
```

( 2 ) INFORMATION FOR SEQ ID NO:21:

( i ) SEQUENCE CHARACTERISTICS:
      ( A ) LENGTH: 35 amino acids
      ( B ) TYPE: amino acid
      ( D ) TOPOLOGY: unknown ( i i ) MOLECULE TYPE: protein ( i x ) FEATURE:
      ( A ) NAME/KEY: Modified-site
      ( B ) LOCATION: 35
      ( D ) OTHER INFORMATION: /note= "Where "Xaa"is selected
         from the group consisting of Hol, Ho, a homoserine
         amide, or the sequence of amino acids comprising
         residues 35- 84 of PTH."

( x i ) SEQUENCE DESCRIPTION: SEQ ID NO:21:

```
Ser  Val  Gly  Glu  Ile  Gln  Leu  Leu  His  Asn  Leu  Gly  Lys  His  Leu  Asn
1                   5                        10                       15
Ser  Leu  Glu  Arg  Val  Glu  Trp  Leu  Arg  Lys  Lys  Leu  Gln  Asp  Val  His
               20                  25                       30
Asn  Tyr  Xaa
          35
```

( 2 ) INFORMATION FOR SEQ ID NO:22:

( i ) SEQUENCE CHARACTERISTICS:
      ( A ) LENGTH: 35 amino acids
      ( B ) TYPE: amino acid
      ( D ) TOPOLOGY: unknown ( i i ) MOLECULE TYPE: protein ( i x ) FEATURE:
      ( A ) NAME/KEY: Modified-site
      ( B ) LOCATION: 35
      ( D ) OTHER INFORMATION: /note= "Where "Xaa"is selected
         from the group consisting of Hol, Ho, a homoserine
         amide, or the sequence of amino acids comprising
         residues 35- 84 of PTH."

( x i ) SEQUENCE DESCRIPTION: SEQ ID NO:22:

```
Ser  Val  Ser  Arg  Ile  Gln  Leu  Leu  His  Asn  Leu  Gly  Lys  His  Leu  Asn
```

```
        1               5                  10                    15
Ser Leu Glu Arg Val Glu Trp Leu Arg Lys Lys Leu Gln Asp Val His
                20                  25                  30

Asn Tyr Xaa
        35
```

(2) INFORMATION FOR SEQ ID NO:23:

(i) SEQUENCE CHARACTERISTICS:
        (A) LENGTH: 35 amino acids
        (B) TYPE: amino acid
        (D) TOPOLOGY: unknown (ii) MOLECULE TYPE: protein (ix) FEATURE:
        (A) NAME/KEY: Modified-site
        (B) LOCATION: 35
        (D) OTHER INFORMATION: /note= "Where "Xaa"is selected
            from the group consisting of Hol, Ho, a homoserine
            amide, or the sequence of amino acids comprising
            residues 35- 84 of PTH."

(xi) SEQUENCE DESCRIPTION: SEQ ID NO:23:

```
Ser Val Ser Glu Ile Gln Leu Leu His Asn Leu Gly Lys His Leu Asn
1               5                  10                    15
Ser Leu Glu Arg Val Glu Trp Leu Arg Lys Lys Leu Gln Asp Val His
                20                  25                  30
Asn Tyr Xaa
        35
```

(2) INFORMATION FOR SEQ ID NO:24:

(i) SEQUENCE CHARACTERISTICS:
        (A) LENGTH: 35 amino acids
        (B) TYPE: amino acid
        (D) TOPOLOGY: unknown (ii) MOLECULE TYPE: protein (ix) FEATURE:
        (A) NAME/KEY: Modified-site
        (B) LOCATION: 35
        (D) OTHER INFORMATION: /note= "Where "Xaa"is selected
            from the group consisting of Hol, Ho, a homoserine
            amide, or the sequence of amino acids comprising
            residues 35- 84 of PTH."

(xi) SEQUENCE DESCRIPTION: SEQ ID NO:24:

```
Ser Val Ser Gly Ile Gln Leu Leu His Asn Leu Gly Lys His Leu Asn
1               5                  10                    15
Ser Leu Glu Arg Val Glu Trp Leu Arg Lys Lys Leu Gln Asp Val His
                20                  25                  30
Asn Tyr Xaa
        35
```

(2) INFORMATION FOR SEQ ID NO:25:

(i) SEQUENCE CHARACTERISTICS:
        (A) LENGTH: 35 amino acids
        (B) TYPE: amino acid
        (D) TOPOLOGY: unknown (ii) MOLECULE TYPE: protein (ix) FEATURE:
        (A) NAME/KEY: Modified-site
        (B) LOCATION: 35
        (D) OTHER INFORMATION: /note= "Where "Xaa"is selected from the group consisting of Hol, Ho, a homoserine
amide, or the sequence of amino acids comprising
residues 35- 84 of PTH."

( x i ) SEQUENCE DESCRIPTION: SEQ ID NO:25:

| Ser | Val | Ser | Glu | Lys | Gln | Leu | Leu | His | Asn | Leu | Gly | Lys | His | Leu | Asn |
|---|---|---|---|---|---|---|---|---|---|---|---|---|---|---|---|
| 1 | | | | 5 | | | | | 10 | | | | | | 15 |

| Ser | Leu | Glu | Arg | Val | Glu | Trp | Leu | Arg | Lys | Lys | Leu | Gln | Asp | Val | His |
|---|---|---|---|---|---|---|---|---|---|---|---|---|---|---|---|
| | | | 20 | | | | | 25 | | | | | 30 | | |

| Asn | Tyr | Xaa |
|---|---|---|
| | | 35 |

( 2 ) INFORMATION FOR SEQ ID NO:26:

( i ) SEQUENCE CHARACTERISTICS:
        ( A ) LENGTH: 35 amino acids
        ( B ) TYPE: amino acid
        ( D ) TOPOLOGY: unknown ( i i ) MOLECULE TYPE: protein ( i x ) FEATURE:
        ( A ) NAME/KEY: Modified-site
        ( B ) LOCATION: 35
        ( D ) OTHER INFORMATION: /note= "Where "Xaa"is selected
from the group consisting of Hol, Ho, a homoserine
amide, or the sequence of amino acids comprising
residues 35- 84 of PTH."

( x i ) SEQUENCE DESCRIPTION: SEQ ID NO:26:

| Ser | Val | Ser | Glu | Arg | Gln | Leu | Leu | His | Asn | Leu | Gly | Lys | His | Leu | Asn |
|---|---|---|---|---|---|---|---|---|---|---|---|---|---|---|---|
| 1 | | | | 5 | | | | | 10 | | | | | | 15 |

| Ser | Leu | Glu | Arg | Val | Glu | Trp | Leu | Arg | Lys | Lys | Leu | Gln | Asp | Val | His |
|---|---|---|---|---|---|---|---|---|---|---|---|---|---|---|---|
| | | | 20 | | | | | 25 | | | | | 30 | | |

| Asn | Tyr | Xaa |
|---|---|---|
| | | 35 |

( 2 ) INFORMATION FOR SEQ ID NO:27:

( i ) SEQUENCE CHARACTERISTICS:
        ( A ) LENGTH: 35 amino acids
        ( B ) TYPE: amino acid
        ( D ) TOPOLOGY: unknown ( i i ) MOLECULE TYPE: protein ( i x ) FEATURE:
        ( A ) NAME/KEY: Modified-site
        ( B ) LOCATION: 35
        ( D ) OTHER INFORMATION: /note= "Where "Xaa"is selected
from the group consisting of Hol, Ho, a homoserine
amide, or the sequence of amino acids comprising
residues 35- 84 of PTH."

( x i ) SEQUENCE DESCRIPTION: SEQ ID NO:27:

| Ser | Val | Ser | Glu | Glu | Gln | Leu | Leu | His | Asn | Leu | Gly | Lys | His | Leu | Asn |
|---|---|---|---|---|---|---|---|---|---|---|---|---|---|---|---|
| 1 | | | | 5 | | | | | 10 | | | | | | 15 |

| Ser | Leu | Glu | Arg | Val | Glu | Trp | Leu | Arg | Lys | Lys | Leu | Gln | Asp | Val | His |
|---|---|---|---|---|---|---|---|---|---|---|---|---|---|---|---|
| | | | 20 | | | | | 25 | | | | | 30 | | |

| Asn | Tyr | Xaa |
|---|---|---|
| | | 35 |

( 2 ) INFORMATION FOR SEQ ID NO:28:

( i ) SEQUENCE CHARACTERISTICS:
        ( A ) LENGTH: 35 amino acids
        ( B ) TYPE: amino acid
        ( D ) TOPOLOGY: unknown ( i i ) MOLECULE TYPE: protein ( i x ) FEATURE:
(A) NAME/KEY: Modified-site
(B) LOCATION: 35
(D) OTHER INFORMATION: /note= "Where "Xaa"is selected from the group consisting of Hol, Ho, a homoserine amide, or the sequence of amino acids comprising residues 35- 84 of PTH."

( x i ) SEQUENCE DESCRIPTION: SEQ ID NO:28:

| Ser | Val | Ser | Glu | Gly | Gln | Leu | Leu | His | Asn | Leu | Gly | Lys | His | Leu | Asn |
|---|---|---|---|---|---|---|---|---|---|---|---|---|---|---|---|
| 1 | | | | 5 | | | | | 10 | | | | | 15 | |
| Ser | Leu | Glu | Arg | Val | Glu | Trp | Leu | Arg | Lys | Lys | Leu | Gln | Asp | Val | His |
| | | | 20 | | | | | 25 | | | | | 30 | | |
| Asn | Tyr | Xaa | | | | | | | | | | | | | |
| | | 35 | | | | | | | | | | | | | |

( 2 ) INFORMATION FOR SEQ ID NO:29:

( i ) SEQUENCE CHARACTERISTICS:
(A) LENGTH: 35 amino acids
(B) TYPE: amino acid
(D) TOPOLOGY: unknown ( i i ) MOLECULE TYPE: protein ( i x ) FEATURE:
(A) NAME/KEY: Modified-site
(B) LOCATION: 35
(D) OTHER INFORMATION: /note= "Where "Xaa"is selected from the group consisting of Hol, Ho, a homoserine amide, or the sequence of amino acids comprising residues 35- 84 of PTH."

( x i ) SEQUENCE DESCRIPTION: SEQ ID NO:29:

| Ser | Val | Ser | Glu | Ile | Arg | Leu | Leu | His | Asn | Leu | Gly | Lys | His | Leu | Asn |
|---|---|---|---|---|---|---|---|---|---|---|---|---|---|---|---|
| 1 | | | | 5 | | | | | 10 | | | | | 15 | |
| Ser | Leu | Glu | Arg | Val | Glu | Trp | Leu | Arg | Lys | Lys | Leu | Gln | Asp | Val | His |
| | | | 20 | | | | | 25 | | | | | 30 | | |
| Asn | Tyr | Xaa | | | | | | | | | | | | | |
| | | 35 | | | | | | | | | | | | | |

( 2 ) INFORMATION FOR SEQ ID NO:30:

( i ) SEQUENCE CHARACTERISTICS:
(A) LENGTH: 35 amino acids
(B) TYPE: amino acid
(D) TOPOLOGY: unknown ( i i ) MOLECULE TYPE: protein ( i x ) FEATURE:
(A) NAME/KEY: Modified-site
(B) LOCATION: 35
(D) OTHER INFORMATION: /note= "Where "Xaa"is selected from the group consisting of Hol, Ho, a homoserine amide, or the sequence of amino acids comprising residues 35- 84 of PTH."

( x i ) SEQUENCE DESCRIPTION: SEQ ID NO:30:

| Ser | Val | Ser | Glu | Ile | Glu | Leu | Leu | His | Asn | Leu | Gly | Lys | His | Leu | Asn |
|---|---|---|---|---|---|---|---|---|---|---|---|---|---|---|---|
| 1 | | | | 5 | | | | | 10 | | | | | 15 | |
| Ser | Leu | Glu | Arg | Val | Glu | Trp | Leu | Arg | Lys | Lys | Leu | Gln | Asp | Val | His |
| | | | 20 | | | | | 25 | | | | | 30 | | |
| Asn | Tyr | Xaa | | | | | | | | | | | | | |
| | | 35 | | | | | | | | | | | | | |

( 2 ) INFORMATION FOR SEQ ID NO:31:

( i ) SEQUENCE CHARACTERISTICS:
        ( A ) LENGTH: 35 amino acids
        ( B ) TYPE: amino acid
        ( D ) TOPOLOGY: unknown ( i i ) MOLECULE TYPE: protein ( i x ) FEATURE:
        ( A ) NAME/KEY: Modified-site
        ( B ) LOCATION: 35
        ( D ) OTHER INFORMATION: /note= "Where "Xaa"is selected
            from the group consisting of Hol, Ho, a homoserine
            amide, or the sequence of amino acids comprising
            residues 35- 84 of PTH."

( x i ) SEQUENCE DESCRIPTION: SEQ ID NO:31:

```
Ser  Val  Ser  Glu  Ile  Gln  Lys  Leu  His  Asn  Leu  Gly  Lys  His  Leu  Asn
 1              5                        10                            15
Ser  Leu  Glu  Arg  Val  Glu  Trp  Leu  Arg  Lys  Lys  Leu  Gln  Asp  Val  His
               20                        25                       30
Asn  Tyr  Xaa
          35
```

( 2 ) INFORMATION FOR SEQ ID NO:32:

( i ) SEQUENCE CHARACTERISTICS:
        ( A ) LENGTH: 35 amino acids
        ( B ) TYPE: amino acid
        ( D ) TOPOLOGY: unknown ( i i ) MOLECULE TYPE: protein ( i x ) FEATURE:
        ( A ) NAME/KEY: Modified-site
        ( B ) LOCATION: 35
        ( D ) OTHER INFORMATION: /note= "Where "Xaa"is selected
            from the group consisting of Hol, Ho, a homoserine
            amide, or the sequence of amino acids comprising
            residues 35- 84 of PTH."

( x i ) SEQUENCE DESCRIPTION: SEQ ID NO:32:

```
Ser  Val  Ser  Glu  Ile  Gln  Arg  Leu  His  Asn  Leu  Gly  Lys  His  Leu  Asn
 1              5                        10                            15
Ser  Leu  Glu  Arg  Val  Glu  Trp  Leu  Arg  Lys  Lys  Leu  Gln  Asp  Val  His
               20                        25                       30
Asn  Tyr  Xaa
          35
```

( 2 ) INFORMATION FOR SEQ ID NO:33:

( i ) SEQUENCE CHARACTERISTICS:
        ( A ) LENGTH: 35 amino acids
        ( B ) TYPE: amino acid
        ( D ) TOPOLOGY: unknown ( i i ) MOLECULE TYPE: protein ( i x ) FEATURE:
        ( A ) NAME/KEY: Modified-site
        ( B ) LOCATION: 35
        ( D ) OTHER INFORMATION: /note= "Where "Xaa"is selected
            from the group consisting of Hol, Ho, a homoserine
            amide, or the sequence of amino acids comprising
            residues 35- 84 of PTH."

( x i ) SEQUENCE DESCRIPTION: SEQ ID NO:33:

```
Ser  Val  Ser  Glu  Ile  Gln  Glu  Leu  His  Asn  Leu  Gly  Lys  His  Leu  Asn
 1              5                        10                            15
```

```
                Ser  Leu  Glu  Arg  Val  Glu  Trp  Leu  Arg  Lys  Lys  Leu  Gln  Asp  Val  His
                               20                      25                      30

Asn  Tyr  Xaa
                          35
```

( 2 ) INFORMATION FOR SEQ ID NO:34:

( i ) SEQUENCE CHARACTERISTICS:
        ( A ) LENGTH: 35 amino acids
        ( B ) TYPE: amino acid
        ( D ) TOPOLOGY: unknown ( i i ) MOLECULE TYPE: protein ( i x ) FEATURE:
        ( A ) NAME/KEY: Modified-site
        ( B ) LOCATION: 35
        ( D ) OTHER INFORMATION: /note= "Where "Xaa"is selected
            from the group consisting of Hol, Ho, a homoserine
            amide, or the sequence of amino acids comprising
            residues 35- 84 of PTH."

( x i ) SEQUENCE DESCRIPTION: SEQ ID NO:34:

```
                Ser  Val  Ser  Glu  Ile  Gln  Gly  Leu  His  Asn  Leu  Gly  Lys  His  Leu  Asn
                1                   5                      10                      15

Ser  Leu  Glu  Arg  Val  Glu  Trp  Leu  Arg  Lys  Lys  Leu  Gln  Asp  Val  His
                               20                      25                      30

Asn  Tyr  Xaa
                          35
```

( 2 ) INFORMATION FOR SEQ ID NO:35:

( i ) SEQUENCE CHARACTERISTICS:
        ( A ) LENGTH: 35 amino acids
        ( B ) TYPE: amino acid
        ( D ) TOPOLOGY: unknown ( i i ) MOLECULE TYPE: protein ( i x ) FEATURE:
        ( A ) NAME/KEY: Modified-site
        ( B ) LOCATION: 35
        ( D ) OTHER INFORMATION: /note= "Where "Xaa"is selected
            from the group consisting of Hol, Ho, a homoserine
            amide, or the sequence of amino acids comprising
            residues 35- 84 of PTH."

( x i ) SEQUENCE DESCRIPTION: SEQ ID NO:35:

```
                Ser  Val  Ser  Glu  Ile  Gln  Leu  Lys  His  Asn  Leu  Gly  Lys  His  Leu  Asn
                1                   5                      10                      15

Ser  Leu  Glu  Arg  Val  Glu  Trp  Leu  Arg  Lys  Lys  Leu  Gln  Asp  Val  His
                               20                      25                      30

Asn  Tyr  Xaa
                          35
```

( 2 ) INFORMATION FOR SEQ ID NO:36:

( i ) SEQUENCE CHARACTERISTICS:
        ( A ) LENGTH: 35 amino acids
        ( B ) TYPE: amino acid
        ( D ) TOPOLOGY: unknown ( i i ) MOLECULE TYPE: protein ( i x ) FEATURE:
        ( A ) NAME/KEY: Modified-site
        ( B ) LOCATION: 35
        ( D ) OTHER INFORMATION: /note= "Where "Xaa"is selected
            from the group consisting of Hol, Ho, a homoserine amide, or the sequence of amino acids comprising residues 35-84 of PTH."

( x i ) SEQUENCE DESCRIPTION: SEQ ID NO:36:

| Ser | Val | Ser | Glu | Ile | Gln | Leu | Glu | His | Asn | Leu | Gly | Lys | His | Leu | Asn |
|---|---|---|---|---|---|---|---|---|---|---|---|---|---|---|---|
| 1 | | | | 5 | | | | | 10 | | | | | 15 | |
| Ser | Leu | Glu | Arg | Val | Glu | Trp | Leu | Arg | Lys | Lys | Leu | Gln | Asp | Val | His |
| | | | 20 | | | | | 25 | | | | | 30 | | |
| Asn | Tyr | Xaa | | | | | | | | | | | | | |
| | | 35 | | | | | | | | | | | | | |

( 2 ) INFORMATION FOR SEQ ID NO:37:

( i ) SEQUENCE CHARACTERISTICS:
      ( A ) LENGTH: 35 amino acids
      ( B ) TYPE: amino acid
      ( D ) TOPOLOGY: unknown ( i i ) MOLECULE TYPE: protein ( i x ) FEATURE:
      ( A ) NAME/KEY: Modified-site
      ( B ) LOCATION: 35
      ( D ) OTHER INFORMATION: /note= "Where "Xaa"is selected from the group consisting of Hol, Ho, a homoserine amide, or the sequence of amino acids comprising residues 35-84 of PTH."

( x i ) SEQUENCE DESCRIPTION: SEQ ID NO:37:

| Ser | Val | Ser | Glu | Ile | Gln | Leu | Gly | His | Asn | Leu | Gly | Lys | His | Leu | Asn |
|---|---|---|---|---|---|---|---|---|---|---|---|---|---|---|---|
| 1 | | | | 5 | | | | | 10 | | | | | 15 | |
| Ser | Leu | Glu | Arg | Val | Glu | Trp | Leu | Arg | Lys | Lys | Leu | Gln | Asp | Val | His |
| | | | 20 | | | | | 25 | | | | | 30 | | |
| Asn | Tyr | Xaa | | | | | | | | | | | | | |
| | | 35 | | | | | | | | | | | | | |

( 2 ) INFORMATION FOR SEQ ID NO:38:

( i ) SEQUENCE CHARACTERISTICS:
      ( A ) LENGTH: 35 amino acids
      ( B ) TYPE: amino acid
      ( D ) TOPOLOGY: unknown ( i i ) MOLECULE TYPE: protein ( i x ) FEATURE:
      ( A ) NAME/KEY: Modified-site
      ( B ) LOCATION: 35
      ( D ) OTHER INFORMATION: /note= "Where "Xaa"is selected from the group consisting of Hol, Ho, a homoserine amide, or the sequence of amino acids comprising residues 35-84 of PTH."

( x i ) SEQUENCE DESCRIPTION: SEQ ID NO:38:

| Ser | Val | Ser | Glu | Ile | Gln | Leu | Leu | Lys | Asn | Leu | Gly | Lys | His | Leu | Asn |
|---|---|---|---|---|---|---|---|---|---|---|---|---|---|---|---|
| 1 | | | | 5 | | | | | 10 | | | | | 15 | |
| Ser | Leu | Glu | Arg | Val | Glu | Trp | Leu | Arg | Lys | Lys | Leu | Gln | Asp | Val | His |
| | | | 20 | | | | | 25 | | | | | 30 | | |
| Asn | Tyr | Xaa | | | | | | | | | | | | | |
| | | 35 | | | | | | | | | | | | | |

( 2 ) INFORMATION FOR SEQ ID NO:39:

( i ) SEQUENCE CHARACTERISTICS:
      ( A ) LENGTH: 35 amino acids
      ( B ) TYPE: amino acid
      ( D ) TOPOLOGY: unknown (i i) MOLECULE TYPE: protein (i x) FEATURE:
    (A) NAME/KEY: Modified-site
    (B) LOCATION: 35
    (D) OTHER INFORMATION: /note= "Where "Xaa"is selected from the group consisting of Hol, Ho, a homoserine amide, or the sequence of amino acids comprising residues 35- 84 of PTH."

(x i) SEQUENCE DESCRIPTION: SEQ ID NO:39:

| Ser | Val | Ser | Glu | Ile | Gln | Leu | Leu | Glu | Asn | Leu | Gly | Lys | His | Leu | Asn |
|---|---|---|---|---|---|---|---|---|---|---|---|---|---|---|---|
| 1 | | | | 5 | | | | | 10 | | | | | 15 | |
| Ser | Leu | Glu | Arg | Val | Glu | Trp | Leu | Arg | Lys | Lys | Leu | Gln | Asp | Val | His |
| | | | 20 | | | | | 25 | | | | | 30 | | |
| Asn | Tyr | Xaa | | | | | | | | | | | | | |
| | | 35 | | | | | | | | | | | | | |

(2) INFORMATION FOR SEQ ID NO:40:

(i) SEQUENCE CHARACTERISTICS:
        (A) LENGTH: 35 amino acids
        (B) TYPE: amino acid
        (D) TOPOLOGY: unknown (i i) MOLECULE TYPE: protein (i x) FEATURE:
        (A) NAME/KEY: Modified-site
        (B) LOCATION: 35
        (D) OTHER INFORMATION: /note= "Where "Xaa"is selected from the group consisting of Hol, Ho, a homoserine amide, or the sequence of amino acids comprising residues 35- 84 of PTH."

(x i) SEQUENCE DESCRIPTION: SEQ ID NO:40:

| Ser | Val | Ser | Glu | Ile | Gln | Leu | Leu | Gly | Asn | Leu | Gly | Lys | His | Leu | Asn |
|---|---|---|---|---|---|---|---|---|---|---|---|---|---|---|---|
| 1 | | | | 5 | | | | | 10 | | | | | 15 | |
| Ser | Leu | Glu | Arg | Val | Glu | Trp | Leu | Arg | Lys | Lys | Leu | Gln | Asp | Val | His |
| | | | 20 | | | | | 25 | | | | | 30 | | |
| Asn | Tyr | Xaa | | | | | | | | | | | | | |
| | | 35 | | | | | | | | | | | | | |

(2) INFORMATION FOR SEQ ID NO:41:

(i) SEQUENCE CHARACTERISTICS:
        (A) LENGTH: 35 amino acids
        (B) TYPE: amino acid
        (D) TOPOLOGY: unknown (i i) MOLECULE TYPE: protein (i x) FEATURE:
        (A) NAME/KEY: Modified-site
        (B) LOCATION: 35
        (D) OTHER INFORMATION: /note= "Where "Xaa"is selected from the group consisting of Hol, Ho, a homoserine amide, or the sequence of amino acids comprising residues 35- 84 of PTH."

(x i) SEQUENCE DESCRIPTION: SEQ ID NO:41:

| Ser | Val | Ser | Glu | Ile | Gln | Leu | Leu | His | Arg | Leu | Gly | Lys | His | Leu | Asn |
|---|---|---|---|---|---|---|---|---|---|---|---|---|---|---|---|
| 1 | | | | 5 | | | | | 10 | | | | | 15 | |
| Ser | Leu | Glu | Arg | Val | Glu | Trp | Leu | Arg | Lys | Lys | Leu | Gln | Asp | Val | His |
| | | | 20 | | | | | 25 | | | | | 30 | | |
| Asn | Tyr | Xaa | | | | | | | | | | | | | |
| | | 35 | | | | | | | | | | | | | |

( 2 ) INFORMATION FOR SEQ ID NO:42:

( i ) SEQUENCE CHARACTERISTICS:
        ( A ) LENGTH: 35 amino acids
        ( B ) TYPE: amino acid
        ( D ) TOPOLOGY: unknown ( i i ) MOLECULE TYPE: protein ( i x ) FEATURE:
        ( A ) NAME/KEY: Modified-site
        ( B ) LOCATION: 35
        ( D ) OTHER INFORMATION: /note= "Where "Xaa"is selected
            from the group consisting of Hol, Ho, a homoserine
            amide, or the sequence of amino acids comprising
            residues 35- 84 of PTH."

( x i ) SEQUENCE DESCRIPTION: SEQ ID NO:42:

Ser Val Ser Glu Ile Gln Leu Leu His Glu Leu Gly Lys His Leu Asn
1               5                   1 0                 1 5

Ser Leu Glu Arg Val Glu Trp Leu Arg Lys Lys Leu Gln Asp Val His
            2 0                 2 5                 3 0

Asn Tyr Xaa
        3 5

( 2 ) INFORMATION FOR SEQ ID NO:43:

( i ) SEQUENCE CHARACTERISTICS:
        ( A ) LENGTH: 35 amino acids
        ( B ) TYPE: amino acid
        ( D ) TOPOLOGY: unknown ( i i ) MOLECULE TYPE: protein ( i x ) FEATURE:
        ( A ) NAME/KEY: Modified-site
        ( B ) LOCATION: 35
        ( D ) OTHER INFORMATION: /note= "Where "Xaa"is selected
            from the group consisting of Hol, Ho, a homoserine
            amide, or the sequence of amino acids comprising
            residues 35- 84 of PTH."

( x i ) SEQUENCE DESCRIPTION: SEQ ID NO:43:

Ser Val Ser Glu Ile Gln Leu Leu His Gly Leu Gly Lys His Leu Asn
1               5                   1 0                 1 5

Ser Leu Glu Arg Val Glu Trp Leu Arg Lys Lys Leu Gln Asp Val His
            2 0                 2 5                 3 0

Asn Tyr Xaa
        3 5

( 2 ) INFORMATION FOR SEQ ID NO:44:

( i ) SEQUENCE CHARACTERISTICS:
        ( A ) LENGTH: 35 amino acids
        ( B ) TYPE: amino acid
        ( D ) TOPOLOGY: unknown ( i i ) MOLECULE TYPE: protein ( i x ) FEATURE:
        ( A ) NAME/KEY: Modified-site
        ( B ) LOCATION: 35
        ( D ) OTHER INFORMATION: /note= "Where "Xaa"is selected
            from the group consisting of Hol, Ho, a homoserine
            amide, or the sequence of amino acids comprising
            residues 35- 84 of PTH."

( x i ) SEQUENCE DESCRIPTION: SEQ ID NO:44:

Ser Val Ser Glu Ile Gln Leu Leu His Asn Arg Gly Lys His Leu Asn
1               5                   1 0                 1 5

```
Ser  Leu  Glu  Arg  Val  Glu  Trp  Leu  Arg  Lys  Lys  Leu  Gln  Asp  Val  His
               20                  25                       30

Asn  Tyr  Xaa
          35
```

( 2 ) INFORMATION FOR SEQ ID NO:45:

( i ) SEQUENCE CHARACTERISTICS:
        ( A ) LENGTH: 35 amino acids
        ( B ) TYPE: amino acid
        ( D ) TOPOLOGY: unknown ( i i ) MOLECULE TYPE: protein ( i x ) FEATURE:
        ( A ) NAME/KEY: Modified-site
        ( B ) LOCATION: 35
        ( D ) OTHER INFORMATION: /note= "Where "Xaa"is selected
            from the group consisting of Hol, Ho, a homoserine
            amide, or the sequence of amino acids comprising
            residues 35- 84 of PTH."

( x i ) SEQUENCE DESCRIPTION: SEQ ID NO:45:

```
Ser  Val  Ser  Glu  Ile  Gln  Leu  Leu  His  Asn  Glu  Gly  Lys  His  Leu  Asn
1                    5                        10                       15

Ser  Leu  Glu  Arg  Val  Glu  Trp  Leu  Arg  Lys  Lys  Leu  Gln  Asp  Val  His
               20                  25                       30

Asn  Tyr  Xaa
          35
```

( 2 ) INFORMATION FOR SEQ ID NO:46:

( i ) SEQUENCE CHARACTERISTICS:
        ( A ) LENGTH: 35 amino acids
        ( B ) TYPE: amino acid
        ( D ) TOPOLOGY: unknown ( i i ) MOLECULE TYPE: protein ( i x ) FEATURE:
        ( A ) NAME/KEY: Modified-site
        ( B ) LOCATION: 35
        ( D ) OTHER INFORMATION: /note= "Where "Xaa"is selected
            from the group consisting of Hol, Ho, a homoserine
            amide, or the sequence of amino acids comprising
            residues 35- 84 of PTH."

( x i ) SEQUENCE DESCRIPTION: SEQ ID NO:46:

```
Ser  Val  Ser  Glu  Ile  Gln  Leu  Leu  His  Asn  Gly  Gly  Lys  His  Leu  Asn
1                    5                        10                       15

Ser  Leu  Glu  Arg  Val  Glu  Trp  Leu  Arg  Lys  Lys  Leu  Gln  Asp  Val  His
               20                  25                       30

Asn  Tyr  Xaa
          35
```

( 2 ) INFORMATION FOR SEQ ID NO:47:

( i ) SEQUENCE CHARACTERISTICS:
        ( A ) LENGTH: 35 amino acids
        ( B ) TYPE: amino acid
        ( D ) TOPOLOGY: unknown ( i i ) MOLECULE TYPE: protein ( i x ) FEATURE:
        ( A ) NAME/KEY: Modified-site
        ( B ) LOCATION: 35
        ( D ) OTHER INFORMATION: /note= "Where "Xaa"is selected
            from the group consisting of Hol, Ho, a homoserine
            amide, or the sequence of amino acids comprising residues 35-84 of PTH."

(xi) SEQUENCE DESCRIPTION: SEQ ID NO:47:

| Ser | Val | Ser | Glu | Ile | Gln | Leu | Leu | His | Asn | Leu | Lys | Lys | His | Leu | Asn |
|---|---|---|---|---|---|---|---|---|---|---|---|---|---|---|---|
| 1 | | | | 5 | | | | | 10 | | | | | 15 | |

| Ser | Leu | Glu | Arg | Val | Glu | Trp | Leu | Arg | Lys | Lys | Leu | Gln | Asp | Val | His |
|---|---|---|---|---|---|---|---|---|---|---|---|---|---|---|---|
| | | | 20 | | | | | 25 | | | | | 30 | | |

| Asn | Tyr | Xaa |
|---|---|---|
| | | 35 |

(2) INFORMATION FOR SEQ ID NO:48:

(i) SEQUENCE CHARACTERISTICS:
        (A) LENGTH: 35 amino acids
        (B) TYPE: amino acid
        (D) TOPOLOGY: unknown (ii) MOLECULE TYPE: protein (ix) FEATURE:
        (A) NAME/KEY: Modified-site
        (B) LOCATION: 35
        (D) OTHER INFORMATION: /note= "Where "Xaa" is selected
            from the group consisting of Hol, Ho, a homoserine
            amide, or the sequence of amino acids comprising
            residues 35-84 of PTH."

(xi) SEQUENCE DESCRIPTION: SEQ ID NO:48:

| Ser | Val | Ser | Glu | Ile | Gln | Leu | Leu | His | Asn | Leu | Glu | Lys | His | Leu | Asn |
|---|---|---|---|---|---|---|---|---|---|---|---|---|---|---|---|
| 1 | | | | 5 | | | | | 10 | | | | | 15 | |

| Ser | Leu | Glu | Arg | Val | Glu | Trp | Leu | Arg | Lys | Lys | Leu | Gln | Asp | Val | His |
|---|---|---|---|---|---|---|---|---|---|---|---|---|---|---|---|
| | | | 20 | | | | | 25 | | | | | 30 | | |

| Asn | Tyr | Xaa |
|---|---|---|
| | | 35 |

(2) INFORMATION FOR SEQ ID NO:49:

(i) SEQUENCE CHARACTERISTICS:
        (A) LENGTH: 35 amino acids
        (B) TYPE: amino acid
        (D) TOPOLOGY: unknown (ii) MOLECULE TYPE: protein (ix) FEATURE:
        (A) NAME/KEY: Modified-site
        (B) LOCATION: 35
        (D) OTHER INFORMATION: /note= "Where "Xaa" is selected
            from the group consisting of Hol, Ho, a homoserine
            amide, or the sequence of amino acids comprising
            residues 35-84 of PTH."

(xi) SEQUENCE DESCRIPTION: SEQ ID NO:49:

| Ser | Val | Ser | Glu | Ile | Gln | Leu | Leu | His | Asn | Leu | Gly | Lys | His | Leu | Asn |
|---|---|---|---|---|---|---|---|---|---|---|---|---|---|---|---|
| 1 | | | | 5 | | | | | 10 | | | | | 15 | |

| Ser | Leu | Glu | Arg | Val | Glu | Trp | Leu | Arg | Lys | Lys | Leu | Gln | Asp | Val | His |
|---|---|---|---|---|---|---|---|---|---|---|---|---|---|---|---|
| | | | 20 | | | | | 25 | | | | | 30 | | |

| Asn | Tyr | Xaa |
|---|---|---|
| | | 35 |

(2) INFORMATION FOR SEQ ID NO:50:

(i) SEQUENCE CHARACTERISTICS:
        (A) LENGTH: 35 amino acids
        (B) TYPE: amino acid
        (D) TOPOLOGY: unknown (ii) MOLECULE TYPE: protein ( i x ) FEATURE:
    ( A ) NAME/KEY: Modified-site
    ( B ) LOCATION: 35
    ( D ) OTHER INFORMATION: /note= "Where "Xaa"is selected
        from the group consisting of Hol, Ho, a homoserine
        amide, or the sequence of amino acids comprising
        residues 35- 84 of PTH."

( x i ) SEQUENCE DESCRIPTION: SEQ ID NO:50:

```
Ser Val Ser Glu Ile Gln Leu Leu His Asn Leu Gly Arg His Leu Asn
 1               5                  10                  15
Ser Leu Glu Arg Val Glu Trp Leu Arg Lys Lys Leu Gln Asp Val His
            20                  25                  30
Asn Tyr Xaa
        35
```

( 2 ) INFORMATION FOR SEQ ID NO:51:

( i ) SEQUENCE CHARACTERISTICS:
        ( A ) LENGTH: 35 amino acids
        ( B ) TYPE: amino acid
        ( D ) TOPOLOGY: unknown ( i i ) MOLECULE TYPE: protein ( i x ) FEATURE:
        ( A ) NAME/KEY: Modified-site
        ( B ) LOCATION: 35
        ( D ) OTHER INFORMATION: /note= "Where "Xaa"is selected
            from the group consisting of Hol, Ho, a homoserine
            amide, or the sequence of amino acids comprising
            residues 35- 84 of PTH."

( x i ) SEQUENCE DESCRIPTION: SEQ ID NO:51:

```
Ser Val Ser Glu Ile Gln Leu Leu His Asn Leu Gly Glu His Leu Asn
 1               5                  10                  15
Ser Leu Glu Arg Val Glu Trp Leu Arg Lys Lys Leu Gln Asp Val His
            20                  25                  30
Asn Tyr Xaa
        35
```

( 2 ) INFORMATION FOR SEQ ID NO:52:

( i ) SEQUENCE CHARACTERISTICS:
        ( A ) LENGTH: 35 amino acids
        ( B ) TYPE: amino acid
        ( D ) TOPOLOGY: unknown ( i i ) MOLECULE TYPE: protein ( i x ) FEATURE:
        ( A ) NAME/KEY: Modified-site
        ( B ) LOCATION: 35
        ( D ) OTHER INFORMATION: /note= "Where "Xaa"is selected
            from the group consisting of Hol, Ho, a homoserine
            amide, or the sequence of amino acids comprising
            residues 35- 84 of PTH."

( x i ) SEQUENCE DESCRIPTION: SEQ ID NO:52:

```
Ser Val Ser Glu Ile Gln Leu Leu His Asn Leu Gly Gly His Leu Asn
 1               5                  10                  15
Ser Leu Glu Arg Val Glu Trp Leu Arg Lys Lys Leu Gln Asp Val His
            20                  25                  30
Asn Tyr Xaa
        35
```

( 2 ) INFORMATION FOR SEQ ID NO:53:

( i ) SEQUENCE CHARACTERISTICS:
  ( A ) LENGTH: 35 amino acids
  ( B ) TYPE: amino acid
  ( D ) TOPOLOGY: unknown ( i i ) MOLECULE TYPE: protein ( i x ) FEATURE:
  ( A ) NAME/KEY: Modified-site
  ( B ) LOCATION: 35
  ( D ) OTHER INFORMATION: /note= "Where "Xaa"is selected
    from the group consisting of Hol, Ho, a homoserine
    amide, or the sequence of amino acids comprising
    residues 35- 84 of PTH."

( x i ) SEQUENCE DESCRIPTION: SEQ ID NO:53:

```
Ser  Val  Ser  Glu  Ile  Gln  Leu  Leu  His  Asn  Leu  Gly  Lys  Lys  Leu  Asn
1                  5                        10                       15
Ser  Leu  Glu  Arg  Val  Glu  Trp  Leu  Arg  Lys  Lys  Leu  Gln  Asp  Val  His
                20                       25                  30
Asn  Tyr  Xaa
         35
```

( 2 ) INFORMATION FOR SEQ ID NO:54:

( i ) SEQUENCE CHARACTERISTICS:
    ( A ) LENGTH: 35 amino acids
    ( B ) TYPE: amino acid
    ( D ) TOPOLOGY: unknown ( i i ) MOLECULE TYPE: protein ( i x ) FEATURE:
    ( A ) NAME/KEY: Modified-site
    ( B ) LOCATION: 35
    ( D ) OTHER INFORMATION: /note= "Where "Xaa"is selected
      from the group consisting of Hol, Ho, a homoserine
      amide, or the sequence of amino acids comprising
      residues 35- 84 of PTH."

( x i ) SEQUENCE DESCRIPTION: SEQ ID NO:54:

```
Ser  Val  Ser  Glu  Ile  Gln  Leu  Leu  His  Asn  Leu  Gly  Lys  Arg  Leu  Asn
1                  5                        10                       15
Ser  Leu  Glu  Arg  Val  Glu  Trp  Leu  Arg  Lys  Lys  Leu  Gln  Asp  Val  His
                20                       25                  30
Asn  Tyr  Xaa
         35
```

( 2 ) INFORMATION FOR SEQ ID NO:55:

( i ) SEQUENCE CHARACTERISTICS:
    ( A ) LENGTH: 35 amino acids
    ( B ) TYPE: amino acid
    ( D ) TOPOLOGY: unknown ( i i ) MOLECULE TYPE: protein ( i x ) FEATURE:
    ( A ) NAME/KEY: Modified-site
    ( B ) LOCATION: 35
    ( D ) OTHER INFORMATION: /note= "Where "Xaa"is selected
      from the group consisting of Hol, Ho, a homoserine
      amide, or the sequence of amino acids comprising
      residues 35- 84 of PTH."

( x i ) SEQUENCE DESCRIPTION: SEQ ID NO:55:

```
Ser  Val  Ser  Glu  Ile  Gln  Leu  Leu  His  Asn  Leu  Gly  Lys  Glu  Leu  Asn
1                  5                        10                       15
Ser  Leu  Glu  Arg  Val  Glu  Trp  Leu  Arg  Lys  Lys  Leu  Gln  Asp  Val  His
```

Asn Tyr Xaa
         35

( 2 ) INFORMATION FOR SEQ ID NO:56:

( i ) SEQUENCE CHARACTERISTICS:
        ( A ) LENGTH: 35 amino acids
        ( B ) TYPE: amino acid
        ( D ) TOPOLOGY: unknown ( i i ) MOLECULE TYPE: protein ( i x ) FEATURE:
        ( A ) NAME/KEY: Modified-site
        ( B ) LOCATION: 35
        ( D ) OTHER INFORMATION: /note= "Where "Xaa"is selected
            from the group consisting of Hol, Ho, a homoserine
            amide, or the sequence of amino acids comprising
            residues 35- 84 of PTH."

( x i ) SEQUENCE DESCRIPTION: SEQ ID NO:56:

Ser  Val  Ser  Glu  Ile  Gln  Leu  Leu  His  Asn  Leu  Gly  Lys  Gly  Leu  Asn
1                   5                        10                       15

Ser  Leu  Glu  Arg  Val  Glu  Trp  Leu  Arg  Lys  Lys  Leu  Gln  Asp  Val  His
              20                       25                       30

Asn  Tyr  Xaa
          35

( 2 ) INFORMATION FOR SEQ ID NO:57:

( i ) SEQUENCE CHARACTERISTICS:
        ( A ) LENGTH: 35 amino acids
        ( B ) TYPE: amino acid
        ( D ) TOPOLOGY: unknown ( i i ) MOLECULE TYPE: protein ( i x ) FEATURE:
        ( A ) NAME/KEY: Modified-site
        ( B ) LOCATION: 35
        ( D ) OTHER INFORMATION: /note= "Where "Xaa"is selected
            from the group consisting of Hol, Ho, a homoserine
            amide, or the sequence of amino acids comprising
            residues 35- 84 of PTH."

( x i ) SEQUENCE DESCRIPTION: SEQ ID NO:57:

Ser  Val  Ser  Glu  Ile  Gln  Leu  Leu  His  Asn  Leu  Gly  Lys  His  Lys  Asn
1                   5                        10                       15

Ser  Leu  Glu  Arg  Val  Glu  Trp  Leu  Arg  Lys  Lys  Leu  Gln  Asp  Val  His
              20                       25                       30

Asn  Tyr  Xaa
          35

( 2 ) INFORMATION FOR SEQ ID NO:58:

( i ) SEQUENCE CHARACTERISTICS:
        ( A ) LENGTH: 35 amino acids
        ( B ) TYPE: amino acid
        ( D ) TOPOLOGY: unknown ( i i ) MOLECULE TYPE: protein ( i x ) FEATURE:
        ( A ) NAME/KEY: Modified-site
        ( B ) LOCATION: 35
        ( D ) OTHER INFORMATION: /note= "Where "Xaa"is selected
            from the group consisting of Hol, Ho, a homoserine
            amide, or the sequence of amino acids comprising
            residues 35- 84 of PTH."

( x i ) SEQUENCE DESCRIPTION: SEQ ID NO:58:

| Ser | Val | Ser | Glu | Ile | Gln | Leu | Leu | His | Asn | Leu | Gly | Lys | His | Arg | Asn |
|---|---|---|---|---|---|---|---|---|---|---|---|---|---|---|---|
| 1 | | | | 5 | | | | | 10 | | | | | 15 | |
| Ser | Leu | Glu | Arg | Val | Glu | Trp | Leu | Arg | Lys | Lys | Leu | Gln | Asp | Val | His |
| | | | 20 | | | | | 25 | | | | | 30 | | |
| Asn | Tyr | Xaa | | | | | | | | | | | | | |
| | | 35 | | | | | | | | | | | | | |

( 2 ) INFORMATION FOR SEQ ID NO:59:

( i ) SEQUENCE CHARACTERISTICS:
        ( A ) LENGTH: 35 amino acids
        ( B ) TYPE: amino acid
        ( D ) TOPOLOGY: unknown ( i i ) MOLECULE TYPE: protein ( i x ) FEATURE:
        ( A ) NAME/KEY: Modified-site
        ( B ) LOCATION: 35
        ( D ) OTHER INFORMATION: /note= "Where "Xaa"is selected
        from the group consisting of Hol, Ho, a homoserine
        amide, or the sequence of amino acids comprising
        residues 35- 84 of PTH."

( x i ) SEQUENCE DESCRIPTION: SEQ ID NO:59:

| Ser | Val | Ser | Glu | Ile | Gln | Leu | Leu | His | Asn | Leu | Gly | Lys | His | Glu | Asn |
|---|---|---|---|---|---|---|---|---|---|---|---|---|---|---|---|
| 1 | | | | 5 | | | | | 10 | | | | | 15 | |
| Ser | Leu | Glu | Arg | Val | Glu | Trp | Leu | Arg | Lys | Lys | Leu | Gln | Asp | Val | His |
| | | | 20 | | | | | 25 | | | | | 30 | | |
| Asn | Tyr | Xaa | | | | | | | | | | | | | |
| | | 35 | | | | | | | | | | | | | |

( 2 ) INFORMATION FOR SEQ ID NO:60:

( i ) SEQUENCE CHARACTERISTICS:
        ( A ) LENGTH: 35 amino acids
        ( B ) TYPE: amino acid
        ( D ) TOPOLOGY: unknown ( i i ) MOLECULE TYPE: protein ( i x ) FEATURE:
        ( A ) NAME/KEY: Modified-site
        ( B ) LOCATION: 35
        ( D ) OTHER INFORMATION: /note= "Where "Xaa"is selected
        from the group consisting of Hol, Ho, a homoserine
        amide, or the sequence of amino acids comprising
        residues 35- 84 of PTH."

( x i ) SEQUENCE DESCRIPTION: SEQ ID NO:60:

| Ser | Val | Ser | Glu | Ile | Gln | Leu | Leu | His | Asn | Leu | Gly | Lys | His | Gly | Asn |
|---|---|---|---|---|---|---|---|---|---|---|---|---|---|---|---|
| 1 | | | | 5 | | | | | 10 | | | | | 15 | |
| Ser | Leu | Glu | Arg | Val | Glu | Trp | Leu | Arg | Lys | Lys | Leu | Gln | Asp | Val | His |
| | | | 20 | | | | | 25 | | | | | 30 | | |
| Asn | Tyr | Xaa | | | | | | | | | | | | | |
| | | 35 | | | | | | | | | | | | | |

( 2 ) INFORMATION FOR SEQ ID NO:61:

( i ) SEQUENCE CHARACTERISTICS:
        ( A ) LENGTH: 35 amino acids
        ( B ) TYPE: amino acid
        ( D ) TOPOLOGY: unknown ( i i ) MOLECULE TYPE: protein ( i x ) FEATURE:
- ( A ) NAME/KEY: Modified-site
- ( B ) LOCATION: 35
- ( D ) OTHER INFORMATION: /note= "Where "Xaa"is selected from the group consisting of Hol, Ho, a homoserine amide, or the sequence of amino acids comprising residues 35- 84 of PTH."

( x i ) SEQUENCE DESCRIPTION: SEQ ID NO:61:

| Ser | Val | Ser | Glu | Ile | Gln | Leu | Leu | His | Asn | Leu | Gly | Lys | His | Leu | Lys |
|---|---|---|---|---|---|---|---|---|---|---|---|---|---|---|---|
| 1 | | | | 5 | | | | | 10 | | | | | | 15 |
| Ser | Leu | Glu | Arg | Val | Glu | Trp | Leu | Arg | Lys | Lys | Leu | Gln | Asp | Val | His |
| | | | 20 | | | | | 25 | | | | | 30 | | |
| Asn | Tyr | Xaa | | | | | | | | | | | | | |
| | | 35 | | | | | | | | | | | | | |

( 2 ) INFORMATION FOR SEQ ID NO:62:

( i ) SEQUENCE CHARACTERISTICS:
- ( A ) LENGTH: 35 amino acids
- ( B ) TYPE: amino acid
- ( D ) TOPOLOGY: unknown ( i i ) MOLECULE TYPE: protein ( i x ) FEATURE:
- ( A ) NAME/KEY: Modified-site
- ( B ) LOCATION: 35
- ( D ) OTHER INFORMATION: /note= "Where "Xaa"is selected from the group consisting of Hol, Ho, a homoserine amide, or the sequence of amino acids comprising residues 35- 84 of PTH."

( x i ) SEQUENCE DESCRIPTION: SEQ ID NO:62:

| Ser | Val | Ser | Glu | Ile | Gln | Leu | Leu | His | Asn | Leu | Gly | Lys | His | Leu | Glu |
|---|---|---|---|---|---|---|---|---|---|---|---|---|---|---|---|
| 1 | | | | 5 | | | | | 10 | | | | | | 15 |
| Ser | Leu | Glu | Arg | Val | Glu | Trp | Leu | Arg | Lys | Lys | Leu | Gln | Asp | Val | His |
| | | | 20 | | | | | 25 | | | | | 30 | | |
| Asn | Tyr | Xaa | | | | | | | | | | | | | |
| | | 35 | | | | | | | | | | | | | |

( 2 ) INFORMATION FOR SEQ ID NO:63:

( i ) SEQUENCE CHARACTERISTICS:
- ( A ) LENGTH: 35 amino acids
- ( B ) TYPE: amino acid
- ( D ) TOPOLOGY: unknown ( i i ) MOLECULE TYPE: protein ( i x ) FEATURE:
- ( A ) NAME/KEY: Modified-site
- ( B ) LOCATION: 35
- ( D ) OTHER INFORMATION: /note= "Where "Xaa"is selected from the group consisting of Hol, Ho, a homoserine amide, or the sequence of amino acids comprising residues 35- 84 of PTH."

( x i ) SEQUENCE DESCRIPTION: SEQ ID NO:63:

| Ser | Val | Ser | Glu | Ile | Gln | Leu | Leu | His | Asn | Leu | Gly | Lys | His | Leu | Gly |
|---|---|---|---|---|---|---|---|---|---|---|---|---|---|---|---|
| 1 | | | | 5 | | | | | 10 | | | | | | 15 |
| Ser | Leu | Glu | Arg | Val | Glu | Trp | Leu | Arg | Lys | Lys | Leu | Gln | Asp | Val | His |
| | | | 20 | | | | | 25 | | | | | 30 | | |
| Asn | Tyr | Xaa | | | | | | | | | | | | | |
| | | 35 | | | | | | | | | | | | | |

( 2 ) INFORMATION FOR SEQ ID NO:64:

( i ) SEQUENCE CHARACTERISTICS:
  ( A ) LENGTH: 35 amino acids
  ( B ) TYPE: amino acid
  ( D ) TOPOLOGY: unknown ( i i ) MOLECULE TYPE: protein ( i x ) FEATURE:
  ( A ) NAME/KEY: Modified-site
  ( B ) LOCATION: 35
  ( D ) OTHER INFORMATION: /note= "Where "Xaa"is selected from the group consisting of Hol, Ho, a homoserine amide, or the sequence of amino acids comprising residues 35- 84 of PTH."

( x i ) SEQUENCE DESCRIPTION: SEQ ID NO:64:

| Ser | Val | Ser | Glu | Ile | Gln | Leu | Leu | His | Asn | Leu | Gly | Lys | His | Leu | Asn |
|---|---|---|---|---|---|---|---|---|---|---|---|---|---|---|---|
| 1 | | | | 5 | | | | | 10 | | | | | 15 | |
| Arg | Leu | Glu | Arg | Val | Glu | Trp | Leu | Arg | Lys | Lys | Leu | Gln | Asp | Val | His |
| | | | 20 | | | | | 25 | | | | | 30 | | |
| Asn | Tyr | Xaa | | | | | | | | | | | | | |
| | | 35 | | | | | | | | | | | | | |

( 2 ) INFORMATION FOR SEQ ID NO:65:

( i ) SEQUENCE CHARACTERISTICS:
  ( A ) LENGTH: 35 amino acids
  ( B ) TYPE: amino acid
  ( D ) TOPOLOGY: unknown ( i i ) MOLECULE TYPE: protein ( i x ) FEATURE:
  ( A ) NAME/KEY: Modified-site
  ( B ) LOCATION: 35
  ( D ) OTHER INFORMATION: /note= "Where "Xaa"is selected from the group consisting of Hol, Ho, a homoserine amide, or the sequence of amino acids comprising residues 35- 84 of PTH."

( x i ) SEQUENCE DESCRIPTION: SEQ ID NO:65:

| Ser | Val | Ser | Glu | Ile | Gln | Leu | Leu | His | Asn | Leu | Gly | Lys | His | Leu | Asn |
|---|---|---|---|---|---|---|---|---|---|---|---|---|---|---|---|
| 1 | | | | 5 | | | | | 10 | | | | | 15 | |
| Glu | Leu | Glu | Arg | Val | Glu | Trp | Leu | Arg | Lys | Lys | Leu | Gln | Asp | Val | His |
| | | | 20 | | | | | 25 | | | | | 30 | | |
| Asn | Tyr | Xaa | | | | | | | | | | | | | |
| | | 35 | | | | | | | | | | | | | |

( 2 ) INFORMATION FOR SEQ ID NO:66:

( i ) SEQUENCE CHARACTERISTICS:
  ( A ) LENGTH: 35 amino acids
  ( B ) TYPE: amino acid
  ( D ) TOPOLOGY: unknown ( i i ) MOLECULE TYPE: protein ( i x ) FEATURE:
  ( A ) NAME/KEY: Modified-site
  ( B ) LOCATION: 35
  ( D ) OTHER INFORMATION: /note= "Where "Xaa"is selected from the group consisting of Hol, Ho, a homoserine amide, or the sequence of amino acids comprising residues 35- 84 of PTH."

( x i ) SEQUENCE DESCRIPTION: SEQ ID NO:66:

| Ser | Val | Ser | Glu | Ile | Gln | Leu | Leu | His | Asn | Leu | Gly | Lys | His | Leu | Asn |
|---|---|---|---|---|---|---|---|---|---|---|---|---|---|---|---|
| 1 | | | | 5 | | | | | 10 | | | | | 15 | |
| Gly | Leu | Glu | Arg | Val | Glu | Trp | Leu | Arg | Lys | Lys | Leu | Gln | Asp | Val | His |
| | | | 20 | | | | | 25 | | | | | 30 | | |

Asn Tyr Xaa
35

( 2 ) INFORMATION FOR SEQ ID NO:67:

( i ) SEQUENCE CHARACTERISTICS:
        ( A ) LENGTH: 35 amino acids
        ( B ) TYPE: amino acid
        ( D ) TOPOLOGY: unknown ( i i ) MOLECULE TYPE: protein ( i x ) FEATURE:
        ( A ) NAME/KEY: Modified-site
        ( B ) LOCATION: 35
        ( D ) OTHER INFORMATION: /note= "Where "Xaa"is selected
            from the group consisting of Hol, Ho, a homoserine
            amide, or the sequence of amino acids comprising
            residues 35- 84 of PTH."

( x i ) SEQUENCE DESCRIPTION: SEQ ID NO:67:

Ser Val Ser Glu Ile Gln Leu Leu His Asn Leu Gly Lys His Leu Asn
1               5                   10                  15

Ser Arg Glu Arg Val Glu Trp Leu Arg Lys Lys Leu Gln Asp Val His
            20                  25                  30

Asn Tyr Xaa
35

( 2 ) INFORMATION FOR SEQ ID NO:68:

( i ) SEQUENCE CHARACTERISTICS:
        ( A ) LENGTH: 35 amino acids
        ( B ) TYPE: amino acid
        ( D ) TOPOLOGY: unknown ( i i ) MOLECULE TYPE: protein ( i x ) FEATURE:
        ( A ) NAME/KEY: Modified-site
        ( B ) LOCATION: 35
        ( D ) OTHER INFORMATION: /note= "Where "Xaa"is selected
            from the group consisting of Hol, Ho, a homoserine
            amide, or the sequence of amino acids comprising
            residues 35- 84 of PTH."

( x i ) SEQUENCE DESCRIPTION: SEQ ID NO:68:

Ser Val Ser Glu Ile Gln Leu Leu His Asn Leu Gly Lys His Leu Asn
1               5                   10                  15

Ser Glu Glu Arg Val Glu Trp Leu Arg Lys Lys Leu Gln Asp Val His
            20                  25                  30

Asn Tyr Xaa
35

( 2 ) INFORMATION FOR SEQ ID NO:69:

( i ) SEQUENCE CHARACTERISTICS:
        ( A ) LENGTH: 35 amino acids
        ( B ) TYPE: amino acid
        ( D ) TOPOLOGY: unknown ( i i ) MOLECULE TYPE: protein ( i x ) FEATURE:
        ( A ) NAME/KEY: Modified-site
        ( B ) LOCATION: 35
        ( D ) OTHER INFORMATION: /note= "Where "Xaa"is selected
            from the group consisting of Hol, Ho, a homoserine
            amide, or the sequence of amino acids comprising
            residues 35- 84 of PTH."

(x i) SEQUENCE DESCRIPTION: SEQ ID NO:69:

| Ser | Val | Ser | Glu | Ile | Gln | Leu | Leu | His | Asn | Leu | Gly | Lys | His | Leu | Asn |
|---|---|---|---|---|---|---|---|---|---|---|---|---|---|---|---|
| 1 | | | | 5 | | | | | 10 | | | | | 15 | |

| Ser | Leu | Arg | Arg | Val | Glu | Trp | Leu | Arg | Lys | Lys | Leu | Gln | Asp | Val | His |
|---|---|---|---|---|---|---|---|---|---|---|---|---|---|---|---|
| | | | 20 | | | | | 25 | | | | | 30 | | |

| Asn | Tyr | Xaa |
|---|---|---|
| | | 35 |

(2) INFORMATION FOR SEQ ID NO:70:

(i) SEQUENCE CHARACTERISTICS:
        (A) LENGTH: 35 amino acids
        (B) TYPE: amino acid
        (D) TOPOLOGY: unknown (i i) MOLECULE TYPE: protein (i x) FEATURE:
        (A) NAME/KEY: Modified-site
        (B) LOCATION: 35
        (D) OTHER INFORMATION: /note= "Where "Xaa"is selected
            from the group consisting of Hol, Ho, a homoserine
            amide, or the sequence of amino acids comprising
            residues 35- 84 of PTH."

(x i) SEQUENCE DESCRIPTION: SEQ ID NO:70:

| Ser | Val | Ser | Glu | Ile | Gln | Leu | Leu | His | Asn | Leu | Gly | Lys | His | Leu | Asn |
|---|---|---|---|---|---|---|---|---|---|---|---|---|---|---|---|
| 1 | | | | 5 | | | | | 10 | | | | | 15 | |

| Ser | Leu | Glu | Arg | Val | Glu | Trp | Leu | Arg | Lys | Lys | Leu | Gln | Asp | Val | His |
|---|---|---|---|---|---|---|---|---|---|---|---|---|---|---|---|
| | | | 20 | | | | | 25 | | | | | 30 | | |

| Asn | Tyr | Xaa |
|---|---|---|
| | | 35 |

(2) INFORMATION FOR SEQ ID NO:71:

(i) SEQUENCE CHARACTERISTICS:
        (A) LENGTH: 35 amino acids
        (B) TYPE: amino acid
        (D) TOPOLOGY: unknown (i i) MOLECULE TYPE: protein (i x) FEATURE:
        (A) NAME/KEY: Modified-site
        (B) LOCATION: 35
        (D) OTHER INFORMATION: /note= "Where "Xaa"is selected
            from the group consisting of Hol, Ho, a homoserine
            amide, or the sequence of amino acids comprising
            residues 35- 84 of PTH."

(x i) SEQUENCE DESCRIPTION: SEQ ID NO:71:

| Ser | Val | Ser | Glu | Ile | Gln | Leu | Leu | His | Asn | Leu | Gly | Lys | His | Leu | Asn |
|---|---|---|---|---|---|---|---|---|---|---|---|---|---|---|---|
| 1 | | | | 5 | | | | | 10 | | | | | 15 | |

| Ser | Leu | Gly | Arg | Val | Glu | Trp | Leu | Arg | Lys | Lys | Leu | Gln | Asp | Val | His |
|---|---|---|---|---|---|---|---|---|---|---|---|---|---|---|---|
| | | | 20 | | | | | 25 | | | | | 30 | | |

| Asn | Tyr | Xaa |
|---|---|---|
| | | 35 |

(2) INFORMATION FOR SEQ ID NO:72:

(i) SEQUENCE CHARACTERISTICS:
        (A) LENGTH: 35 amino acids
        (B) TYPE: amino acid
        (D) TOPOLOGY: unknown (i i) MOLECULE TYPE: protein (i x) FEATURE:

( A ) NAME/KEY: Modified-site
( B ) LOCATION: 35
( D ) OTHER INFORMATION: /note= "Where "Xaa"is selected from the group consisting of Hol, Ho, a homoserine amide, or the sequence of amino acids comprising residues 35- 84 of PTH."

( x i ) SEQUENCE DESCRIPTION: SEQ ID NO:72:

| Ser | Val | Ser | Glu | Ile | Gln | Leu | Leu | His | Asn | Leu | Gly | Lys | His | Leu | Asn |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Ser | Leu | Glu | Lys | Val | Glu | Trp | Leu | Arg | Lys | Lys | Leu | Gln | Asp | Val | His |
|     |     |     | 20  |     |     |     |     | 25  |     |     |     |     | 30  |     |     |
| Asn | Tyr | Xaa |     |     |     |     |     |     |     |     |     |     |     |     |     |
|     |     | 35  |     |     |     |     |     |     |     |     |     |     |     |     |     |

( 2 ) INFORMATION FOR SEQ ID NO:73:

( i ) SEQUENCE CHARACTERISTICS:
( A ) LENGTH: 35 amino acids
( B ) TYPE: amino acid
( D ) TOPOLOGY: unknown ( i i ) MOLECULE TYPE: protein ( i x ) FEATURE:
( A ) NAME/KEY: Modified-site
( B ) LOCATION: 35
( D ) OTHER INFORMATION: /note= "Where "Xaa"is selected from the group consisting of Hol, Ho, a homoserine amide, or the sequence of amino acids comprising residues 35- 84 of PTH."

( x i ) SEQUENCE DESCRIPTION: SEQ ID NO:73:

| Ser | Val | Ser | Glu | Ile | Gln | Leu | Leu | His | Asn | Leu | Gly | Lys | His | Leu | Asn |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Ser | Leu | Glu | Arg | Val | Glu | Trp | Leu | Arg | Lys | Lys | Leu | Gln | Asp | Val | His |
|     |     |     | 20  |     |     |     |     | 25  |     |     |     |     | 30  |     |     |
| Asn | Tyr | Xaa |     |     |     |     |     |     |     |     |     |     |     |     |     |
|     |     | 35  |     |     |     |     |     |     |     |     |     |     |     |     |     |

( 2 ) INFORMATION FOR SEQ ID NO:74:

( i ) SEQUENCE CHARACTERISTICS:
( A ) LENGTH: 35 amino acids
( B ) TYPE: amino acid
( D ) TOPOLOGY: unknown ( i i ) MOLECULE TYPE: protein ( i x ) FEATURE:
( A ) NAME/KEY: Modified-site
( B ) LOCATION: 35
( D ) OTHER INFORMATION: /note= "Where "Xaa"is selected from the group consisting of Hol, Ho, a homoserine amide, or the sequence of amino acids comprising residues 35- 84 of PTH."

( x i ) SEQUENCE DESCRIPTION: SEQ ID NO:74:

| Ser | Val | Ser | Glu | Ile | Gln | Leu | Leu | His | Asn | Leu | Gly | Lys | His | Leu | Asn |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Ser | Leu | Glu | Glu | Val | Glu | Trp | Leu | Arg | Lys | Lys | Leu | Gln | Asp | Val | His |
|     |     |     | 20  |     |     |     |     | 25  |     |     |     |     | 30  |     |     |
| Asn | Tyr | Xaa |     |     |     |     |     |     |     |     |     |     |     |     |     |
|     |     | 35  |     |     |     |     |     |     |     |     |     |     |     |     |     |

( 2 ) INFORMATION FOR SEQ ID NO:75:

( i ) SEQUENCE CHARACTERISTICS:

(A) LENGTH: 35 amino acids
(B) TYPE: amino acid
(D) TOPOLOGY: unknown (i i) MOLECULE TYPE: protein (i x) FEATURE:
(A) NAME/KEY: Modified-site
(B) LOCATION: 35
(D) OTHER INFORMATION: /note= "Where "Xaa"is selected from the group consisting of Hol, Ho, a homoserine amide, or the sequence of amino acids comprising residues 35- 84 of PTH."

(x i) SEQUENCE DESCRIPTION: SEQ ID NO:75:

| Ser | Val | Ser | Glu | Ile | Gln | Leu | Leu | His | Asn | Leu | Gly | Lys | His | Leu | Asn |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ser | Leu | Glu | Gly | Val | Glu | Trp | Leu | Arg | Lys | Lys | Leu | Gln | Asp | Val | His |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Asn | Tyr | Xaa |
|-----|-----|-----|
|     |     | 35  |

(2) INFORMATION FOR SEQ ID NO:76:

(i) SEQUENCE CHARACTERISTICS:
(A) LENGTH: 35 amino acids
(B) TYPE: amino acid
(D) TOPOLOGY: unknown (i i) MOLECULE TYPE: protein (i x) FEATURE:
(A) NAME/KEY: Modified-site
(B) LOCATION: 35
(D) OTHER INFORMATION: /note= "Where "Xaa"is selected from the group consisting of Hol, Ho, a homoserine amide, or the sequence of amino acids comprising residues 35- 84 of PTH."

(x i) SEQUENCE DESCRIPTION: SEQ ID NO:76:

| Ser | Val | Ser | Glu | Ile | Gln | Leu | Leu | His | Asn | Leu | Gly | Lys | His | Leu | Asn |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ser | Leu | Glu | Arg | Arg | Glu | Trp | Leu | Arg | Lys | Lys | Leu | Gln | Asp | Val | His |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Asn | Tyr | Xaa |
|-----|-----|-----|
|     |     | 35  |

(2) INFORMATION FOR SEQ ID NO:77:

(i) SEQUENCE CHARACTERISTICS:
(A) LENGTH: 35 amino acids
(B) TYPE: amino acid
(D) TOPOLOGY: unknown (i i) MOLECULE TYPE: protein (i x) FEATURE:
(A) NAME/KEY: Modified-site
(B) LOCATION: 35
(D) OTHER INFORMATION: /note= "Where "Xaa"is selected from the group consisting of Hol, Ho, a homoserine amide, or the sequence of amino acids comprising residues 35- 84 of PTH."

(x i) SEQUENCE DESCRIPTION: SEQ ID NO:77:

| Ser | Val | Ser | Glu | Ile | Gln | Leu | Leu | His | Asn | Leu | Gly | Lys | His | Leu | Asn |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ser | Leu | Glu | Arg | Glu | Glu | Trp | Leu | Arg | Lys | Lys | Leu | Gln | Asp | Val | His |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

Asn Tyr Xaa
         35

(2) INFORMATION FOR SEQ ID NO:78:

(i) SEQUENCE CHARACTERISTICS:
        (A) LENGTH: 35 amino acids
        (B) TYPE: amino acid
        (D) TOPOLOGY: unknown (ii) MOLECULE TYPE: protein (ix) FEATURE:
        (A) NAME/KEY: Modified-site
        (B) LOCATION: 35
        (D) OTHER INFORMATION: /note= "Where "Xaa"is selected
            from the group consisting of Hol, Ho, a homoserine
            amide, or the sequence of amino acids comprising
            residues 35- 84 of PTH."

(xi) SEQUENCE DESCRIPTION: SEQ ID NO:78:

Ser Val Ser Glu Ile Gln Leu Leu His Asn Leu Gly Lys His Leu Asn
 1               5                  10                  15

Ser Leu Glu Arg Gly Glu Trp Leu Arg Lys Lys Leu Gln Asp Val His
            20                  25                  30

Asn Tyr Xaa
         35

(2) INFORMATION FOR SEQ ID NO:79:

(i) SEQUENCE CHARACTERISTICS:
        (A) LENGTH: 35 amino acids
        (B) TYPE: amino acid
        (D) TOPOLOGY: unknown (ii) MOLECULE TYPE: protein (ix) FEATURE:
        (A) NAME/KEY: Modified-site
        (B) LOCATION: 35
        (D) OTHER INFORMATION: /note= "Where "Xaa"is selected
            from the group consisting of Hol, Ho, a homoserine
            amide, or the sequence of amino acids comprising
            residues 35- 84 of PTH."

(xi) SEQUENCE DESCRIPTION: SEQ ID NO:79:

Ser Val Ser Glu Ile Gln Leu Leu His Asn Leu Gly Lys His Leu Asn
 1               5                  10                  15

Ser Leu Glu Arg Val Arg Trp Leu Arg Lys Lys Leu Gln Asp Val His
            20                  25                  30

Asn Tyr Xaa
         35

(2) INFORMATION FOR SEQ ID NO:80:

(i) SEQUENCE CHARACTERISTICS:
        (A) LENGTH: 35 amino acids
        (B) TYPE: amino acid
        (D) TOPOLOGY: unknown (ii) MOLECULE TYPE: protein (ix) FEATURE:
        (A) NAME/KEY: Modified-site
        (B) LOCATION: 35
        (D) OTHER INFORMATION: /note= "Where "Xaa"is selected
            from the group consisting of Hol, Ho, a homoserine
            amide, or the sequence of amino acids comprising
            residues 35- 84 of PTH."

(xi) SEQUENCE DESCRIPTION: SEQ ID NO:80:

```
       Ser   Val   Ser   Glu   Ile   Gln   Leu   Leu   His   Asn   Leu   Gly   Lys   His   Leu   Asn
       1                       5                       10                                  15

Ser   Leu   Glu   Arg   Val   Glu   Trp   Leu   Arg   Lys   Lys   Leu   Gln   Asp   Val   His
                         20                  25                                30

Asn   Tyr   Xaa
                   35
```

( 2 ) INFORMATION FOR SEQ ID NO:81:

( i ) SEQUENCE CHARACTERISTICS:
        ( A ) LENGTH: 35 amino acids
        ( B ) TYPE: amino acid
        ( D ) TOPOLOGY: unknown ( i i ) MOLECULE TYPE: protein ( i x ) FEATURE:
        ( A ) NAME/KEY: Modified-site
        ( B ) LOCATION: 35
        ( D ) OTHER INFORMATION: /note= "Where "Xaa"is selected
            from the group consisting of Hol, Ho, a homoserine
            amide, or the sequence of amino acids comprising
            residues 35- 84 of PTH."

( x i ) SEQUENCE DESCRIPTION: SEQ ID NO:81:

```
       Ser   Val   Ser   Glu   Ile   Gln   Leu   Leu   His   Asn   Leu   Gly   Lys   His   Leu   Asn
       1                       5                       10                                  15

Ser   Leu   Glu   Arg   Val   Gly   Trp   Leu   Arg   Lys   Lys   Leu   Gln   Asp   Val   His
                         20                  25                                30

Asn   Tyr   Xaa
                   35
```

( 2 ) INFORMATION FOR SEQ ID NO:82:

( i ) SEQUENCE CHARACTERISTICS:
        ( A ) LENGTH: 35 amino acids
        ( B ) TYPE: amino acid
        ( D ) TOPOLOGY: unknown ( i i ) MOLECULE TYPE: protein ( i x ) FEATURE:
        ( A ) NAME/KEY: Modified-site
        ( B ) LOCATION: 35
        ( D ) OTHER INFORMATION: /note= "Where "Xaa"is selected
            from the group consisting of Hol, Ho, a homoserine
            amide, or the sequence of amino acids comprising
            residues 35- 84 of PTH."

( x i ) SEQUENCE DESCRIPTION: SEQ ID NO:82:

```
       Ser   Val   Ser   Glu   Ile   Gln   Leu   Leu   His   Asn   Leu   Gly   Lys   His   Leu   Asn
       1                       5                       10                                  15

Ser   Leu   Glu   Arg   Val   Glu   Lys   Leu   Arg   Lys   Lys   Leu   Gln   Asp   Val   His
                         20                  25                                30

Asn   Tyr   Xaa
                   35
```

( 2 ) INFORMATION FOR SEQ ID NO:83:

( i ) SEQUENCE CHARACTERISTICS:
        ( A ) LENGTH: 35 amino acids
        ( B ) TYPE: amino acid
        ( D ) TOPOLOGY: unknown ( i i ) MOLECULE TYPE: protein ( i x ) FEATURE:
        ( A ) NAME/KEY: Modified-site (B) LOCATION: 35
(D) OTHER INFORMATION: /note= "Where "Xaa"is selected from the group consisting of Hol, Ho, a homoserine amide, or the sequence of amino acids comprising residues 35- 84 of PTH."

(x i) SEQUENCE DESCRIPTION: SEQ ID NO:83:

Ser Val Ser Glu Ile Gln Leu Leu His Asn Leu Gly Lys His Leu Asn
1               5                   10                  15

Ser Leu Glu Arg Val Glu Glu Leu Arg Lys Lys Leu Gln Asp Val His
            20                  25                  30

Asn Tyr Xaa
        35

(2) INFORMATION FOR SEQ ID NO:84:

(i) SEQUENCE CHARACTERISTICS:
(A) LENGTH: 35 amino acids
(B) TYPE: amino acid
(D) TOPOLOGY: unknown (i i) MOLECULE TYPE: protein (i x) FEATURE:
(A) NAME/KEY: Modified-site
(B) LOCATION: 35
(D) OTHER INFORMATION: /note= "Where "Xaa"is selected from the group consisting of Hol, Ho, a homoserine amide, or the sequence of amino acids comprising residues 35- 84 of PTH."

(x i) SEQUENCE DESCRIPTION: SEQ ID NO:84:

Ser Val Ser Glu Ile Gln Leu Leu His Asn Leu Gly Lys His Leu Asn
1               5                   10                  15

Ser Leu Glu Arg Val Glu Gly Leu Arg Lys Lys Leu Gln Asp Val His
            20                  25                  30

Asn Tyr Xaa
        35

(2) INFORMATION FOR SEQ ID NO:85:

(i) SEQUENCE CHARACTERISTICS:
(A) LENGTH: 35 amino acids
(B) TYPE: amino acid
(D) TOPOLOGY: unknown (i i) MOLECULE TYPE: protein (i x) FEATURE:
(A) NAME/KEY: Modified-site
(B) LOCATION: 35
(D) OTHER INFORMATION: /note= "Where "Xaa"is selected from the group consisting of Hol, Ho, a homoserine amide, or the sequence of amino acids comprising residues 35- 84 of PTH."

(x i) SEQUENCE DESCRIPTION: SEQ ID NO:85:

Ser Val Ser Glu Ile Gln Leu Leu His Asn Leu Gly Lys His Leu Asn
1               5                   10                  15

Ser Leu Glu Arg Val Glu Trp Arg Arg Lys Lys Leu Gln Asp Val His
            20                  25                  30

Asn Tyr Xaa
        35

(2) INFORMATION FOR SEQ ID NO:86:

(i) SEQUENCE CHARACTERISTICS:
(A) LENGTH: 35 amino acids (B) TYPE: amino acid
(D) TOPOLOGY: unknown (ii) MOLECULE TYPE: protein (ix) FEATURE:
(A) NAME/KEY: Modified-site
(B) LOCATION: 35
(D) OTHER INFORMATION: /note= "Where "Xaa"is selected from the group consisting of Hol, Ho, a homoserine amide, or the sequence of amino acids comprising residues 35- 84 of PTH."

(xi) SEQUENCE DESCRIPTION: SEQ ID NO:86:

| Ser | Val | Ser | Glu | Ile | Gln | Leu | Leu | His | Asn | Leu | Gly | Lys | His | Leu | Asn |
|---|---|---|---|---|---|---|---|---|---|---|---|---|---|---|---|
| 1 | | | | 5 | | | | | 10 | | | | | 15 | |

| Ser | Leu | Glu | Arg | Val | Glu | Trp | Glu | Arg | Lys | Lys | Leu | Gln | Asp | Val | His |
|---|---|---|---|---|---|---|---|---|---|---|---|---|---|---|---|
| | | | 20 | | | | | 25 | | | | | 30 | | |

| Asn | Tyr | Xaa |
|---|---|---|
| | | 35 |

(2) INFORMATION FOR SEQ ID NO:87:

(i) SEQUENCE CHARACTERISTICS:
(A) LENGTH: 35 amino acids
(B) TYPE: amino acid
(D) TOPOLOGY: unknown (ii) MOLECULE TYPE: protein (ix) FEATURE:
(A) NAME/KEY: Modified-site
(B) LOCATION: 35
(D) OTHER INFORMATION: /note= "Where "Xaa"is selected from the group consisting of Hol, Ho, a homoserine amide, or the sequence of amino acids comprising residues 35- 84 of PTH."

(xi) SEQUENCE DESCRIPTION: SEQ ID NO:87:

| Ser | Val | Ser | Glu | Ile | Gln | Leu | Leu | His | Asn | Leu | Gly | Lys | His | Leu | Asn |
|---|---|---|---|---|---|---|---|---|---|---|---|---|---|---|---|
| 1 | | | | 5 | | | | | 10 | | | | | 15 | |

| Ser | Leu | Glu | Arg | Val | Glu | Trp | Gly | Arg | Lys | Lys | Leu | Gln | Asp | Val | His |
|---|---|---|---|---|---|---|---|---|---|---|---|---|---|---|---|
| | | | 20 | | | | | 25 | | | | | 30 | | |

| Asn | Tyr | Xaa |
|---|---|---|
| | | 35 |

(2) INFORMATION FOR SEQ ID NO:88:

(i) SEQUENCE CHARACTERISTICS:
(A) LENGTH: 35 amino acids
(B) TYPE: amino acid
(D) TOPOLOGY: unknown (ii) MOLECULE TYPE: protein (ix) FEATURE:
(A) NAME/KEY: Modified-site
(B) LOCATION: 35
(D) OTHER INFORMATION: /note= "Where "Xaa"is selected from the group consisting of Hol, Ho, a homoserine amide, or the sequence of amino acids comprising residues 35- 84 of PTH."

(xi) SEQUENCE DESCRIPTION: SEQ ID NO:88:

| Ser | Val | Ser | Glu | Ile | Gln | Leu | Leu | His | Asn | Leu | Gly | Lys | His | Leu | Asn |
|---|---|---|---|---|---|---|---|---|---|---|---|---|---|---|---|
| 1 | | | | 5 | | | | | 10 | | | | | 15 | |

| Ser | Leu | Glu | Arg | Val | Glu | Trp | Leu | Lys | Lys | Lys | Leu | Gln | Asp | Val | His |
|---|---|---|---|---|---|---|---|---|---|---|---|---|---|---|---|
| | | | 20 | | | | | 25 | | | | | 30 | | |

| Asn | Tyr | Xaa |
|---|---|---|

35

(2) INFORMATION FOR SEQ ID NO:89:

(i) SEQUENCE CHARACTERISTICS:
    (A) LENGTH: 35 amino acids
    (B) TYPE: amino acid
    (D) TOPOLOGY: unknown (ii) MOLECULE TYPE: protein (ix) FEATURE:
    (A) NAME/KEY: Modified-site
    (B) LOCATION: 35
    (D) OTHER INFORMATION: /note= "Where "Xaa"is selected
      from the group consisting of Hol, Ho, a homoserine
      amide, or the sequence of amino acids comprising
      residues 35- 84 of PTH."

(xi) SEQUENCE DESCRIPTION: SEQ ID NO:89:

Ser Val Ser Glu Ile Gln Leu Leu His Asn Leu Gly Lys His Leu Asn
1               5                   10                  15
Ser Leu Glu Arg Val Glu Trp Leu Glu Lys Lys Leu Gln Asp Val His
            20                  25                  30
Asn Tyr Xaa
        35

(2) INFORMATION FOR SEQ ID NO:90:

(i) SEQUENCE CHARACTERISTICS:
    (A) LENGTH: 35 amino acids
    (B) TYPE: amino acid
    (D) TOPOLOGY: unknown (ii) MOLECULE TYPE: protein (ix) FEATURE:
    (A) NAME/KEY: Modified-site
    (B) LOCATION: 35
    (D) OTHER INFORMATION: /note= "Where "Xaa"is selected
      from the group consisting of Hol, Ho, a homoserine
      amide, or the sequence of amino acids comprising
      residues 35- 84 of PTH."

(xi) SEQUENCE DESCRIPTION: SEQ ID NO:90:

Ser Val Ser Glu Ile Gln Leu Leu His Asn Leu Gly Lys His Leu Asn
1               5                   10                  15
Ser Leu Glu Arg Val Glu Trp Leu Arg Lys Lys Leu Gln Asp Val His
            20                  25                  30
Asn Tyr Xaa
        35

(2) INFORMATION FOR SEQ ID NO:91:

(i) SEQUENCE CHARACTERISTICS:
    (A) LENGTH: 35 amino acids
    (B) TYPE: amino acid
    (D) TOPOLOGY: unknown (ii) MOLECULE TYPE: protein (ix) FEATURE:
    (A) NAME/KEY: Modified-site
    (B) LOCATION: 35
    (D) OTHER INFORMATION: /note= "Where "Xaa"is selected
      from the group consisting of Hol, Ho, a homoserine
      amide, or the sequence of amino acids comprising
      residues 35- 84 of PTH."

(xi) SEQUENCE DESCRIPTION: SEQ ID NO:91:

Ser Val Ser Glu Ile Gln Leu Leu His Asn Leu Gly Lys His Leu Asn
1               5                   10                  15

Ser Leu Glu Arg Val Glu Trp Leu Arg Arg Lys Leu Gln Asp Val His
            20                  25                  30

Asn Tyr Xaa
        35

( 2 ) INFORMATION FOR SEQ ID NO:92:

( i ) SEQUENCE CHARACTERISTICS:
        ( A ) LENGTH: 35 amino acids
        ( B ) TYPE: amino acid
        ( D ) TOPOLOGY: unknown ( i i ) MOLECULE TYPE: protein ( i x ) FEATURE:
        ( A ) NAME/KEY: Modified-site
        ( B ) LOCATION: 35
        ( D ) OTHER INFORMATION: /note= "Where "Xaa"is selected
        from the group consisting of Hol, Ho, a homoserine
        amide, or the sequence of amino acids comprising
        residues 35- 84 of PTH."

( x i ) SEQUENCE DESCRIPTION: SEQ ID NO:92:

Ser Val Ser Glu Ile Gln Leu Leu His Asn Leu Gly Lys His Leu Asn
1               5                   10                  15

Ser Leu Glu Arg Val Glu Trp Leu Arg Glu Lys Leu Gln Asp Val His
            20                  25                  30

Asn Tyr Xaa
        35

( 2 ) INFORMATION FOR SEQ ID NO:93:

( i ) SEQUENCE CHARACTERISTICS:
        ( A ) LENGTH: 35 amino acids
        ( B ) TYPE: amino acid
        ( D ) TOPOLOGY: unknown ( i i ) MOLECULE TYPE: protein ( i x ) FEATURE:
        ( A ) NAME/KEY: Modified-site
        ( B ) LOCATION: 35
        ( D ) OTHER INFORMATION: /note= "Where "Xaa"is selected
        from the group consisting of Hol, Ho, a homoserine
        amide, or the sequence of amino acids comprising
        residues 35- 84 of PTH."

( x i ) SEQUENCE DESCRIPTION: SEQ ID NO:93:

Ser Val Ser Glu Ile Gln Leu Leu His Asn Leu Gly Lys His Leu Asn
1               5                   10                  15

Ser Leu Glu Arg Val Glu Trp Leu Arg Gly Lys Leu Gln Asp Val His
            20                  25                  30

Asn Tyr Xaa
        35

( 2 ) INFORMATION FOR SEQ ID NO:94:

( i ) SEQUENCE CHARACTERISTICS:
        ( A ) LENGTH: 35 amino acids
        ( B ) TYPE: amino acid
        ( D ) TOPOLOGY: unknown ( i i ) MOLECULE TYPE: protein ( i x ) FEATURE:
        ( A ) NAME/KEY: Modified-site
        ( B ) LOCATION: 35

(D) OTHER INFORMATION: /note= "Where "Xaa"is selected
from the group consisting of Hol, Ho, a homoserine
amide, or the sequence of amino acids comprising
residues 35- 84 of PTH."

(x i) SEQUENCE DESCRIPTION: SEQ ID NO:94:

| Ser | Val | Ser | Glu | Ile | Gln | Leu | Leu | His | Asn | Leu | Gly | Lys | His | Leu | Asn |
|---|---|---|---|---|---|---|---|---|---|---|---|---|---|---|---|
| 1 | | | | 5 | | | | | 10 | | | | | 15 | |
| Ser | Leu | Glu | Arg | Val | Glu | Trp | Leu | Arg | Lys | Lys | Leu | Gln | Asp | Val | His |
| | | | 20 | | | | | 25 | | | | | 30 | | |
| Asn | Tyr | Xaa | | | | | | | | | | | | | |
| | | 35 | | | | | | | | | | | | | |

(2) INFORMATION FOR SEQ ID NO:95:

(i) SEQUENCE CHARACTERISTICS:
(A) LENGTH: 35 amino acids
(B) TYPE: amino acid
(D) TOPOLOGY: unknown (i i) MOLECULE TYPE: protein (i x) FEATURE:
(A) NAME/KEY: Modified-site
(B) LOCATION: 35
(D) OTHER INFORMATION: /note= "Where "Xaa"is selected
from the group consisting of Hol, Ho, a homoserine
amide, or the sequence of amino acids comprising
residues 35- 84 of PTH."

(x i) SEQUENCE DESCRIPTION: SEQ ID NO:95:

| Ser | Val | Ser | Glu | Ile | Gln | Leu | Leu | His | Asn | Leu | Gly | Lys | His | Leu | Asn |
|---|---|---|---|---|---|---|---|---|---|---|---|---|---|---|---|
| 1 | | | | 5 | | | | | 10 | | | | | 15 | |
| Ser | Leu | Glu | Arg | Val | Glu | Trp | Leu | Arg | Lys | Arg | Leu | Gln | Asp | Val | His |
| | | | 20 | | | | | 25 | | | | | 30 | | |
| Asn | Tyr | Xaa | | | | | | | | | | | | | |
| | | 35 | | | | | | | | | | | | | |

(2) INFORMATION FOR SEQ ID NO:96:

(i) SEQUENCE CHARACTERISTICS:
(A) LENGTH: 35 amino acids
(B) TYPE: amino acid
(D) TOPOLOGY: unknown (i i) MOLECULE TYPE: protein (i x) FEATURE:
(A) NAME/KEY: Modified-site
(B) LOCATION: 35
(D) OTHER INFORMATION: /note= "Where "Xaa"is selected
from the group consisting of Hol, Ho, a homoserine
amide, or the sequence of amino acids comprising
residues 35- 84 of PTH."

(x i) SEQUENCE DESCRIPTION: SEQ ID NO:96:

| Ser | Val | Ser | Glu | Ile | Gln | Leu | Leu | His | Asn | Leu | Gly | Lys | His | Leu | Asn |
|---|---|---|---|---|---|---|---|---|---|---|---|---|---|---|---|
| 1 | | | | 5 | | | | | 10 | | | | | 15 | |
| Ser | Leu | Glu | Arg | Val | Glu | Trp | Leu | Arg | Lys | Glu | Leu | Gln | Asp | Val | His |
| | | | 20 | | | | | 25 | | | | | 30 | | |
| Asn | Tyr | Xaa | | | | | | | | | | | | | |
| | | 35 | | | | | | | | | | | | | |

(2) INFORMATION FOR SEQ ID NO:97:

(i) SEQUENCE CHARACTERISTICS:
(A) LENGTH: 35 amino acids
(B) TYPE: amino acid (D) TOPOLOGY: unknown (i i) MOLECULE TYPE: protein (i x) FEATURE:
    (A) NAME/KEY: Modified-site
    (B) LOCATION: 35
    (D) OTHER INFORMATION: /note= "Where "Xaa"is selected from the group consisting of Hol, Ho, a homoserine amide, or the sequence of amino acids comprising residues 35- 84 of PTH."

(x i) SEQUENCE DESCRIPTION: SEQ ID NO:97:

| Ser | Val | Ser | Glu | Ile | Gln | Leu | Leu | His | Asn | Leu | Gly | Lys | His | Leu | Asn |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ser | Leu | Glu | Arg | Val | Glu | Trp | Leu | Arg | Lys | Gly | Leu | Gln | Asp | Val | His |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Asn | Tyr | Xaa |
|-----|-----|-----|
|     |     | 35  |

(2) INFORMATION FOR SEQ ID NO:98:

(i) SEQUENCE CHARACTERISTICS:
        (A) LENGTH: 35 amino acids
        (B) TYPE: amino acid
        (D) TOPOLOGY: unknown (i i) MOLECULE TYPE: protein (i x) FEATURE:
    (A) NAME/KEY: Modified-site
    (B) LOCATION: 35
    (D) OTHER INFORMATION: /note= "Where "Xaa"is selected from the group consisting of Hol, Ho, a homoserine amide, or the sequence of amino acids comprising residues 35- 84 of PTH."

(x i) SEQUENCE DESCRIPTION: SEQ ID NO:98:

| Ser | Val | Ser | Glu | Ile | Gln | Leu | Leu | His | Asn | Leu | Gly | Lys | His | Leu | Asn |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ser | Leu | Glu | Arg | Val | Glu | Trp | Leu | Arg | Lys | Lys | Lys | Gln | Asp | Val | His |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Asn | Tyr | Xaa |
|-----|-----|-----|
|     |     | 35  |

(2) INFORMATION FOR SEQ ID NO:99:

(i) SEQUENCE CHARACTERISTICS:
        (A) LENGTH: 35 amino acids
        (B) TYPE: amino acid
        (D) TOPOLOGY: unknown (i i) MOLECULE TYPE: protein (i x) FEATURE:
    (A) NAME/KEY: Modified-site
    (B) LOCATION: 35
    (D) OTHER INFORMATION: /note= "Where "Xaa"is selected from the group consisting of Hol, Ho, a homoserine amide, or the sequence of amino acids comprising residues 35- 84 of PTH."

(x i) SEQUENCE DESCRIPTION: SEQ ID NO:99:

| Ser | Val | Ser | Glu | Ile | Gln | Leu | Leu | His | Asn | Leu | Gly | Lys | His | Leu | Asn |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ser | Leu | Glu | Arg | Val | Glu | Trp | Leu | Arg | Lys | Lys | Arg | Gln | Asp | Val | His |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Asn | Tyr | Xaa |
|-----|-----|-----|
|     |     | 35  |

( 2 ) INFORMATION FOR SEQ ID NO:100:

(i) SEQUENCE CHARACTERISTICS:
(A) LENGTH: 35 amino acids
(B) TYPE: amino acid
(D) TOPOLOGY: unknown (ii) MOLECULE TYPE: protein (ix) FEATURE:
(A) NAME/KEY: Modified-site
(B) LOCATION: 35
(D) OTHER INFORMATION: /note= "Where "Xaa"is selected from the group consisting of Hol, Ho, a homoserine amide, or the sequence of amino acids comprising residues 35- 84 of PTH."

(xi) SEQUENCE DESCRIPTION: SEQ ID NO:100:

```
Ser  Val  Ser  Glu  Ile  Gln  Leu  Leu  His  Asn  Leu  Gly  Lys  His  Leu  Asn
1                   5                        10                       15
Ser  Leu  Glu  Arg  Val  Glu  Trp  Leu  Arg  Lys  Lys  Glu  Gln  Asp  Val  His
               20                       25                       30
Asn  Tyr  Xaa
          35
```

( 2 ) INFORMATION FOR SEQ ID NO:101:

(i) SEQUENCE CHARACTERISTICS:
(A) LENGTH: 35 amino acids
(B) TYPE: amino acid
(D) TOPOLOGY: unknown (ii) MOLECULE TYPE: protein (ix) FEATURE:
(A) NAME/KEY: Modified-site
(B) LOCATION: 35
(D) OTHER INFORMATION: /note= "Where "Xaa"is selected from the group consisting of Hol, Ho, a homoserine amide, or the sequence of amino acids comprising residues 35- 84 of PTH."

(xi) SEQUENCE DESCRIPTION: SEQ ID NO:101:

```
Ser  Val  Ser  Glu  Ile  Gln  Leu  Leu  His  Asn  Leu  Gly  Lys  His  Leu  Asn
1                   5                        10                       15
Ser  Leu  Glu  Arg  Val  Glu  Trp  Leu  Arg  Lys  Lys  Leu  Lys  Asp  Val  His
               20                       25                       30
Asn  Tyr  Xaa
          35
```

( 2 ) INFORMATION FOR SEQ ID NO:102:

(i) SEQUENCE CHARACTERISTICS:
(A) LENGTH: 35 amino acids
(B) TYPE: amino acid
(D) TOPOLOGY: unknown (ii) MOLECULE TYPE: protein (ix) FEATURE:
(A) NAME/KEY: Modified-site
(B) LOCATION: 35
(D) OTHER INFORMATION: /note= "Where "Xaa"is selected from the group consisting of Hol, Ho, a homoserine amide, or the sequence of amino acids comprising residues 35- 84 of PTH."

(xi) SEQUENCE DESCRIPTION: SEQ ID NO:102:

```
Ser  Val  Ser  Glu  Ile  Gln  Leu  Leu  His  Asn  Leu  Gly  Lys  His  Leu  Asn
```

```
                1               5                    10                   15
        Ser  Leu  Glu  Arg  Val  Glu  Trp  Leu  Arg  Lys  Lys  Leu  Glu  Asp  Val  His
                          20                   25                   30

Asn  Tyr  Xaa
                  35
```

(2) INFORMATION FOR SEQ ID NO:103:

(i) SEQUENCE CHARACTERISTICS:
    (A) LENGTH: 35 amino acids
    (B) TYPE: amino acid
    (D) TOPOLOGY: unknown (ii) MOLECULE TYPE: protein (ix) FEATURE:
    (A) NAME/KEY: Modified-site
    (B) LOCATION: 35
    (D) OTHER INFORMATION: /note= "Where "Xaa"is selected
        from the group consisting of Hol, Ho, a homoserine
        amide, or the sequence of amino acids comprising
        residues 35- 84 of PTH."

(xi) SEQUENCE DESCRIPTION: SEQ ID NO:103:

```
        Ser  Val  Ser  Glu  Ile  Gln  Leu  Leu  His  Asn  Leu  Gly  Lys  His  Leu  Asn
        1                      5                    10                   15

Ser  Leu  Glu  Arg  Val  Glu  Trp  Leu  Arg  Lys  Lys  Leu  Gly  Asp  Val  His
                          20                   25                   30

Asn  Tyr  Xaa
                  35
```

(2) INFORMATION FOR SEQ ID NO:104:

(i) SEQUENCE CHARACTERISTICS:
    (A) LENGTH: 35 amino acids
    (B) TYPE: amino acid
    (D) TOPOLOGY: unknown (ii) MOLECULE TYPE: protein (ix) FEATURE:
    (A) NAME/KEY: Modified-site
    (B) LOCATION: 35
    (D) OTHER INFORMATION: /note= "Where "Xaa"is selected
        from the group consisting of Hol, Ho, a homoserine
        amide, or the sequence of amino acids comprising
        residues 35- 84 of PTH."

(xi) SEQUENCE DESCRIPTION: SEQ ID NO:104:

```
        Ser  Val  Ser  Glu  Ile  Gln  Leu  Leu  His  Asn  Leu  Gly  Lys  His  Leu  Asn
        1                      5                    10                   15

Ser  Leu  Glu  Arg  Val  Glu  Trp  Leu  Arg  Lys  Lys  Leu  Gln  Arg  Val  His
                          20                   25                   30

Asn  Tyr  Xaa
                  35
```

(2) INFORMATION FOR SEQ ID NO:105:

(i) SEQUENCE CHARACTERISTICS:
    (A) LENGTH: 35 amino acids
    (B) TYPE: amino acid
    (D) TOPOLOGY: unknown (ii) MOLECULE TYPE: protein (ix) FEATURE:
    (A) NAME/KEY: Modified-site
    (B) LOCATION: 35
    (D) OTHER INFORMATION: /note= "Where "Xaa"is selected from the group consisting of Hol, Ho, a homoserine
amide, or the sequence of amino acids comprising
residues 35-84 of PTH."

( x i ) SEQUENCE DESCRIPTION: SEQ ID NO:105:

| Ser | Val | Ser | Glu | Ile | Gln | Leu | Leu | His | Asn | Leu | Gly | Lys | His | Leu | Asn |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Ser | Leu | Glu | Arg | Val | Glu | Trp | Leu | Arg | Lys | Lys | Leu | Gln | Glu | Val | His |
|     |     |     | 20  |     |     |     |     | 25  |     |     |     |     | 30  |     |     |
| Asn | Tyr | Xaa |     |     |     |     |     |     |     |     |     |     |     |     |     |
|     |     | 35  |     |     |     |     |     |     |     |     |     |     |     |     |     |

( 2 ) INFORMATION FOR SEQ ID NO:106:

( i ) SEQUENCE CHARACTERISTICS:
        ( A ) LENGTH: 35 amino acids
        ( B ) TYPE: amino acid
        ( D ) TOPOLOGY: unknown ( i i ) MOLECULE TYPE: protein ( i x ) FEATURE:
        ( A ) NAME/KEY: Modified-site
        ( B ) LOCATION: 35
        ( D ) OTHER INFORMATION: /note= "Where "Xaa" is selected
from the group consisting of Hol, Ho, a homoserine
amide, or the sequence of amino acids comprising
residues 35-84 of PTH."

( x i ) SEQUENCE DESCRIPTION: SEQ ID NO:106:

| Ser | Val | Ser | Glu | Ile | Gln | Leu | Leu | His | Asn | Leu | Gly | Lys | His | Leu | Asn |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Ser | Leu | Glu | Arg | Val | Glu | Trp | Leu | Arg | Lys | Lys | Leu | Gln | Gly | Val | His |
|     |     |     | 20  |     |     |     |     | 25  |     |     |     |     | 30  |     |     |
| Asn | Tyr | Xaa |     |     |     |     |     |     |     |     |     |     |     |     |     |
|     |     | 35  |     |     |     |     |     |     |     |     |     |     |     |     |     |

( 2 ) INFORMATION FOR SEQ ID NO:107:

( i ) SEQUENCE CHARACTERISTICS:
        ( A ) LENGTH: 35 amino acids
        ( B ) TYPE: amino acid
        ( D ) TOPOLOGY: unknown ( i i ) MOLECULE TYPE: protein ( i x ) FEATURE:
        ( A ) NAME/KEY: Modified-site
        ( B ) LOCATION: 35
        ( D ) OTHER INFORMATION: /note= "Where "Xaa" is selected
from the group consisting of Hol, Ho, a homoserine
amide, or the sequence of amino acids comprising
residues 35-84 of PTH."

( x i ) SEQUENCE DESCRIPTION: SEQ ID NO:107:

| Ser | Val | Ser | Glu | Ile | Gln | Leu | Leu | His | Asn | Leu | Gly | Lys | His | Leu | Asn |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Ser | Leu | Glu | Arg | Val | Glu | Trp | Leu | Arg | Lys | Lys | Leu | Gln | Asp | Lys | His |
|     |     |     | 20  |     |     |     |     | 25  |     |     |     |     | 30  |     |     |
| Asn | Tyr | Xaa |     |     |     |     |     |     |     |     |     |     |     |     |     |
|     |     | 35  |     |     |     |     |     |     |     |     |     |     |     |     |     |

( 2 ) INFORMATION FOR SEQ ID NO:108:

( i ) SEQUENCE CHARACTERISTICS:
        ( A ) LENGTH: 35 amino acids
        ( B ) TYPE: amino acid
        ( D ) TOPOLOGY: unknown ( i i ) MOLECULE TYPE: protein ( i x ) FEATURE:
    ( A ) NAME/KEY: Modified-site
    ( B ) LOCATION: 35
    ( D ) OTHER INFORMATION: /note= "Where "Xaa"is selected
        from the group consisting of Hol, Ho, a homoserine
        amide, or the sequence of amino acids comprising
        residues 35- 84 of PTH."

( x i ) SEQUENCE DESCRIPTION: SEQ ID NO:108:

```
Ser  Val  Ser  Glu  Ile  Gln  Leu  Leu  His  Asn  Leu  Gly  Lys  His  Leu  Asn
1                   5                        10                       15
Ser  Leu  Glu  Arg  Val  Glu  Trp  Leu  Arg  Lys  Lys  Leu  Gln  Asp  Arg  His
               20                       25                       30
Asn  Tyr  Xaa
          35
```

( 2 ) INFORMATION FOR SEQ ID NO:109:

( i ) SEQUENCE CHARACTERISTICS:
        ( A ) LENGTH: 35 amino acids
        ( B ) TYPE: amino acid
        ( D ) TOPOLOGY: unknown ( i i ) MOLECULE TYPE: protein ( i x ) FEATURE:
    ( A ) NAME/KEY: Modified-site
    ( B ) LOCATION: 35
    ( D ) OTHER INFORMATION: /note= "Where "Xaa"is selected
        from the group consisting of Hol, Ho, a homoserine
        amide, or the sequence of amino acids comprising
        residues 35- 84 of PTH."

( x i ) SEQUENCE DESCRIPTION: SEQ ID NO:109:

```
Ser  Val  Ser  Glu  Ile  Gln  Leu  Leu  His  Asn  Leu  Gly  Lys  His  Leu  Asn
1                   5                        10                       15
Ser  Leu  Glu  Arg  Val  Glu  Trp  Leu  Arg  Lys  Lys  Leu  Gln  Asp  Glu  His
               20                       25                       30
Asn  Tyr  Xaa
          35
```

( 2 ) INFORMATION FOR SEQ ID NO:110:

( i ) SEQUENCE CHARACTERISTICS:
        ( A ) LENGTH: 35 amino acids
        ( B ) TYPE: amino acid
        ( D ) TOPOLOGY: unknown ( i i ) MOLECULE TYPE: protein ( i x ) FEATURE:
    ( A ) NAME/KEY: Modified-site
    ( B ) LOCATION: 35
    ( D ) OTHER INFORMATION: /note= "Where "Xaa"is selected
        from the group consisting of Hol, Ho, a homoserine
        amide, or the sequence of amino acids comprising
        residues 35- 84 of PTH."

( x i ) SEQUENCE DESCRIPTION: SEQ ID NO:110:

```
Ser  Val  Ser  Glu  Ile  Gln  Leu  Leu  His  Asn  Leu  Gly  Lys  His  Leu  Asn
1                   5                        10                       15
Ser  Leu  Glu  Arg  Val  Glu  Trp  Leu  Arg  Lys  Lys  Leu  Gln  Asp  Gly  His
               20                       25                       30
Asn  Tyr  Xaa
          35
```

( 2 ) INFORMATION FOR SEQ ID NO:111:

( i ) SEQUENCE CHARACTERISTICS:
( A ) LENGTH: 35 amino acids
( B ) TYPE: amino acid
( D ) TOPOLOGY: unknown ( i i ) MOLECULE TYPE: protein ( i x ) FEATURE:
( A ) NAME/KEY: Modified-site
( B ) LOCATION: 35
( D ) OTHER INFORMATION: /note= "Where "Xaa"is selected from the group consisting of Hol, Ho, a homoserine amide, or the sequence of amino acids comprising residues 35- 84 of PTH."

( x i ) SEQUENCE DESCRIPTION: SEQ ID NO:111:

| Ser | Val | Ser | Glu | Ile | Gln | Leu | Leu | His | Asn | Leu | Gly | Lys | His | Leu | Asn |
|---|---|---|---|---|---|---|---|---|---|---|---|---|---|---|---|
| 1 | | | | 5 | | | | | 10 | | | | | 15 | |
| Ser | Leu | Glu | Arg | Val | Glu | Trp | Leu | Arg | Lys | Lys | Leu | Gln | Asp | Val | Lys |
| | | | 20 | | | | | 25 | | | | | 30 | | |
| Asn | Tyr | Xaa | | | | | | | | | | | | | |
| | | 35 | | | | | | | | | | | | | |

( 2 ) INFORMATION FOR SEQ ID NO:112:

( i ) SEQUENCE CHARACTERISTICS:
( A ) LENGTH: 35 amino acids
( B ) TYPE: amino acid
( D ) TOPOLOGY: unknown ( i i ) MOLECULE TYPE: protein ( i x ) FEATURE:
( A ) NAME/KEY: Modified-site
( B ) LOCATION: 35
( D ) OTHER INFORMATION: /note= "Where "Xaa"is selected from the group consisting of Hol, Ho, a homoserine amide, or the sequence of amino acids comprising residues 35- 84 of PTH."

( x i ) SEQUENCE DESCRIPTION: SEQ ID NO:112:

| Ser | Val | Ser | Glu | Ile | Gln | Leu | Leu | His | Asn | Leu | Gly | Lys | His | Leu | Asn |
|---|---|---|---|---|---|---|---|---|---|---|---|---|---|---|---|
| 1 | | | | 5 | | | | | 10 | | | | | 15 | |
| Ser | Leu | Glu | Arg | Val | Glu | Trp | Leu | Arg | Lys | Lys | Leu | Gln | Asp | Val | Arg |
| | | | 20 | | | | | 25 | | | | | 30 | | |
| Asn | Tyr | Xaa | | | | | | | | | | | | | |
| | | 35 | | | | | | | | | | | | | |

( 2 ) INFORMATION FOR SEQ ID NO:113:

( i ) SEQUENCE CHARACTERISTICS:
( A ) LENGTH: 35 amino acids
( B ) TYPE: amino acid
( D ) TOPOLOGY: unknown ( i i ) MOLECULE TYPE: protein ( i x ) FEATURE:
( A ) NAME/KEY: Modified-site
( B ) LOCATION: 35
( D ) OTHER INFORMATION: /note= "Where "Xaa"is selected from the group consisting of Hol, Ho, a homoserine amide, or the sequence of amino acids comprising residues 35- 84 of PTH."

( x i ) SEQUENCE DESCRIPTION: SEQ ID NO:113:

| Ser | Val | Ser | Glu | Ile | Gln | Leu | Leu | His | Asn | Leu | Gly | Lys | His | Leu | Asn |
|---|---|---|---|---|---|---|---|---|---|---|---|---|---|---|---|
| 1 | | | | 5 | | | | | 10 | | | | | 15 | |

```
        Ser  Leu  Glu  Arg  Val  Glu  Trp  Leu  Arg  Lys  Lys  Leu  Gln  Asp  Val  Glu
                   20                         25                         30

Asn  Tyr  Xaa
                   35
```

( 2 ) INFORMATION FOR SEQ ID NO:114:

( i ) SEQUENCE CHARACTERISTICS:
  ( A ) LENGTH: 35 amino acids
  ( B ) TYPE: amino acid
  ( D ) TOPOLOGY: unknown ( i i ) MOLECULE TYPE: protein ( i x ) FEATURE:
  ( A ) NAME/KEY: Modified-site
  ( B ) LOCATION: 35
  ( D ) OTHER INFORMATION: /note= "Where "Xaa"is selected
   from the group consisting of Hol, Ho, a homoserine
   amide, or the sequence of amino acids comprising
   residues 35- 84 of PTH."

( x i ) SEQUENCE DESCRIPTION: SEQ ID NO:114:

```
        Ser  Val  Ser  Glu  Ile  Gln  Leu  Leu  His  Asn  Leu  Gly  Lys  His  Leu  Asn
        1                    5                         10                        15

Ser  Leu  Glu  Arg  Val  Glu  Trp  Leu  Arg  Lys  Lys  Leu  Gln  Asp  Val  Gly
                   20                         25                         30

Asn  Tyr  Xaa
                   35
```

( 2 ) INFORMATION FOR SEQ ID NO:115:

( i ) SEQUENCE CHARACTERISTICS:
  ( A ) LENGTH: 35 amino acids
  ( B ) TYPE: amino acid
  ( D ) TOPOLOGY: unknown ( i i ) MOLECULE TYPE: protein ( i x ) FEATURE:
  ( A ) NAME/KEY: Modified-site
  ( B ) LOCATION: 35
  ( D ) OTHER INFORMATION: /note= "Where "Xaa"is selected
   from the group consisting of Hol, Ho, a homoserine
   amide, or the sequence of amino acids comprising
   residues 35- 84 of PTH."

( x i ) SEQUENCE DESCRIPTION: SEQ ID NO:115:

```
        Ser  Val  Ser  Glu  Ile  Gln  Leu  Leu  His  Asn  Leu  Gly  Lys  His  Leu  Asn
        1                    5                         10                        15

Ser  Leu  Glu  Arg  Val  Glu  Trp  Leu  Arg  Lys  Lys  Leu  Gln  Asp  Val  His
                   20                         25                         30

Lys  Tyr  Xaa
                   35
```

( 2 ) INFORMATION FOR SEQ ID NO:116:

( i ) SEQUENCE CHARACTERISTICS:
  ( A ) LENGTH: 35 amino acids
  ( B ) TYPE: amino acid
  ( D ) TOPOLOGY: unknown ( i i ) MOLECULE TYPE: protein ( i x ) FEATURE:
  ( A ) NAME/KEY: Modified-site
  ( B ) LOCATION: 35
  ( D ) OTHER INFORMATION: /note= "Where "Xaa"is selected
   from the group consisting of Hol, Ho, a homoserine amide, or the sequence of amino acids comprising
residues 35- 84 of PTH."

( x i ) SEQUENCE DESCRIPTION: SEQ ID NO:116:

| Ser | Val | Ser | Glu | Ile | Gln | Leu | Leu | His | Asn | Leu | Gly | Lys | His | Leu | Asn |
|---|---|---|---|---|---|---|---|---|---|---|---|---|---|---|---|
| 1 | | | | 5 | | | | | 10 | | | | | 15 | |

| Ser | Leu | Glu | Arg | Val | Glu | Trp | Leu | Arg | Lys | Lys | Leu | Gln | Asp | Val | His |
|---|---|---|---|---|---|---|---|---|---|---|---|---|---|---|---|
| | | | 20 | | | | | 25 | | | | | 30 | | |

| Arg | Tyr | Xaa |
|---|---|---|
| | | 35 |

( 2 ) INFORMATION FOR SEQ ID NO:117:

( i ) SEQUENCE CHARACTERISTICS:
        ( A ) LENGTH: 35 amino acids
        ( B ) TYPE: amino acid
        ( D ) TOPOLOGY: unknown ( i i ) MOLECULE TYPE: protein ( i x ) FEATURE:
        ( A ) NAME/KEY: Modified-site
        ( B ) LOCATION: 35
        ( D ) OTHER INFORMATION: /note= "Where "Xaa"is selected
        from the group consisting of Hol, Ho, a homoserine
        amide, or the sequence of amino acids comprising
        residues 35- 84 of PTH."

( x i ) SEQUENCE DESCRIPTION: SEQ ID NO:117:

| Ser | Val | Ser | Glu | Ile | Gln | Leu | Leu | His | Asn | Leu | Gly | Lys | His | Leu | Asn |
|---|---|---|---|---|---|---|---|---|---|---|---|---|---|---|---|
| 1 | | | | 5 | | | | | 10 | | | | | 15 | |

| Ser | Leu | Glu | Arg | Val | Glu | Trp | Leu | Arg | Lys | Lys | Leu | Gln | Asp | Val | His |
|---|---|---|---|---|---|---|---|---|---|---|---|---|---|---|---|
| | | | 20 | | | | | 25 | | | | | 30 | | |

| Glu | Tyr | Xaa |
|---|---|---|
| | | 35 |

( 2 ) INFORMATION FOR SEQ ID NO:118:

( i ) SEQUENCE CHARACTERISTICS:
        ( A ) LENGTH: 35 amino acids
        ( B ) TYPE: amino acid
        ( D ) TOPOLOGY: unknown ( i i ) MOLECULE TYPE: protein ( i x ) FEATURE:
        ( A ) NAME/KEY: Modified-site
        ( B ) LOCATION: 35
        ( D ) OTHER INFORMATION: /note= "Where "Xaa"is selected
        from the group consisting of Hol, Ho, a homoserine
        amide, or the sequence of amino acids comprising
        residues 35- 84 of PTH."

( x i ) SEQUENCE DESCRIPTION: SEQ ID NO:118:

| Ser | Val | Ser | Glu | Ile | Gln | Leu | Leu | His | Asn | Leu | Gly | Lys | His | Leu | Asn |
|---|---|---|---|---|---|---|---|---|---|---|---|---|---|---|---|
| 1 | | | | 5 | | | | | 10 | | | | | 15 | |

| Ser | Leu | Glu | Arg | Val | Glu | Trp | Leu | Arg | Lys | Lys | Leu | Gln | Asp | Val | His |
|---|---|---|---|---|---|---|---|---|---|---|---|---|---|---|---|
| | | | 20 | | | | | 25 | | | | | 30 | | |

| Gly | Tyr | Xaa |
|---|---|---|
| | | 35 |

( 2 ) INFORMATION FOR SEQ ID NO:119:

( i ) SEQUENCE CHARACTERISTICS:
        ( A ) LENGTH: 50 amino acids
        ( B ) TYPE: amino acid
        ( D ) TOPOLOGY: unknown (  i  i  ) MOLECULE TYPE: protein (  i x  ) FEATURE:
    (  A  ) NAME/KEY: Protein
    (  B  ) LOCATION: 1..50
    (  D  ) OTHER INFORMATION: /note= "Amino acid residues 34-84
        of Human PTH."

(  x i  ) SEQUENCE DESCRIPTION: SEQ ID NO:119:

| Val | Ala | Leu | Gly | Ala | Pro | Leu | Ala | Pro | Arg | Asp | Ala | Gly | Ser | Gln | Arg |
|---|---|---|---|---|---|---|---|---|---|---|---|---|---|---|---|
| 1 | | | | 5 | | | | | 10 | | | | | 15 | |

| Pro | Arg | Lys | Lys | Glu | Asp | Asn | Val | Leu | Val | Glu | Ser | His | Glu | Lys | Ser |
|---|---|---|---|---|---|---|---|---|---|---|---|---|---|---|---|
| | | 20 | | | | | | 25 | | | | | 30 | | |

| Leu | Gly | Glu | Ala | Asp | Lys | Ala | Asp | Val | Asp | Val | Leu | Thr | Lys | Ala | Lys |
|---|---|---|---|---|---|---|---|---|---|---|---|---|---|---|---|
| | | 35 | | | | | 40 | | | | | 45 | | | |

| Ser | Gln |
|---|---|
| | 50 |

( 2 ) INFORMATION FOR SEQ ID NO:120:

(  i  ) SEQUENCE CHARACTERISTICS:
        (  A  ) LENGTH: 35 amino acids
        (  B  ) TYPE: amino acid
        (  D  ) TOPOLOGY: unknown (  i  i  ) MOLECULE TYPE: protein (  i x  ) FEATURE:
        (  A  ) NAME/KEY: Modified-site
        (  B  ) LOCATION: 35
        (  D  ) OTHER INFORMATION: /note= "Where "X"is selected from
            the group consisting of Hol, Ho, a homoserine
            amide, or the sequence of amino acids comprising
            residues 35- 84 of PTH."

(  i x  ) FEATURE:
        (  A  ) NAME/KEY: Modified-site
        (  B  ) LOCATION: 8
        (  D  ) OTHER INFORMATION: /note= "The leucine residue at
            position 8 may be replaced with methionine."

(  i x  ) FEATURE:
        (  A  ) NAME/KEY: Modified-site
        (  B  ) LOCATION: 18
        (  D  ) OTHER INFORMATION: /note= "The leucine residue at
            position 18 may be replaced with a methionine
            residue."

(  x i  ) SEQUENCE DESCRIPTION: SEQ ID NO:120:

| Ser | Val | Ser | Glu | Ile | Gln | Leu | Leu | His | Asn | Leu | Gly | Lys | His | Leu | Asn |
|---|---|---|---|---|---|---|---|---|---|---|---|---|---|---|---|
| 1 | | | | 5 | | | | | 10 | | | | | 15 | |

| Glu | Leu | Glu | Arg | Val | Glu | Trp | Leu | Arg | Lys | Lys | Leu | Glu | Asp | Val | His |
|---|---|---|---|---|---|---|---|---|---|---|---|---|---|---|---|
| | | | 20 | | | | | 25 | | | | | 30 | | |

| Asn | Tyr | Xaa |
|---|---|---|
| | | 35 |

( 2 ) INFORMATION FOR SEQ ID NO:121:

(  i  ) SEQUENCE CHARACTERISTICS:
        (  A  ) LENGTH: 35 amino acids
        (  B  ) TYPE: amino acid
        (  D  ) TOPOLOGY: unknown (  i  i  ) MOLECULE TYPE: protein (  i x  ) FEATURE:
        (  A  ) NAME/KEY: Modified-site
        (  B  ) LOCATION: 35
        (  D  ) OTHER INFORMATION: /note= "Where "X"is selected from
            the group consisting of Hol, Ho, a homoserine
            amide, or the sequence of amino acids comprising residues 35-84 of PTH."

(ix) FEATURE:
    (A) NAME/KEY: Modified-site
    (B) LOCATION: 8
    (D) OTHER INFORMATION: /note= "The leucine residue at position 8 may be replaced with methionine."

(ix) FEATURE:
    (A) NAME/KEY: Modified-site
    (B) LOCATION: 18
    (D) OTHER INFORMATION: /note= "The leucine residue at position 18 may be replaced with a methionine residue."

(xi) SEQUENCE DESCRIPTION: SEQ ID NO:121:

| Ser | Val | Ser | Glu | Ile | Gln | Leu | Leu | His | Asn | Leu | Gly | Lys | His | Arg | Asn |
|---|---|---|---|---|---|---|---|---|---|---|---|---|---|---|---|
| 1 | | | | 5 | | | | | 10 | | | | | 15 | |
| Ser | Leu | Glu | Arg | Val | Arg | Trp | Leu | Arg | Lys | Lys | Leu | Gln | Asp | Val | His |
| | | | 20 | | | | 25 | | | | | 30 | | | |
| Asn | Tyr | Xaa | | | | | | | | | | | | | |
| | | 35 | | | | | | | | | | | | | |

(2) INFORMATION FOR SEQ ID NO:122:

(i) SEQUENCE CHARACTERISTICS:
    (A) LENGTH: 35 amino acids
    (B) TYPE: amino acid
    (D) TOPOLOGY: unknown (ii) MOLECULE TYPE: protein (ix) FEATURE:
    (A) NAME/KEY: Modified-site
    (B) LOCATION: 35
    (D) OTHER INFORMATION: /note= "Where "X"is selected from the group consisting of Hol, Ho, a homoserine amide, or the sequence of amino acids comprising residues 35-84 of PTH."

(ix) FEATURE:
    (A) NAME/KEY: Modified-site
    (B) LOCATION: 8
    (D) OTHER INFORMATION: /note= "The leucine residue at position 8 may be replaced with methionine."

(ix) FEATURE:
    (A) NAME/KEY: Modified-site
    (B) LOCATION: 18
    (D) OTHER INFORMATION: /note= "The leucine residue at position 18 may be replaced with a methionine residue."

(xi) SEQUENCE DESCRIPTION: SEQ ID NO:122:

| Ser | Val | Ser | Glu | Ile | Gln | Leu | Leu | His | Asn | Leu | Gly | Lys | His | Arg | Asn |
|---|---|---|---|---|---|---|---|---|---|---|---|---|---|---|---|
| 1 | | | | 5 | | | | | 10 | | | | | 15 | |
| Ser | Leu | Glu | Arg | Val | Glu | Trp | Leu | Arg | Lys | Lys | Leu | Gln | Arg | Val | His |
| | | | 20 | | | | 25 | | | | | 30 | | | |
| Asn | Tyr | Xaa | | | | | | | | | | | | | |
| | | 35 | | | | | | | | | | | | | |

(2) INFORMATION FOR SEQ ID NO:123:

(i) SEQUENCE CHARACTERISTICS:
    (A) LENGTH: 35 amino acids
    (B) TYPE: amino acid
    (D) TOPOLOGY: unknown (ii) MOLECULE TYPE: protein (ix) FEATURE:
    (A) NAME/KEY: Modified-site (B) LOCATION: 35
(D) OTHER INFORMATION: /note= "Where "X"is selected from the group consisting of Hol, Ho, a homoserine amide, or the sequence of amino acids comprising residues 35- 84 of PTH."

(ix) FEATURE:
(A) NAME/KEY: Modified-site
(B) LOCATION: 8
(D) OTHER INFORMATION: /note= "The leucine residue at position 8 may be replaced with methionine."

(ix) FEATURE:
(A) NAME/KEY: Modified-site
(B) LOCATION: 18
(D) OTHER INFORMATION: /note= "The leucine residue at position 18 may be replaced with a methionine residue."

(xi) SEQUENCE DESCRIPTION: SEQ ID NO:123:

| Ser | Val | Ser | Glu | Ile | Gln | Leu | Leu | His | Asn | Leu | Gly | Lys | His | Leu | Asn |
|---|---|---|---|---|---|---|---|---|---|---|---|---|---|---|---|
| 1 | | | | 5 | | | | | 10 | | | | | 15 | |
| Ser | Leu | Arg | Arg | Val | Arg | Trp | Leu | Arg | Lys | Lys | Leu | Gln | Asp | Val | His |
| | | | 20 | | | | 25 | | | | | 30 | | | |
| Asn | Tyr | Xaa | | | | | | | | | | | | | |
| | | 35 | | | | | | | | | | | | | |

(2) INFORMATION FOR SEQ ID NO:124:

(i) SEQUENCE CHARACTERISTICS:
(A) LENGTH: 35 amino acids
(B) TYPE: amino acid
(D) TOPOLOGY: unknown (ii) MOLECULE TYPE: protein (ix) FEATURE:
(A) NAME/KEY: Modified-site
(B) LOCATION: 35
(D) OTHER INFORMATION: /note= "Where "X"is selected from the group consisting of Hol, Ho, a homoserine amide, or the sequence of amino acids comprising residues 35- 84 of PTH."

(ix) FEATURE:
(A) NAME/KEY: Modified-site
(B) LOCATION: 8
(D) OTHER INFORMATION: /note= "The leucine residue at position 8 may be replaced with methionine."

(ix) FEATURE:
(A) NAME/KEY: Modified-site
(B) LOCATION: 18
(D) OTHER INFORMATION: /note= "The leucine residue at position 18 may be replaced with a methionine residue."

(xi) SEQUENCE DESCRIPTION: SEQ ID NO:124:

| Ser | Val | Ser | Glu | Ile | Gln | Leu | Leu | His | Asn | Leu | Gly | Lys | His | Arg | Asn |
|---|---|---|---|---|---|---|---|---|---|---|---|---|---|---|---|
| 1 | | | | 5 | | | | | 10 | | | | | 15 | |
| Ser | Leu | Arg | Arg | Val | Arg | Trp | Leu | Arg | Lys | Lys | Leu | Lys | Asp | Val | His |
| | | | 20 | | | | 25 | | | | | 30 | | | |
| Asn | Tyr | Xaa | | | | | | | | | | | | | |
| | | 35 | | | | | | | | | | | | | |

(2) INFORMATION FOR SEQ ID NO:125:

(i) SEQUENCE CHARACTERISTICS:
(A) LENGTH: 585 amino acids
(B) TYPE: amino acid
(D) TOPOLOGY: unknown ( i i ) MOLECULE TYPE: protein ( i x ) FEATURE:
    ( A ) NAME/KEY: Protein
    ( B ) LOCATION: 1..585
    ( D ) OTHER INFORMATION: /note= "PTH receptor"

( x i ) SEQUENCE DESCRIPTION: SEQ ID NO:125:

```
Met Gly Ala Pro Arg Ile Ser His Ser Leu Ala Leu Leu Leu Cys Cys
 1               5                  10                  15

Ser Val Leu Ser Ser Val Tyr Ala Leu Val Asp Ala Asp Asp Val Ile
             20                  25                  30

Thr Lys Glu Glu Gln Ile Ile Leu Leu Arg Asn Ala Gln Ala Gln Cys
         35                  40                  45

Glu Gln Arg Leu Lys Glu Val Leu Arg Val Pro Glu Leu Ala Glu Ser
     50                  55                  60

Ala Lys Asp Trp Met Ser Arg Ser Ala Lys Thr Lys Lys Glu Lys Pro
 65                  70                  75                  80

Ala Glu Lys Leu Tyr Pro Gln Ala Glu Glu Ser Arg Glu Val Ser Asp
                 85                  90                  95

Arg Ser Arg Leu Gln Asp Gly Phe Cys Leu Pro Glu Trp Asp Asn Ile
                100                 105                 110

Val Cys Trp Pro Ala Gly Val Pro Gly Lys Val Val Ala Val Pro Cys
            115                 120                 125

Pro Asp Tyr Phe Tyr Asp Phe Asn His Lys Gly Arg Ala Tyr Arg Arg
        130                 135                 140

Cys Asp Ser Asn Gly Ser Trp Glu Leu Val Pro Gly Asn Asn Arg Thr
145                 150                 155                 160

Trp Ala Asn Tyr Ser Glu Cys Val Lys Phe Leu Thr Asn Glu Thr Arg
                165                 170                 175

Glu Arg Glu Val Phe Asp Arg Leu Gly Met Ile Tyr Thr Val Gly Tyr
            180                 185                 190

Ser Ile Ser Leu Gly Ser Leu Thr Val Ala Val Leu Ile Leu Gly Tyr
        195                 200                 205

Phe Arg Arg Leu His Cys Thr Arg Asn Tyr Ile His Met His Leu Phe
    210                 215                 220

Val Ser Phe Met Leu Arg Ala Val Ser Ile Phe Ile Lys Asp Ala Val
225                 230                 235                 240

Leu Tyr Ser Gly Val Ser Thr Asp Glu Ile Glu Arg Ile Thr Glu Glu
                245                 250                 255

Glu Leu Arg Ala Phe Thr Glu Pro Pro Pro Ala Asp Lys Ala Gly Phe
            260                 265                 270

Val Gly Cys Arg Val Ala Val Thr Val Phe Leu Tyr Phe Leu Thr Thr
        275                 280                 285

Asn Tyr Tyr Trp Ile Leu Val Glu Gly Leu Tyr Leu His Ser Leu Ile
    290                 295                 300

Phe Met Ala Phe Phe Ser Glu Lys Lys Tyr Leu Trp Gly Phe Thr Leu
305                 310                 315                 320

Phe Gly Trp Gly Leu Pro Ala Val Phe Val Ala Val Trp Val Thr Val
                325                 330                 335

Arg Ala Thr Leu Ala Asn Thr Glu Cys Trp Asp Leu Ser Ser Gly Asn
            340                 345                 350

Lys Lys Trp Ile Ile Gln Val Pro Ile Leu Ala Ala Ile Val Val Asn
        355                 360                 365

Phe Ile Leu Phe Ile Asn Ile Ile Arg Val Leu Ala Thr Lys Leu Arg
    370                 375                 380
```

```
Glu  Thr  Asn  Ala  Gly  Arg  Cys  Asp  Thr  Arg  Gln  Gln  Tyr  Arg  Lys  Leu
385                      390                      395                      400

Leu  Lys  Ser  Thr  Leu  Val  Leu  Met  Pro  Leu  Phe  Gly  Val  His  Tyr  Ile
               405                      410                      415

Val  Phe  Met  Ala  Thr  Pro  Tyr  Thr  Glu  Val  Ser  Gly  Ile  Leu  Trp  Gln
               420                 425                      430

Val  Gln  Met  His  Tyr  Glu  Met  Leu  Phe  Asn  Ser  Phe  Gln  Gly  Phe  Phe
          435                 440                      445

Val  Ala  Ile  Ile  Tyr  Cys  Phe  Cys  Asn  Gly  Glu  Val  Gln  Ala  Glu  Ile
          450            455                      460

Lys  Lys  Ser  Trp  Ser  Arg  Trp  Thr  Leu  Ala  Leu  Asp  Phe  Lys  Arg  Lys
465                      470                 475                      480

Ala  Arg  Ser  Gly  Ser  Ser  Thr  Tyr  Ser  Tyr  Gly  Pro  Met  Val  Ser  His
               485                      490                      495

Thr  Ser  Val  Thr  Asn  Val  Gly  Pro  Arg  Gly  Gly  Leu  Ala  Leu  Ser  Leu
               500                 505                      510

Ser  Pro  Arg  Leu  Ala  Pro  Gly  Ala  Gly  Ala  Ser  Ala  Asn  Gly  His  His
          515                 520                      525

Gln  Leu  Pro  Gly  Tyr  Val  Lys  His  Gly  Ser  Ile  Ser  Glu  Asn  Ser  Leu
     530                      535                 540

Pro  Ser  Ser  Gly  Pro  Glu  Pro  Gly  Thr  Lys  Asp  Asp  Gly  Tyr  Leu  Asn
545                      550                 555                      560

Gly  Ser  Gly  Leu  Tyr  Glu  Pro  Met  Val  Gly  Glu  Gln  Pro  Pro  Pro  Leu
                    565                      570                 575

Leu  Glu  Glu  Glu  Arg  Glu  Thr  Val  Met
               580                 585
```

( 2 ) INFORMATION FOR SEQ ID NO:126:

( i ) SEQUENCE CHARACTERISTICS:
        ( A ) LENGTH: 18 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:126:

```
Cys  Leu  Glu  Pro  Tyr  Thr  Ala  Cys  Asp  Leu  Ala  Pro  Pro  Ala  Gly  Thr
1                   5                      10                      15

Thr  Asp
```

( 2 ) INFORMATION FOR SEQ ID NO:127:

( i ) SEQUENCE CHARACTERISTICS:
        ( A ) LENGTH: 47 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:127:

```
Cys  Leu  Glu  Pro  Tyr  Thr  Ala  Cys  Asp  Leu  Ala  Pro  Pro  Ala  Gly  Thr
1                   5                      10                      15

Thr  Asp  Ala  Ala  His  Pro  Gly  Arg  Ser  Val  Val  Pro  Ala  Leu  Leu  Pro
               20                 25                      30

Leu  Leu  Ala  Gly  Thr  Leu  Leu  Leu  Leu  Glu  Thr  Ala  Thr  Ala  Pro
               35                 40                      45
```

( 2 ) INFORMATION FOR SEQ ID NO:128:

( i ) SEQUENCE CHARACTERISTICS:
        ( A ) LENGTH: 451 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:128:

| | | | | | | |
|---|---|---|---|---|---|---|
| CATATGGTGC | ACTCTCAGTA | CAATCTGCTC | TGATGCCGCA | TAGTTAAGCC | AGTATACACT | 60 |
| CCGCTATCGC | TACGTGACTG | GGTCATGGCT | GCGCCCCGAC | ACCCGCCAAC | ACCCGCTGAC | 120 |
| GCGCCCTGAC | GGGCTTGTCT | GCTCCCGGCA | TCCGCTTACA | GACAAGCTGT | GACCGTCTCC | 180 |
| GGGAGCTGCA | TGTGTCAGAG | GTTTTACCGT | CATCACCGAA | ACGCGCGAGG | CAGCAAGGAG | 240 |
| ATGGCGCCCA | ACAGTCCCCC | GGCCACGGGG | CCTGCCACCA | TACCCACGCC | GAAACAAGCG | 300 |
| CTCATGAGCC | CGAAGTGGCG | AGCCCGATCT | TCCCCATCGG | TGATGTCGGC | GATATAGGCG | 360 |
| CCAGCAACCG | CACCTGTGGC | GCCGGTGATG | CCGGCCACGA | TGCGTCCGGC | GTAGAGGATC | 420 |
| TAATTCTCAT | GTTTGACAGC | TTATCATCGA | T | | | 451 |

( 2 ) INFORMATION FOR SEQ ID NO:129:

( i ) SEQUENCE CHARACTERISTICS:
        ( A ) LENGTH: 91 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:129:

| | | | | | | |
|---|---|---|---|---|---|---|
| GGCAGGCTAG | CTAACTAATG | GAGGATACAT | AAATGGCTCA | CCACCACCAT | CACCATGTCG | 60 |
| ACTGACGACT | CGAGTAATAA | AAGCTTGGTC | G | | | 91 |

( 2 ) INFORMATION FOR SEQ ID NO:130:

( i ) SEQUENCE CHARACTERISTICS:
        ( A ) LENGTH: 91 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:130:

| | | | | | | |
|---|---|---|---|---|---|---|
| CGACCAAGCT | TTTATTACTC | GAGTCGTCAG | TCGACATGGT | GATGGTGGTG | GTGAGCCATT | 60 |
| TATGTATCCT | CCATTAGTTA | GCTAGCCTGC | C | | | 91 |

( 2 ) INFORMATION FOR SEQ ID NO:131:

( i ) SEQUENCE CHARACTERISTICS:
        ( A ) LENGTH: 74 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:131:

| | | | | | | |
|---|---|---|---|---|---|---|
| GGACGGCTCG | AGATGTCCGT | TTCCGAAATC | CAGCTGCTGC | ACAACCTGGG | TAAACACCTG | 60 |
| AACTCCCTGG | AACG | | | | | 74 |

( 2 ) INFORMATION FOR SEQ ID NO:132:

(i) SEQUENCE CHARACTERISTICS:
   (A) LENGTH: 74 base pairs
   (B) TYPE: nucleic acid
   (C) STRANDEDNESS: single
   (D) TOPOLOGY: linear (ii) MOLECULE TYPE: DNA (genomic)

(xi) SEQUENCE DESCRIPTION: SEQ ID NO:132:

CCTGCCGTCG ACCATGTAGT TGTGAACGTC CTGCAGTTTT TTACGCAGCC ATTCAACACG    60

TTCCAGGGAG TTCA    74

We claim:

1. A peptide comprising the sequence SVSEIQLMHNLGKHLNSMERVEWLRKKLQDVHNF (SEQ ID NO:2) wherein:
   positions 11, 19, 22, and 29 have been substituted with an arginine; and
   position 34 is couple to Hol, Ho, a homoserine amide, or the sequence of amino acids comprising residues 35–84 of PTH (SEQ ID NO:1).

2. The peptide of claim 1, wherein position 34 is coupled to Hol.

3. A pharmaceutical composition comprising a peptide of claim 1 in association with a pharmaceutical carrier or diluent.

* * * * *